US008198285B2

(12) United States Patent
Feng et al.

(10) Patent No.: US 8,198,285 B2
(45) Date of Patent: Jun. 12, 2012

(54) PYRAZINE DERIVATIVES

(75) Inventors: Tao Feng, Shanghai (CN); Hitesh Jayantilal Sanganee, Loughborough (GB); Hiroki Wada, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 13/008,154

(22) Filed: Jan. 18, 2011

(65) Prior Publication Data

US 2012/0022082 A1 Jan. 26, 2012

Related U.S. Application Data

(60) Provisional application No. 61/296,196, filed on Jan. 19, 2010.

(51) Int. Cl.
*A61K 31/497* (2006.01)
*A61P 35/00* (2006.01)
*A61P 19/08* (2006.01)
*C07D 401/12* (2006.01)

(52) U.S. Cl. .................................. 514/255.05
(58) Field of Classification Search ............... None
See application file for complete search history.

(56) References Cited

U.S. PATENT DOCUMENTS

| 7,576,093 | B2 | 8/2009 | Bhat et al. |
| 2003/0176484 | A1 | 9/2003 | Day-Lollini et al. |
| 2004/0180905 | A1 | 9/2004 | Munchhof |
| 2005/0054663 | A1 | 3/2005 | Bennett et al. |
| 2006/0252045 | A1 | 11/2006 | Chatterjee-Kishore et al. |
| 2007/0213322 | A1 | 9/2007 | Bhat et al. |

FOREIGN PATENT DOCUMENTS

| WO | 01/57022 | A2 | 8/2001 |
| WO | 03/004472 | A1 | 1/2003 |
| WO | 03/004475 | A1 | 1/2003 |
| WO | 03/057202 | A1 | 7/2003 |
| WO | 03/076442 | A1 | 9/2003 |
| WO | 03/093297 | A2 | 11/2003 |
| WO | 2004/055005 | A1 | 7/2004 |
| WO | 2004/055006 | A1 | 7/2004 |
| WO | 2004/055009 | A1 | 7/2004 |
| WO | 2005/020921 | A2 | 3/2005 |
| WO | 2005/027883 | A1 | 3/2005 |
| WO | 2005/039485 | A2 | 5/2005 |
| WO | 2005/079802 | A1 | 9/2005 |
| WO | 2007/102770 | A1 | 9/2007 |
| WO | 2008/106692 | A1 | 9/2008 |
| WO | 2010/054398 | A1 | 5/2010 |

OTHER PUBLICATIONS

Berg et al., caplus an 2004:534194.*
Abdul et al. "Inhibiting Glycogen Synthase Kinase-3 (GSK-3) Prevents the Development of Myeloma Bone Disease" Abstract No. 008; Cancer and Bone Society meeting in Sydney in Mar. 2009, Bone 44 (suppl), 2009 (abstract).

Bain et al. Activated β-catenin induces osteoblast differentiation of C3H10T1/2 cells and participates in BMP2 mediated signal transduction; Biochem. Biophys. Res. Commun., 2003, 301:84-91.
Bell, Norman H. "Advances in the Treatment of Osteoporosis"; Current Drug Targets—Immune, Endocrine & Metabolic Disorders, 2001, 1: 93-102.
Bennett et al. 'Regulation of Wnt Signaling during Adipogenesis'; The Journal of Biological Chemistry vol. 277, No. 34, Issue of Aug. 23, pp. 30998-31004, 2002.
Bennett et al. 2005 "Regulation of osteoblastogenesis and bone mass by Wnt10b" PNAS, Mar. 1,2005, 3324-3329 vol. 102, No. 9.
Boyden et al. "High Bone Density due to a Mutation in LDL-Receptor-Related Protein 5" The New England Journal of Medicine; vol. 346, No. 20, May 16, 2002, 1513-1521.
Boyle, "Secondary Osteoporosis" Medline Abstract of Balilliere's clinical rheumatology (Oct. 1993) vol. 7 No. 3 pp. 515-534.
Brändström et al. Gsk3 Inhibition Increases Trabecular Bone Mass in Mice American Society for Bone mineral Research Annual Meeting 2006, Philadelphia, Abstract No. SA396, Sep. 2006.
Albrektsson et al. "Osseointegrated Titaniumim Plants—Requirements for Ensuring a Long-Lasting, Direct Bone-to-Implant Anchorage in Man" Acta Orthop. Scand, 1981, 52: 155-170.
Broulik et al. "Alterations in human serum alkaline phosphatase and its bone isoenzyme by chronic administration of lithium" Clinica Chemica Acta, 1984, 140:151-155.
Clément-Lacroix et al. "Lrp5-independent activation of Wnt signaling by lithium chloride increases bone formation and bone mass in mice" PNAS Nov. 29, 2005 vol. 102 No. 48 17406-1741. www.pnas.org_cgi_doi_10.1073_pnas.0505259102.
Day et al. "Wnt/β-Catenin Signaling in Mesenchymal Progenitors Controls Osteoblast and Chondrocyte Differentiation during Vertebrate Skeletogenesis" Development Cell, vol. 8, 739-750, May 2005.
Frost, "Osteoporosis Treatment: Quo Vadis? (A Brief Overview)" Medline Abstract of Medicina (1997) vol. 57 Suppl 1;119-26.
Gambardella et al. "Glycogen synthase kinase-3α/β inhibition promotes in-vivo amplification of endogeneous mesenchymal progenitors with osteogenic and adipogenic and their differentiation to the osteogenic lineage" 4th UK Mesenchymal Stem Cell Meeting Apr. 14, 2010 (abstract).

(Continued)

*Primary Examiner* — Sun Jae Loewe
(74) *Attorney, Agent, or Firm* — Astrazeneca AB

(57) ABSTRACT

The invention concerns pyrazine derivatives of the Formula I

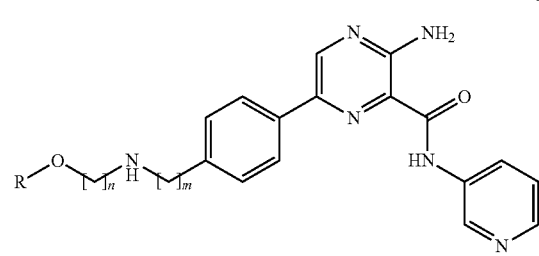

or pharmaceutically-acceptable salts thereof; wherein each of n, m and R has any of the meanings defined hereinbefore in the description; processes for their preparation, pharmaceutical compositions containing them and their use in the manufacture of a medicament for use in the treatment of bone-related disorders or conditions.

6 Claims, 18 Drawing Sheets

OTHER PUBLICATIONS

Gambardella et al. "Glycogen synthase kinase-3α/β inhibition promotes in-vivo amplification of endogeneous mesenchymal progenitors with osteogenic and adipogenic potential and their differentiation to the osteogenic lineage" 4th UK Mesenchymal Stem Cell Meeting 2010 (Poster).

Gambardella et al. "Glycogen synthase kinase-3α/β inhibition promotes in-vivo amplification of endogeneous mesenchymal progenitors with osteogenic and adipogenic potential and their differentiation to the osteogenic lineage" J Bone Min. Res. Apr. 2011; vol. 26(4) 811-821.

G-Amlak et al. "Regulation of myeloma cell growth through Akt/Gsk3/forkhead signaling pathway" Biochemical and Biophysical Research Communications, 2002, vol. 297,760-764.

Gong et al. "Osteoporosis-Pseudoglioma Syndrome, a Disorder Affecting Skeletal Strength and Vision, Is Assigned to Chromosome Region 11q12-13" Am. J. Hum. Genet 1996, 59, 146-151.

Gong et al. "LDL Receptor-Related Protein 5 (LRP5) Affects Bone Accrual and Eye Development"; Cell, vol. 107, 513-523, Nov. 2001.

Gregory et al. "How Wnt Signaling Affects Bone Repair by Mesenchymal Stem Cells from the Bone Marrow" Ann. N.Y. Acad. Sci. 1049: 97-106 (2005).

Highlights of Prescribing Information for Velcade: http://www.accessdata.fda.gov/drugsatfda_docs/label/2008/021602s015lbl.pdf.

Hill et al. "Canonical Wnt/β-Catenin Signaling Prevents Osteoblasts from Differentiating into Chondrocytes" Developmental Cell, vol. 8, 727-738, May 2005.

Johansen et al. "Bisphosphonates and the Treatment of Bone Disease in the Elderly" Medline Abstract of Drugs and Aging (Feb. 1996) vol. 8; No. 2 pp. 113-126.

Jope et al. "Glycogen Synthase Kinase-3 (GSK3): Inflammation, Diseases, and Therapeutics" Neurochem Res 2007, 32: 577-595.

Kannoji et al. "GSK3β: A master switch and a promising target" Expert Opin. Ther. Targets, 2008, 12(11), 1443-1455.

Kapadia et al. "Glycogen synthase kinase 3 controls endochondral bone development: Contribution of fibroblast growth factor 18", Developmental Biology, 2005, vol. 285, p. 496-507, abstract.

Kugimiya F et al. "GSK-3β Controls Osteogenesis through Regulating Runx2 Activity" PLoS One, 2007, (9), e837 1-9.

Kulkarni et al. "Changes in Osteoblast, Chondrocyte, and Adipocyte Lineages Mediate the Bone Anabolic Actions of PTH and Small Modecule GCK-3 Inhibitor" J Cell Biochem 2007, 102, 1504-1518.

Kulkarni et al. "Orally bioavailable GSK-3α/β Dual Inhibitor Increases Markers of Cellular Differentiation In Vitro and Bone Mass In Vivo"; Journal of Bone Mineral Research Jun. 2006; 21(6):910-920.

Little et al. "High Bone Density Due to a Mutation in LDL-Receptor-Related Protein 5" N. Engl. J. Med. 2002, vol. 347, 943-944.

Little et al. "A Mutation in the LDL Receptor—Related Protein 5 Gene Results in the Autosomal Dominant High-Bone-Mass Trait" American. Journal of Human Genetics; 70:11-19, 2002.

Ross et al. "Inhibition of Adipogenesis by Wnt Signaling" Aug. 2000; vol. 289 Science; 950-953; www.sciencemag.org.

Skoglund et al. "Simvastatin Improves Fracture Healing in Mice"; Journal of Bone and Mineral Research vol. 17, No. 2002, 2004-2008.

Smith et al, "Glucocorticoids Inhibit the Transcriptional Activity of LEF/TCF in Differentiating Osteoblasts in a Glycogen Synthase Kinase-3β-dependent and-independent Manner" Journal of Biological Chemistry, 2005, 280, 3, 2388-2394.

Smith et al. "Glucocorticoids Inhibit Cell Cycle Progression in Differentiating Osteoblasts via Glycogen Synthase" Kinase-3β'J. Biol. Chem., 2002, vol. 277 No. 20: 18191-18197.

Tian et al. "The Role of the Wnt-Signaling Antagonist DKK1 in the Development of Osteolytic Lesions in Multiple Myeloma" N engl j med 349;26, 2003, 2483-2494.

Tobias et al. "Novel Therapeutic Targets in Osteoporosis" Expert Opinion on Therapeutic Targets; Feb. 2002, 41-56.

Van Wesenbeeck et al. "Six Novel Missense Mutations in the LDL Receptor-Related Protein 5(LRP5) Gene in Different Conditions with an Increased Bone Density" American Journal of Human Genetics; 72:763-771, 2003.

Wang et al, "Inhibition of glycogen synthase kinase-3β attenuates glucocorticoid-induced bone loss" Life Sciences, 2009, 85, 685-692.

\* cited by examiner

DMSO  300nM

PYRAZINE DERIVATIVES

This application claims the benefit under 35 U.S.C. §119 (e) of U.S. Application No. 61/296,196 filed on 19 Jan. 2010.

The invention concerns certain novel pyrazine derivatives, or pharmaceutically-acceptable salts thereof, which possess bone formation activity and are accordingly useful in methods of treatment of the human or animal body. The invention also concerns processes for the manufacture of said pyrazine derivatives, pharmaceutical compositions containing said pyrazine derivatives and use of said pyrazine derivatives in therapeutic methods, for example in the manufacture of medicaments for use in the prevention or treatment of bone-related disorders or conditions in a warm-blooded animal such as man.

The present invention especially relates to pyrazine derivatives that are inhibitors of Glycogen synthase kinase 3 (GSK3).

GSK3 is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 is a multi-functional kinase that regulates a number of different signaling pathways involved in important cellular functions, structure, gene expression, mobility and survival (Jope et al Neurochem Res. 2007, 32, 577-595). GSK3 phosphorylates several substrates including tau, $\beta$-catenin-, glycogen synthase, pyruvate dehydrogenase and elongation initiation factor 2b (eIF2b). Insulin and growth factors activate protein kinase B, which phosphorylates GSK3 on serine 9 residue and inactivates it (Kannoji et al, Expert Opin. Ther. Targets 2008, 12, 1443-1455).

GSK3, is a constitutively active kinase, which is now recognized to regulate pathways including Wnt/$\beta$-catenin, Notch and PI3K and hedgehog signaling pathways and has a role in regulating processes including osteogenesis, chrondogenesis and adipogenesis (Kulkarni et al., J Cell Biochem, 2007, 102, 1504-1518). GSK3$\beta$, one of the isoforms of GSK3, has been demonstrated to regulate bone formation both in vitro and in vivo. Inhibition of GSK3 prevents the phosphorylation of $\beta$-catenin leading to $\beta$-catenin stabilization, accumulation and translocation from cytoplasm to nucleus. This process is thought to lead to activation of transcription factors and transcription of specific genes involved in bone formation, for example induction of expression of alkaline phosphatase mRNA and protein, a marker of early osteoblast differentiation (Bain et al., Biochem. Biophys. Res. Commun., 2003, 301:84-91). GSK3 inhibition in murine mesenchymal stem cells induces markers of osteoblast differentiation and bone formation in vitro (Kulkarni et al., JBMR, 2006, 6, 910-920). Inhibition of GSK3$\beta$ protects against glucocorticoid induced suppression of survival and differentiation of osteoblast cultures in vitro (MC3T3-E1 cells, Wang et al. Life Sciences, 2009, 85, 685-692). Heterozygous GSK3$\beta$-deficient mice displayed an increased bone formation (Kugimiya F et al., PLoS One, 2007, 2(9), e837, 1-9). In addition, particular inhibitors of GSK3 have been demonstrated to increase bone mass and improve bone strength in an ovariectomized animal model of bone loss (Kulkarni et al., JBMR, 2006, 21, 910-920) and attenuate glucocorticoid induced bone loss in animals (Wang et al. Life Sciences, 2009, 85, 685-692). In addition, inhibition of GSK3 prevents myeloma-induced suppression of bone formation and the development of osteolytic disease in the 5T2MM model of myeloma (Abdul et al., Bone, 2009, 44 (suppl. 1), S53 Abstract 103).

Genetic studies have established a link between bone mass in humans and Wnt signaling (Gong et al., Am. J. Hum. Genet. 1996, 59, 146-51: Little et al., N. Engl. J. Med., 2002, 347, 943-4). Genetic and pharmacological manipulations of Wnt signaling in mice have since then confirmed the central role of this pathway in regulating bone formation. Of the pathways activated by Wnts, it is signaling through the canonical (i.e., Wnt/$\beta$-catenin) pathway that increases bone mass through a number of mechanisms including renewal of stem cells, stimulation of pre-osteoblast replication, induction of osteoblastogenesis, and inhibition of osteoblast and osteocyte apoptosis. Therefore, enhancing Wnt pathway signaling with GSK3 inhibitors could be used for the treatment of bone-related disorders, or other conditions which involve a need for new and increased bone formation, for example osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

These findings suggest that pharmacological inhibitors of GSK3 enzymes should be of therapeutic value for treatment of the various forms of bone-related disorders or conditions, such as, for example osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

In addition to bone-related disorders or conditions, there is evidence that GSK3 enzymes play a role in other diseases. GSK3 inhibition may have beneficial effects in Alzheimer's disease, dementias, and taupathies, acute neurodegenerative diseases, bipolar disorders, schizophrenia, diabetes, alopecia, inflammatory disease, cancer, glaucoma and regenerative medicine. Thus inhibitors of GSK3 enzymes, are expected to be of value in is the prevention and treatment of a wide variety of diseases in addition to bone-related disorders or conditions.

The compounds, i.e. the pyrazine derivatives, of the invention have now surprisingly been found to possess potent bone forming activity, being useful in preventing or treating bone-related disorders or conditions. Without wishing to imply that the compounds disclosed in the present invention possess pharmacological activity only by virtue of an effect on a single biological process, it is believed that the compounds provide a bone forming effect by way of inhibition of GSK3 enzymes.

It is well known that severe problems such as toxicity or reduced efficacy may occur if plasma levels of one drug are altered by the co-administration of another drug. This phenomenon, which is often called drug-drug interactions, could occur if there is a change in the metabolism of one drug caused by the co-administration of another substance possessing liver enzyme inhibiting or inducing properties. Cytochromes P450 are the principal, hepatic xenobiotic metabolizing enzymes and the CYP (cytochrome P450) 3A4 isoform is generally regarded as one of the most important enzymes in the human liver as the majority of oxidised drugs have been biotransformed by this enzyme. Accordingly, it is undesirable to employ a medication having a significant degree of such liver enzyme inhibiting or inducing properties. This is particularly important in diseases such as those the compounds of the invention could be useful to treat. For example, anti-cancer drugs used in cancers that lead to bone lesions will often need to be co-administered with compounds for use in the prevention or treatment of bone-related disorders or conditions. Many anti-cancer drugs have a narrow therapeutic window (i.e. small margin between efficacious and toxic dose) and it is therefore critically important that plasma levels of such drugs are carefully controlled in order to avoid toxicity or reduced efficacy. One example of such an anti-cancer drug that is used as a primary treatment for multiple myeloma is the proteasome inhibitor bortezomib (known as Velcade), which has a very narrow therapeutic margin. This drug is extensively metabolised by CYP3A4 such that patients receiving co-w administration of any compound that may induce or inhibit this enzyme require close monitoring (see Highlights of Prescribing Information for Velcade: http://www.accessdata.fda.gov/drugsatfda_docs/label/2008/021602s015lbl.pdf). Accordingly, there is a need for novel compounds for use in the prevention or treatment of bone-related disorders or conditions that display low activity against liver enzymes such as CYP3A4. A particular compound of the invention, namely 3-amino-6-(4-{3-[(3-methoxypropyl)amino]propyl}phenyl)-N-pyridin-3-ylpyrazine-2-carboxamide tri-hydrochloride, has now surprisingly been found to possess such low activity against CYP3A4. A further advantageous property of 3-amino-6-(4-{3-[(3-methoxypropyl)amino]propyl}phenyl)-N-pyridin-3-ylpyrazine-2-carboxamide tri-hydrochloride, is that it does not display potent inhibitory activity against the cardiac $Na^+$ channel, hNav1.5.

Furthermore, certain compounds of the invention also display useful selectivity against GSK3 when compared to other particular kinases.

Figure 1A:
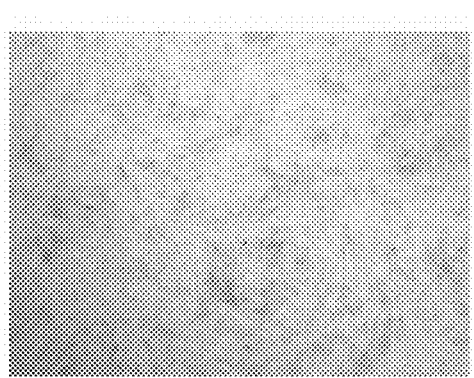
FIG. 1A: Images showing Alizarin red S staining of mineralised bone nodules in response to 300 nM 3-amino-6-(4-{3-[(3-methoxypropyl)amino]propyl}phenyl)-N-pyridin-3-ylpyrazine-2-carboxamide tri-hydrochloride compared with vehicle (0.2% DMSO) after 24 days of human adipose-derived stem cell culture. Experiments were performed in triplicate.
Figure 1A:
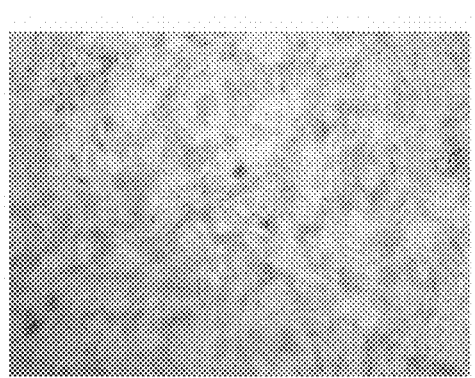

According to one aspect of the invention there is provided a pyrazine derivative of the Formula I

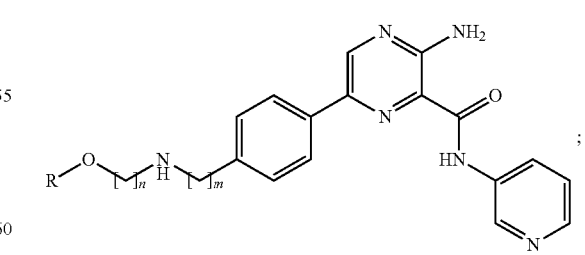

in which:
n is 2 or 3;
m is 2 or 3;
R is methyl or ethyl; or a pharmaceutically-acceptable salt thereof.

According to a further aspect of the invention there is provided a pyrazine derivative of the Formula I, which is 3-amino-6-(4-{3-[(3-methoxypropyl)amino]propyl}phenyl)-N-pyridin-3-ylpyrazine-2-carboxamide:

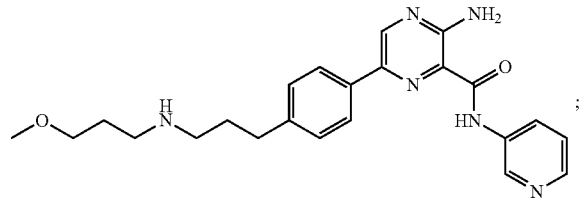

or a pharmaceutically-acceptable salt thereof.

It is to be understood that compounds of Formula I defined above may exhibit the phenomenon of tautomerism. It is to be understood that the present invention includes in its definition any such tautomeric form, or mixture of different tautomeric forms, which possess GSK3 enzyme inhibitory activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic or citric acid. A further suitable pharmaceutically-acceptable salt of a compound of the Formula I is, for example, a salt formed within the human or animal body after administration of a compound of the Formula I.

A particular pharmaceutically-acceptable salt of a compound of the Formula I is, an acid-addition salt of a compound of the Formula I with an acid selected from hydrochloric, hydrobromic, sulphuric, trifluoroacetic, citric, benzenesulphonic, p-toluenesulphonic, ethanesulphonic, DL-mandelic or benzoic acid.

According to one aspect of the invention, a particular pharmaceutically-acceptable salt of the compound of the Formula I is an acid-addition salt of a compound of the Formula I with hydrochloric acid.

According to a further aspect of the invention, a particular pharmaceutically-acceptable salt of the compound of the Formula I is an acid-addition salt of a compound of the Formula I with benzenesulphonic or p-toluenesulphonic acid.

According to a further aspect of the invention, a particular pharmaceutically-acceptable salt of the compound of the Formula I is an acid-addition salt of a compound of the Formula I with benzenesulphonic acid.

According to a further aspect of the invention, a particular pharmaceutically-acceptable salt of the compound of the Formula I is an acid-addition salt of a compound of the Formula I with p-toluenesulphonic acid.

According to a further aspect of the invention, a particular pharmaceutically-acceptable salt of the compound of the Formula I is an acid-addition salt of a compound of the Formula I with an acid selected from ethanesulphonic, DL-mandelic or benzoic acid.

It is further to be understood that a suitable pharmaceutically-acceptable solvate of a compound of the Formula I also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

Some compounds of the Formula I may exhibit polymorphism. It is to be understood that the present invention encompasses any polymorphic form, or mixtures thereof, which form possesses properties useful in the inhibition of glycogen synthase kinase-3 activity, it being well known in the art how to determine efficacy of a polymorphic form for the inhibition of glycogen synthase kinase-3 activity by the standard tests described hereinafter.

It is generally known that crystalline materials may be analysed using conventional techniques such as X-Ray Powder Diffraction (hereinafter XRPD) analysis, Differential Scanning calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, a particular crystalline form has been identified for the compound of Example 2.

Accordingly, a further aspect of the invention is Form B of 3-amino-6-(4-{3[(3-methoxypropyl)amino]propyl}phenyl)-N-pyridin-3-ylpyrazine-2-carboxamide.

All of the following XRPD data was measured as described in paragraph (viii) in the introduction of the Examples section.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with at least one specific peak at 2-theta=3.5° plus or minus 0.1° 2-theta.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with at least one specific peak at 2-theta=17.6° plus or minus 0.1° 2-theta.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with at least two specific peaks at 2-theta=3.5° and 17.6° wherein said values may be plus or minus 0.1° 2-s theta.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with specific peaks at 2-theta=3.5, 7.0, 9.5, 10.4, 12.4, 13.8, 14.1, 15.9, 17.6, 21.0° wherein said values may be plus or minus 0.1° 2-theta.

Figure 4:
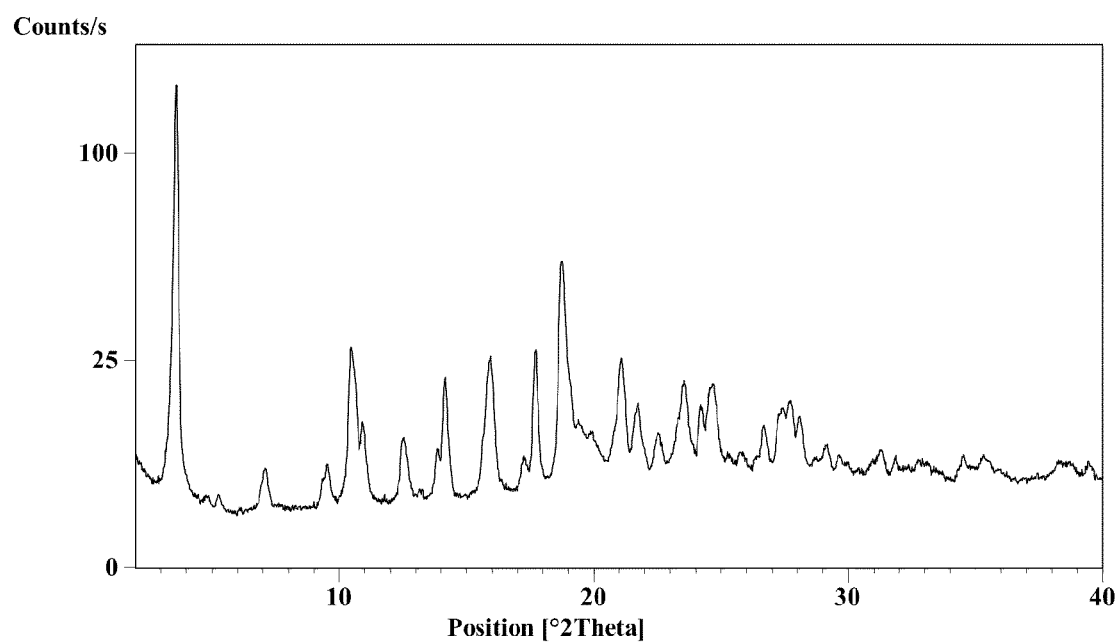
FIG. 4: X-Ray Powder Diffraction Pattern of Form B of 3-amino-6-(4-{3-[(3-methoxypropyl)amino]propyl}phenyl)-N-pyridin-3-ylpyrazine-2-carboxamide.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern substantially the same as the X-ray powder diffraction pattern shown in FIG. 4.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with at least one specific peak at 2-theta=3.5°.

According to a further aspect of the present invention, there is provided a crystalline form, Form B of 3-amino-6-(4-{3-[(3-methoxypropyl)amino]propyl}phenyl)-N-pyridin-3- ylpyrazine-2-carboxamide, which has an X-ray powder diffraction pattern with at least one specific peak at 2-theta=17.6°.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with at least two specific peaks at 2-theta=3.5° and 17.6°.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern with specific peaks at 2-theta=3.5, 7.0, 9.5, 10.4, 12.4, 13.8, 14.1, 15.9, 17.6, 21.0°.

According to a further aspect of the present invention, there is provided a crystalline form, Form B of 3-amino-6-(4-{3-[(3-methoxypropyl)amino]propyl}phenyl)-N-pyridin-3-ylpyrazine-2-carboxamide, which has an X-ray powder diffraction pattern as shown in FIG. 4.

As a further example, the compound of Example 3 exhibits polymorphism and two crystalline forms have been identified.

Accordingly, a further aspect of the invention is Form A of 3-amino-6-(4-{3-[(3-methoxypropyl)amino]propyl}phenyl)-N-pyridin-3-ylpyrazine-2-carboxamide mono-besylate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at about 2-theta=8.4°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at about 2-theta=14.5°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least two specific peaks at about 2-theta=8.4° and 14.5°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with specific peaks at about 2-theta=7.5, 8.4, 11.0, 14.5, 15.7, 18.5, 20.2, 22.0, 22.2, 23.0°.

Figure 6A:
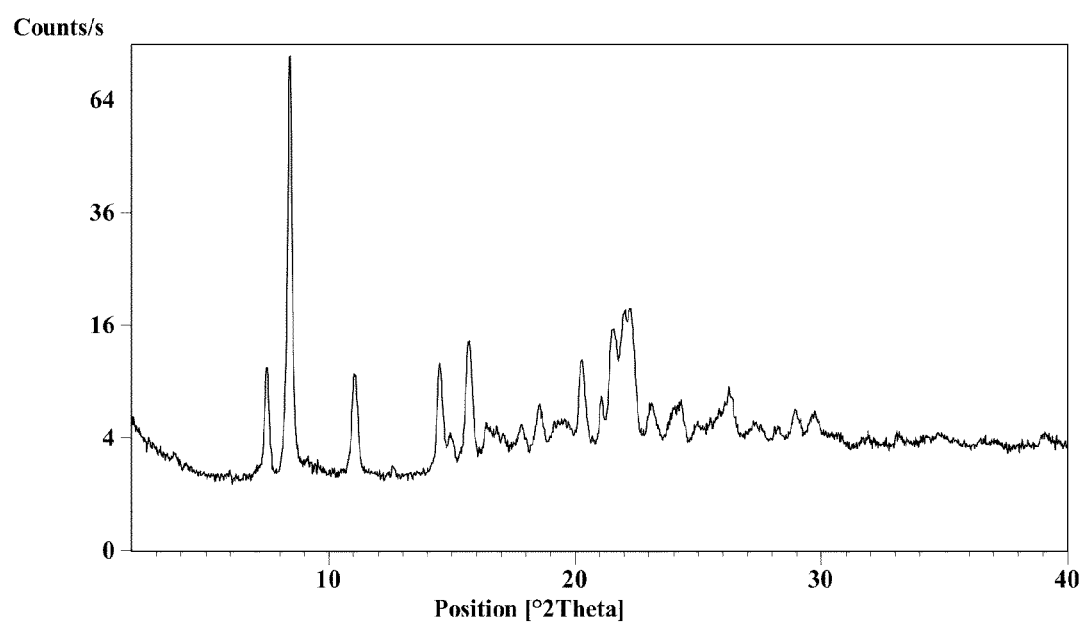
FIG. 6a: X-Ray Powder Diffraction Pattern for Form A of 3-amino-6-(4-{3[(3-methoxypropyl)amino]propyl}phenyl)-N-pyridin-3-ylpyrazine-2-carboxamide mono-besylate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern substantially the same as the X-ray powder diffraction pattern shown in FIG. 6a.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=8.4° plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=14.5° plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least two specific peaks at 2-theta=8.4° and 14.5° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with specific peaks at 2-theta=7.5, 8.4, 11.0, 14.5, 15.7, 18.5, 20.2, 22.0, 22.2, 23.0° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=8.4°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=14.5°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least two specific peaks at 2-theta=8.4° and 14.5°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern with specific peaks at 2-theta=7.5, 8.4, 11.0, 14.5, 15.7, 18.5, 20.2, 22.0, 22.2, 23.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-besylate, which has an X-ray powder diffraction pattern as shown in FIG. 6a.

Accordingly, a further aspect of the invention is Form C of 3-amino-6-(4-{3[(3-methoxypropyl)amino]propyl}phenyl)-N-pyridin-3-ylpyrazine-2-carboxamide mono-besylate.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least two specific peaks at about 2-theta=11.2°, 14.7° and 15.8°.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with specific peaks at about 2-theta=11.2, 12.6, 14.7, 15.5, 15.8, 16.8, 20.4, 21.1, 22.5, 26.5°.

Figure 6B:
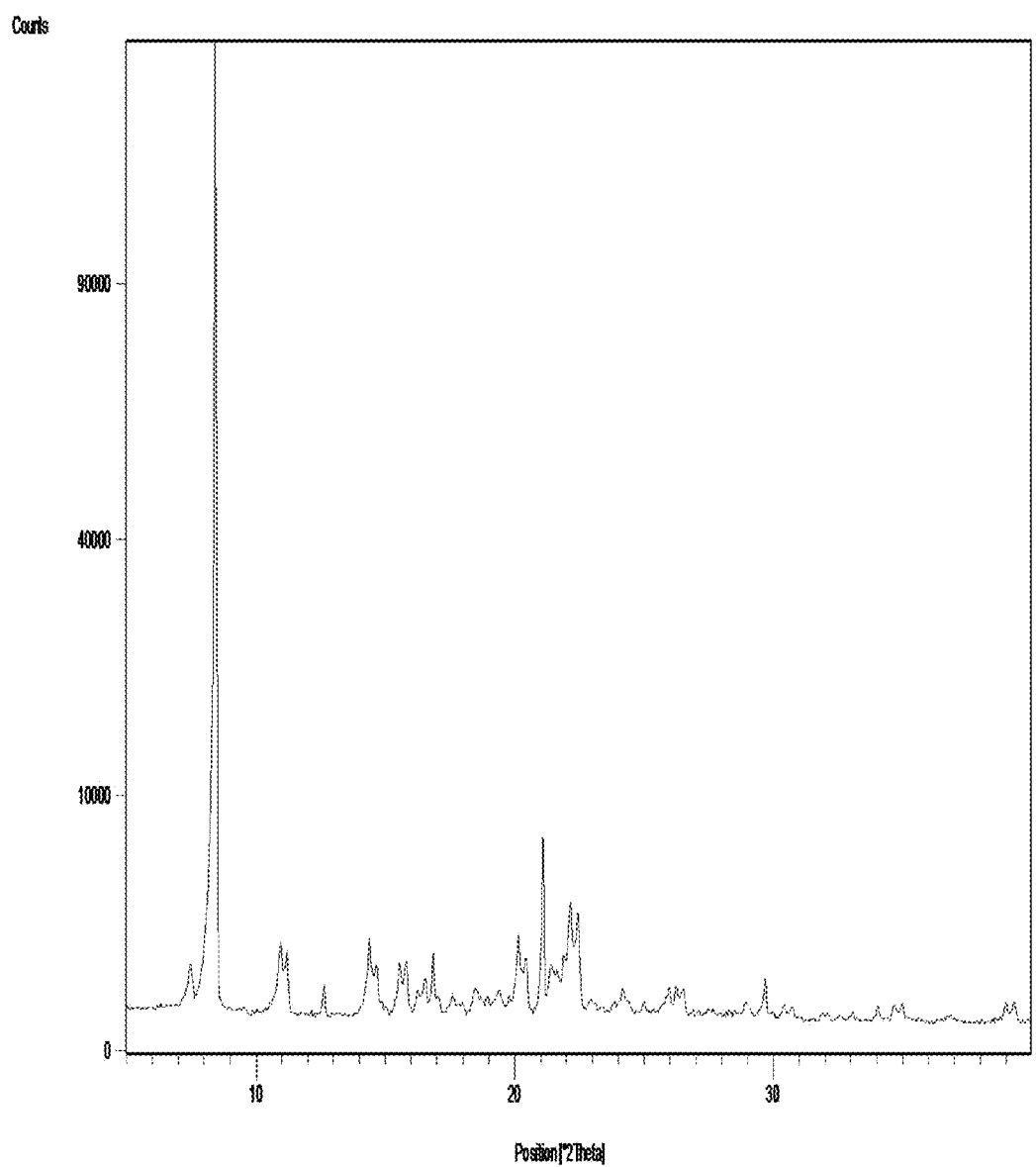
FIG. 6b: X-Ray Powder Diffraction Pattern for Form C of 3-amino-6-(4-{3-[(3-methoxypropyl)amino]propyl}phenyl)-N-pyridin-3-ylpyrazine-2-carboxamide mono-besylate.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern substantially the same as the X-ray powder diffraction pattern shown in FIG. 6b.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=11.2° plus or minus 0.1° 2-theta.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=14.7° plus or minus 0.1° 2-theta.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least one specific peak at 2-theta=15.8° plus or minus 0.1° 2-theta.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with at least two specific peaks at 2-theta=11.2°, 14.7° and 15.8° wherein said values may be plus or minus 0.1° 2-theta.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern with specific peaks at 2-theta=11.2, 12.6, 14.7, 15.5, 15.8, 16.8, 20.4, 21.1, 22.5, 26.5°, wherein said values may be plus or minus 0.1° 2-theta.

According to a further aspect of the present invention, there is provided a crystalline form, Form C of 3-amino-6-(4-{3-[(3-methoxypropyl)amino]propyl}phenyl)-N-pyridin-3-ylpyrazine-2-carboxamide mono-besylate, which has an X-ray powder diffraction pattern as shown in FIG. 6b.

As yet a further example, a particular crystalline form has been identified for the compound of Example 4.1.

Accordingly, a further aspect of the invention is Form A of 3-amino-6-(4-{3-[(3-methoxypropyl)amino]propyl}phenyl)-N-pyridin-3-ylpyrazine-2-carboxamide mono-tosylate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at about 2-theta=8.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at about 2-theta=23.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least two specific peaks at about 2-theta=8.0° and 23.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with specific peaks at about 2-theta=8.0, 11.7, 14.8, 20.0, 20.9, 21.5, 22.2, 23.0, 27.5, 28.0°.

Figure 8:
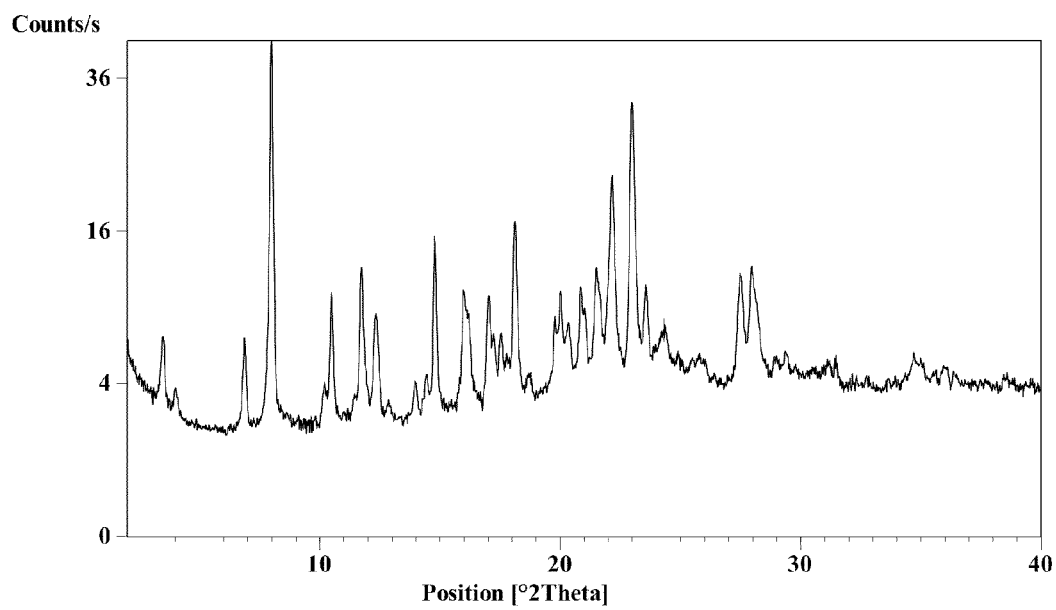
FIG. 8: X-Ray Powder Diffraction Pattern Form A of 3-amino-6-(4-{3-[(3-methoxypropyl)amino]propyl}phenyl)-N-pyridin-3-ylpyrazine-2-carboxamide mono-tosylate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern substantially the same as the X-ray powder diffraction pattern shown in FIG. 8.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at 2-theta=8.0° plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at 2-theta=23.0° plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least two specific peaks at 2-theta=8.0° and 23.0° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with specific peaks at 2-theta=8.0, 10.5, 11.7, 12.4, 14.8, 16.0, 17.0, 18.1, 20.0, 20.9, 21.5, 22.2, 23.0, 27.5, 28.0° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at 2-theta=8.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least one specific peak at 2-theta=23.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with at least two specific peaks at 2-theta=8.0° and 23.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern with specific peaks at 2-theta=8.0, 10.5, 11.7, 12.4, 14.8, 16.0, 17.0, 18.1, 20.0, 20.9, 21.5, 22.2, 23.0, 27.5, 28.0°.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-tosylate, which has an X-ray powder diffraction pattern as shown in FIG. 8.

Further examples of compounds for which particular crystalline forms have been identified are the compounds of Examples 4.2-4.4.

Accordingly, a further aspect of the invention is Form A of 3-amino-6-(4-{3-[(3-methoxypropyl)amino]propyl}phenyl)-N-pyridin-3-ylpyrazine-2-carboxamide di-esylate.

Accordingly, a further aspect of the invention is Form A of 3-amino-6-(4-{3-[(3-methoxypropyl)amino]propyl}phenyl)-N-pyridin-3-ylpyrazine-2-carboxamide mono-DL-mandelate.

Accordingly, a further aspect of the invention is Form A of 3-amino-6-(4-{3-[(3-methoxypropyl)amino]propyl}phenyl)-N-pyridin-3-ylpyrazine-2-carboxamide mono-benzoate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide di-esylate, which has an X-ray powder diffraction pattern with at least two specific peaks at 2-theta=5.2° and 12.7° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide di-esylate, which has an X-ray powder diffraction pattern with specific peaks at 2-theta=5.2, 10.4, 12.7, 15.0, 16.9, 17.3, 19.1, 19.6, 20.0, 23.5° wherein said values may be plus or minus 0.1° 2-theta.

Figure 10:
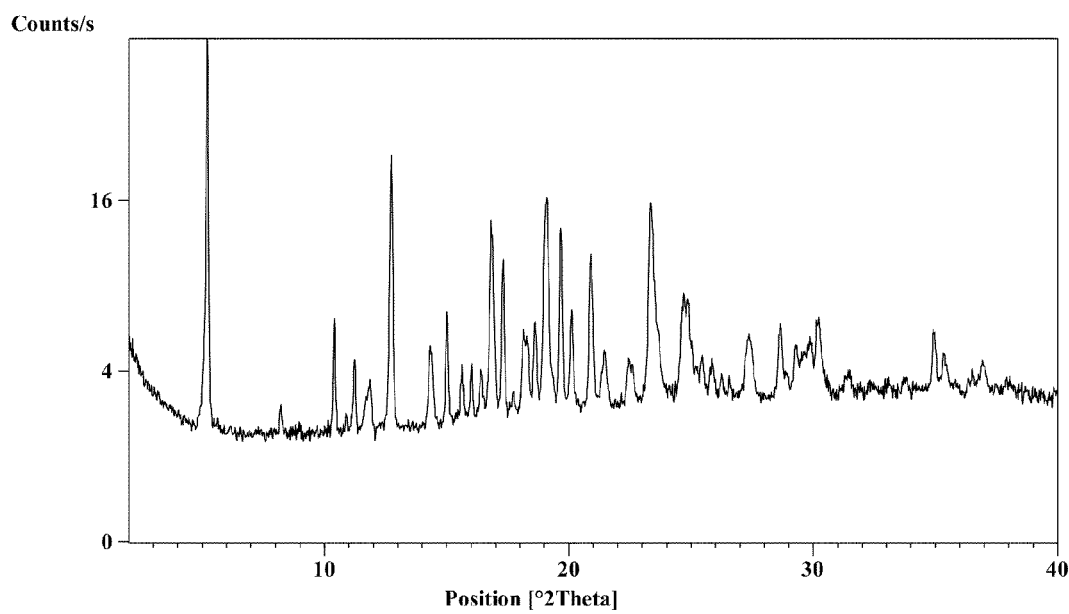
FIG. 10: X-Ray Powder Diffraction Pattern for Form A of 3-amino-6-(4-{3-[(3-methoxypropyl)amino]propyl}phenyl)-N-pyridin-3-ylpyrazine-2-carboxamide di-esylate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide di-esylate, which has an X-ray powder diffraction pattern as shown in FIG. 10.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-DL-mandelate, which has an X-ray powder diffraction pattern with at least two specific peaks at 2-theta=2.7° and 7.8° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-DL-mandelate, which has an X-ray powder diffraction pattern with specific peaks at 2-theta=2.7, 5.2, 7.8, 9.6, 10.5, 12.3, 13.1, 15.7, 18.4° wherein said values may be plus or minus 0.1° 2-theta.

Figure 12:
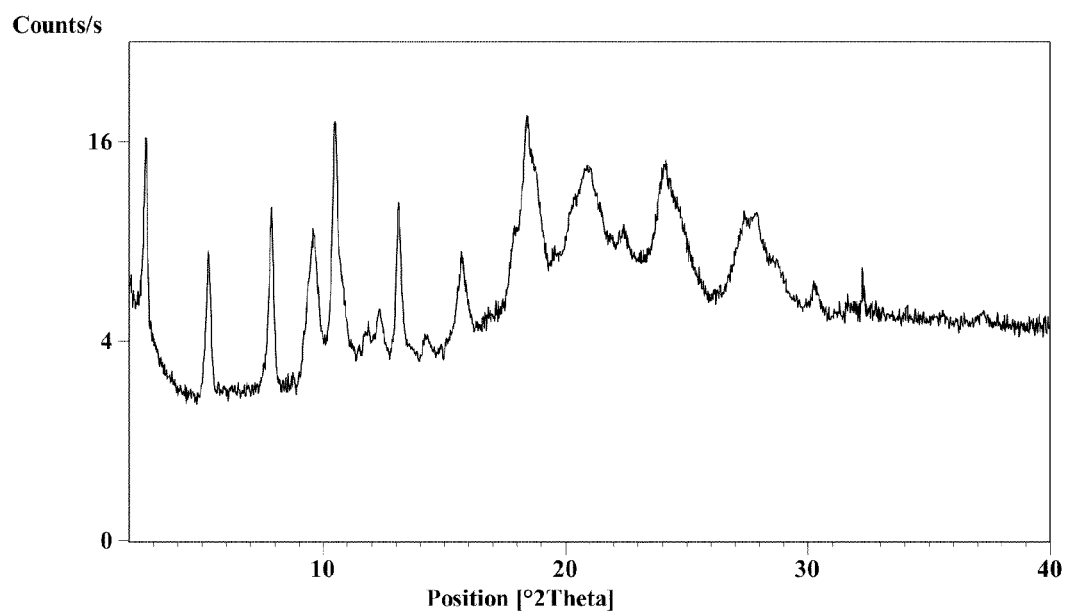
FIG. 12: X-Ray Powder Diffraction Pattern for Form A of 3-amino-6-(4-{3-[(3-methoxypropyl)amino]propyl}phenyl)-N-pyridin-3-ylpyrazine-2-carboxamide mono-DL-mandelate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-DL-mandelate, which has an X-ray powder diffraction pattern as shown in FIG. 12.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-benzoate, which has an X-ray powder diffraction pattern with at least two specific peaks at 2-theta=5.3° and 9.2° wherein said values may be plus or minus 0.1° 2-theta.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-benzoate, which has an X-ray powder diffraction pattern with specific peaks at 2-theta=5.3, 6.2, 9.2, 9.8, 11.9, 16.6, 17.8, 18.1, 19.5, 24.6° wherein said values may be plus or minus 0.1° 2-theta.

Figure 14:
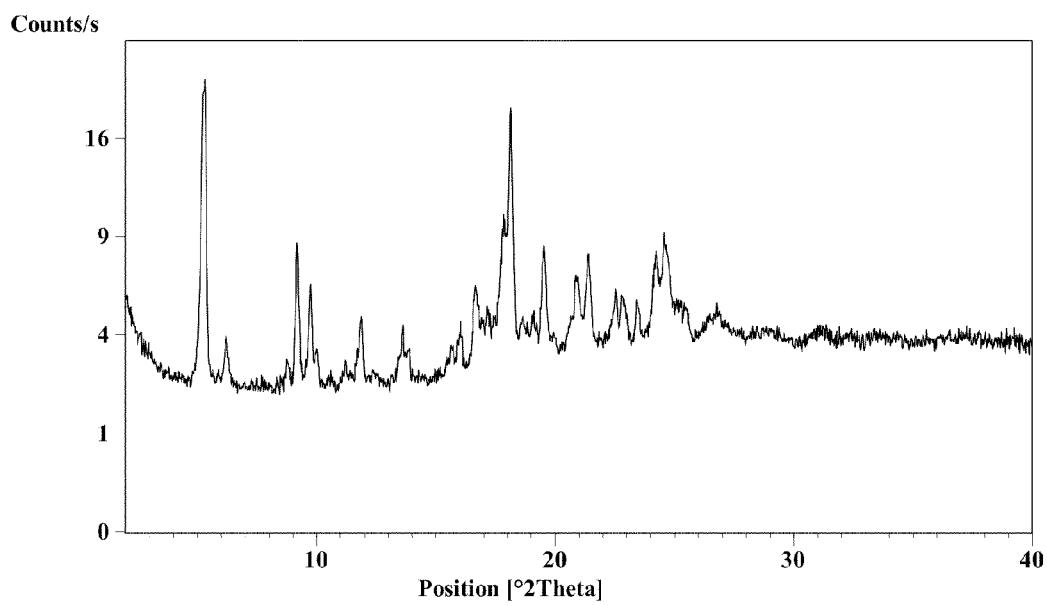
FIG. 14: X-Ray Powder Diffraction Pattern for Form A of 3-amino-6-(4-{3-[(3-methoxypropyl)amino]propyl}phenyl)-N-pyridin-3-ylpyrazine-2-carboxamide mono-benzoate.

According to a further aspect of the present invention, there is provided a crystalline form, Form A of 3-amino-6-(4-{3-[(3-methoxypropyl)amino]propyl}phenyl)-N-pyridin-3-ylpyrazine-2-carboxamide mono-benzoate, which has an X-ray powder diffraction pattern as shown in FIG. 14.

It will be understood that 2-theta values of the X-ray powder diffraction patterns may vary slightly from one machine to another or from one sample to another, and so the values quoted are not to be construed as absolute.

It is also known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the crystalline Forms of the present invention described above, unless otherwise stated, are not limited to the crystals that provide X-ray powder diffraction patterns identical to the X-ray powder diffraction pattern shown in FIGS. 4, 6a, 6b, 8, 10, 12 and 14, and any crystals providing X-ray powder diffraction patterns substantially the same as those shown in these Figures fall within the scope of the present invention. A person skilled in the art of X-ray powder diffraction is able to judge the substantial identity of X-ray powder diffraction patterns.

Persons skilled in the art of X-ray powder diffraction will also realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.1° 2-theta, and such degree of a measurement error should be taken into account when considering the X-ray powder diffraction data. Furthermore, it should be understood that intensities might fluctuate depending on experimental conditions and sample preparation (preferred orientation).

It is further to be understood that a suitable pharmaceutically-acceptable pro-drug of a compound of the Formula I also forms an aspect of the present invention. Accordingly, the compound of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable amide derivatives that may be formed at an amino group in a compound of the Formula I.

Accordingly, the present invention includes a compound of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

It is to be understood that, insofar as a pharmaceutically-acceptable pro-drug of a compound of the Formula I defined above may exist in optically active or racemic forms by virtue of one or more asymmetric carbon atoms, the invention includes in its definition any such optically active or racemic form. The synthesis of optically active forms may be carried out by standard techniques of organic chemistry well known in the art, for example by synthesis from optically active starting materials or by resolution of a racemic form.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of the compound of the Formula I that possesses an amino group is, for example, an in vivo cleavable amide derivative thereof. Suitable pharmaceutically-acceptable amides from an amino group include, for example an amide formed with (1-10C) alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Particular compounds of the invention are each of the Examples and pharmaceutically-acceptable salt(s) thereof, each of which provides a further independent aspect of the invention.

According to a further aspect of the invention there is provided a pyrazine derivative of the Formula I or a pharmaceutically-acceptable salt thereof, which is obtainable by following any of the Examples as disclosed herein.

A further feature of the invention is any of the scopes defined herein with the proviso that specific Examples, such as Example 1, 2, 3a, 3b, 4.1 etc. are individually disclaimed.

A yet further feature of the invention is any of the scopes defined herein with the proviso that one specific Example, such as Example 1, 2, 3a, 3b, 4.1 etc. is individually disclaimed.

is Particular novel compounds of the invention include, for example, pyrazine derivatives of the Formula I, or pharmaceutically-acceptable salts thereof, wherein, each of n, m and R has any of the meanings defined hereinbefore or in paragraphs (a) to (h) hereinafter:—
(a) n is 2;
(b) n is 3;
(c) m is 2;
(d) m is 3;
(e) n is 3 and m is 3;
(f) n is 3 and m is 2;
(g) n is 2 and m is 3; or
(h) R is methyl.

A particular group of compounds of the invention are pyrazine derivatives of Formula I above wherein:—
n is 2 or 3;
m is 3;
R is methyl or ethyl, conveniently methyl; or a pharmaceutically-acceptable salt thereof.

A particular group of compounds of the invention are pyrazine derivatives of Formula I above wherein:—
n is 3;
m is 2 or 3;
R is methyl or ethyl, conveniently methyl; or a pharmaceutically-acceptable salt thereof.

A particular compound of the invention is a pyrazine derivative of the Formula I selected from any one of the following:—
3-amino-6-(4-{3-[(3-methoxypropyl)amino]propyl}phenyl)-N-pyridin-3-ylpyrazine-2-carboxamide;
3-amino-6-(4-{2-[(2-methoxyethyl)amino]ethyl}phenyl)-N-pyridin-3-ylpyrazine-2-carboxamide;
3-amino-6-(4-{2-[(3-methoxypropyl)amino]ethyl}phenyl)-N-pyridin-3-ylpyrazine-2-carboxamide; and
3-amino-6-(4-{3-[(2-methoxyethyl)amino]propyl}phenyl)-N-pyridin-3-ylpyrazine-2-carboxamide; or a pharmaceutically-acceptable salt thereof.

According to a yet further aspect of the invention, a particular compound of the invention is a pyrazine derivative of the Formula I selected from any one of the following:—
3-amino-6-(4-{3-[(3-methoxypropyl)amino]propyl}phenyl)-N-pyridin-3-ylpyrazine-2-carboxamide;
3-amino-6-(4-{2-[(3-methoxypropyl)amino]ethyl}phenyl)-N-pyridin-3-ylpyrazine-2-carboxamide; and
3-amino-6-(4-{3-[(2-methoxyethyl)amino]propyl}phenyl)-N-pyridin-3-ylpyrazine-2-carboxamide; or a pharmaceutically-acceptable salt thereof.

Another aspect of the present invention provides a process for preparing a compound of the Formula I, or a pharmaceutically-acceptable salt thereof. A suitable process is illustrated by the following representative process variants in which, unless otherwise stated, n, m and R have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated, which are within the ordinary skill of an organic chemist.

Suitable process variants include, for example, the following:—

(a) An amine displacement reaction of a compound of the Formula II:

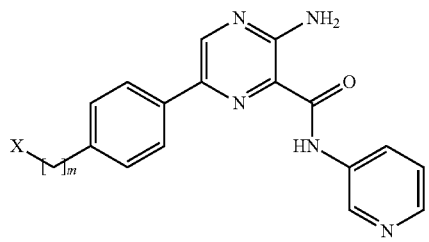

or a reactive derivative thereof, wherein m is 2 or 3 and X represents a suitable leaving group such as for example a halogen (such as bromo, fluoro, chloro or iodo), or a sulphonate group such as for example methane sulphonate or trifluoromethane sulphonate, wherein any functional group present is protected if necessary, with an amine compound of the Formula III:

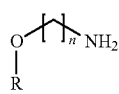

wherein n is 2 or 3 and R is methyl or ethyl, to form a compound of the Formula I, whereafter any protecting group that is present is removed.

The reaction is conveniently carried out in the presence of an organic solvent such as dichloromethane, N,N-dimethylformamide, dimethyl sulphoxide or acetonitrile in the presence of a suitable base such as for example an alkali metal carbonate (such as for example sodium carbonate or potassium carbonate) or an alkaline earth metal carbonate (such as for example calcium carbonate), a metal hydroxide (such as for example sodium hydroxide or potassium hydroxide) at a temperature, for example, in the range from 0 to 150° C., conveniently at a temperature range of between 80 and 90° C.

Compounds of the Formula II, including reactive derivatives may, for example, be prepared by the reaction of a compound of the Formula IV:

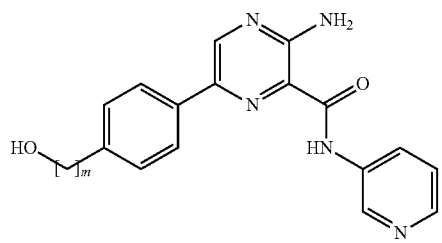

wherein m is 2 or 3, with a suitable activating reagent such as for example, methanesulphonyl chloride, toluensulphonyl chloride, thionyl chloride or oxalyl chloride. The reaction may conveniently be carried out in an organic solvent such as tetrahydrofuran or dichloromethane using either an inorganic base such as sodium carbonate or potassium carbonate, or an organic base such as triethyl amine or diisopropylethylamine at a temperature in the range from 0 to 150° C., conveniently at ambient temperature.

Compounds of the Formula IV, may for example, be prepared by the reaction of a compound of the Formula V:

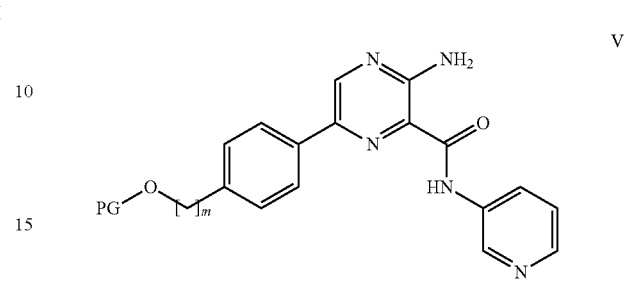

wherein m is 2 or 3 and PG represents a protecting group such as tert-butyldimethylsilyl or tetrahydropyrane with a suitable acid such as for example sulphuric acid.

The reaction may conveniently be carried out in an organic solvent such as methanol, tetrahydrofuran or dioxane using either an inorganic acid such as hydrochloric acid or hydrobromic acid, or an organic acid such as trifluoroacetic acid at a temperature, for example, in the range from 0 to 150° C., conveniently at a temperature range of between 20 and 80° C.

Compounds of the Formula V may, for example, be prepared by a metal catalysed coupling reaction of a compound of the Formula VI:

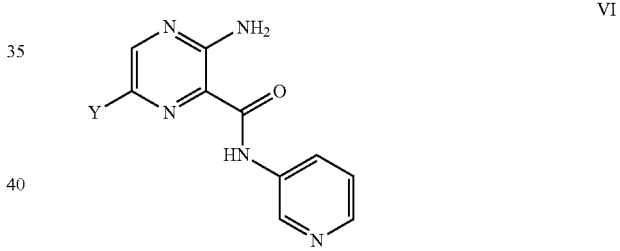

wherein Y represents a suitable leaving group such as for example a halogen (such as chloro, fluoro, bromo or iodo), or trifluoromethanesulphonate, with a compound of the Formula VII:

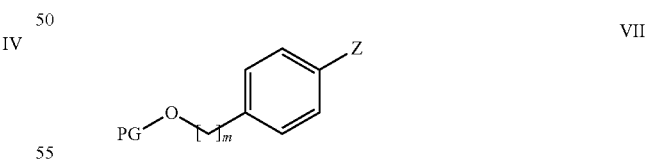

wherein m is 2 or 3, Z represents a suitable leaving group such as for example a halogen (such as chloro, fluoro, bromo or iodo) or trifluoromethanesulphonate and PG represents a protecting group such as tert-butyldimethylsilyl or tetrahydropyrane.

The reaction may conveniently be carried out in an organic solvent such as tetrahydrofuran, N,N-dimethylformamide, or dioxane in the presence of a Pd catalyst with a suitable ligand such as Pd(dppf)Cl$_2$ or Pd(PPh$_3$)$_3$ and in the presence of a diborane with a suitable ligand such as bis(pinacolato)diboron or bis(catecholato)diboron and in a presence of a salt such as potassium acetate or sodium acetate at a temperature in the range from 0 to 150° C., conveniently at a temperature range between 80 and 90° C.

Alternatively, compounds of the Formula IV, may for example, be prepared by the reaction of a compound of the Formula VI with a compound of the Formula VIII:

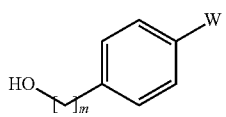

VIII wherein m is 2 or 3 and W represents a boronic acid or boronic acid ester such as for example pinacole boronate or catechol boronate.

The reaction may conveniently be carried out in an organic solvent such as tetrahydrofuran, N,N-dimethylformamide, or dioxane in the presence of a Pd catalyst with a suitable ligand such as Pd(dppf)Cl$_2$ or Pd(PPh$_3$)$_3$ and in the presence of a salt such as potassium acetate or sodium acetate at a temperature in the range from 0 to 150° C., conveniently at a temperature range between 70 and 90° C.

Compounds of the Formula IV could also be prepared using an inverse coupling process to that described above, wherein the compound of Formula VI would have a W group (which is a boronic acid or boronic acid ester such as for example pinacole boronate or catechol boronate as defined hereinbefore) in place of the Y group and the compound of Formula VIII would have a Y group (being a suitable leaving group such as for example a halogen (such as chloro, fluoro, bromo or iodo), or trifluoromethanesulphonate as defined hereinbefore) present in place of the W group. Suitable conditions for the reaction would be those described above.

Compounds of the Formula VIII may, for example, be prepared by treatment of a compound of the Formula IX:

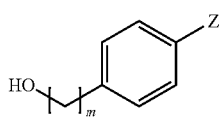

IX wherein m is 2 or 3 and Z represents a suitable leaving group such as for example a halogen or trifluoromethane sulphonate, with a suitable diborane complex such as for example, bis(pinacolato)diboron or bis(catecholato)diboron. The reaction may conveniently be carried out in an organic solvent such as tetrahydrofuran, N,N-dimethylformamide, acetonitrile or dioxane in the presence of a Pd catalyst such as Pd—Cl$_2$ or Pd(OAc)$_2$ with a ligand such as PCy$_3$ or PPh$_3$ and in the presence of a salt such as potassium acetate or sodium acetate at a temperature in the range from 0 to 150° C., conveniently at a temperature range between 70 and 90° C.

Compounds of the Formula VII, may, for example, be prepared by treatment of a compound of the Formula IX:

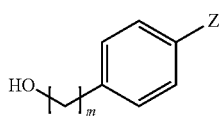

IX wherein m is 2 or 3 and Z represents a suitable leaving group such as for example a halogen or trifluoromethane sulphonate, with a suitable protecting agent such as for example tert-butyldimethylsilyl chloride. The reaction is conveniently conducted in the presence of an organic solvent such as tetrahydrofuran or dichloromethane using either an inorganic base such as sodium carbonate or potassium carbonate, or an organic base such as triethyl amine or diisopropylethylamine and in the presence of a suitable catalyst such as 4-dimethylaminopyridine at a temperature in the range from 0 to 150° C., conveniently at ambient temperature.

Alternatively, the above reaction can be conducted with dihydropyran in an organic solvent such as THF or if no solvent is presents with a catalyst such as sulphuric acid or HCl at a temperature in the range from 0 to 150° C., conveniently at refluxing conditions.

Compounds of the Formulae III, VI and IX may be obtained by conventional procedures or are commercially available, known in the literature, or they can be prepared by using or adapting standard processes known in the art;

(b) A reaction of a compound of the Formula X:

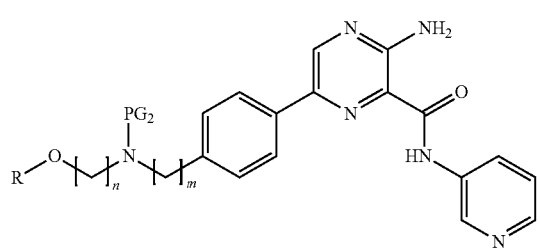

X wherein, n is 2 or 3, m is 2 or 3, R is methyl or ethyl and PG$_2$ represents a suitable protecting group such as for example an alkoxylcarbonyl (such as t-butoxycarbonyl or isopropoxycarbonyl), with a suitable acid such as for example HCl or trifluoroacetic acid.

The reaction may conveniently carried out in an organic solvent such as EtOAc, methanol, 2-methyltetrahydrofuran or tetrahydrofuran, or an inorganic solvent such as for example water using either an inorganic acid such as hydrochloric acid or hydrobromic acid, or an organic acid such as trifluoroacetic acid at a temperature, for example, in the range from 0 to 150° C., conveniently at a temperature range of between 20 and 80° C.

Compounds of the Formula X may, for example, be prepared by a metal catalysed coupling reaction of a compound of the Formula XI:

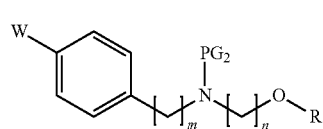

XI wherein, n is 2 or 3, m is 2 or 3, R is methyl or ethyl, PG$_2$ represents a suitable protecting group such as for example an alkoxylcarbonyl (such as t-butoxycarbonyl or isopropoxycarbonyl), and W represents a boronic acid or a boronic acid ester such as for example pinacole boronate or catechol boronate, with a compound of the Formula VI.

The reaction may conveniently be carried out in an organic solvent such as tetrahydrofuran, N,N-dimethylformamide, dioxane or 1-butanol in the presence of a Pd catalyst with a suitable ligand such as Pd(dppf)Cl$_2$ or Pd(PPh$_3$)$_3$, or alternatively a mixture with sodiumtetrachloropalladate and 3-(di-tert-butylphosphonium)propane sulphate, and in the presence of a salt such as potassium acetate, sodium acetate or potassium phosphate tribasic N-hydrate at a temperature in the range from 0 to 150° C., conveniently at a temperature range between 70 and 90° C.

Compounds of the Formula XI may, for example, be prepared by the reaction of a compound of the Formula XII:

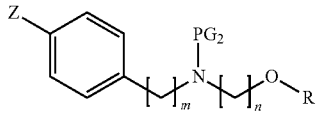

XII wherein, n is 2 or 3, m is 2 or 3, R is methyl or ethyl, PG$_2$ represents a suitable protecting group such as for example an alkoxylcarbonyl (such as t-butoxycarbonyl or isopropoxycarbonyl) and Z represents a suitable leaving group such as for example a halogen or trifluoromethane sulphonate with a suitable diborane complex such as for example, bis(pinacolato)diboron or bis(catecholato)diboron. The reaction may conveniently be carried out in an organic solvent such as tetrahydrofuran, N,N-dimethylformamide, acetonitrile or dioxane in the presence of a Pd catalyst such as Pd—Cl$_2$ or Pd(OAc)$_2$ with a ligand such as PCy$_3$ or PPh$_3$ and in the presence of a salt such as potassium acetate or sodium acetate at a temperature in the range from 0 to 150° C., conveniently at a temperature range between 70 and 90° C.

Compounds of the Formula XII may, for example, be prepared by the reaction of a compound of the Formula XIII:

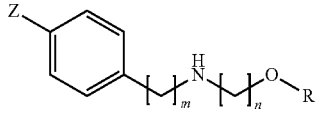

XIII wherein, n is 2 or 3, m is 2 or 3, R is methyl or ethyl, and Z represents a suitable leaving group such as for example a halogen or trifluoromethane sulphonate with a suitable protecting agent such as for example Di-tert-butyl dicarbonate. The reaction may conveniently be carried out in an organic solvent such as methanol, tetrahydrofuran or dioxane using either an inorganic acid such as hydrochloric acid or hydrobromic acid, or an organic acid such as trifluoroacetic acid at a temperature, for example, in the range from 0 to 150° C., conveniently at a temperature range of between 20 and 80° C.

Compounds of the Formula XIII may, for example, be prepared by the reaction of a compound of the Formula XIV:

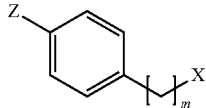

XIV or a reactive derivative thereof, wherein m is 2 or 3, X represents a suitable leaving group such as for example a halogen (such as bromo, fluoro, chloro or iodo), or a sulphonate group such as for example methane sulphonate or trifluoromethane sulphonate and Z represents a suitable leaving group such as for example a halogen or trifluoromethane sulphonate with a suitable protecting agent such as for example Di-tert-butyl dicarbonate, with an amine compound of the Formula III.

The reaction may conveniently be carried out in the presence of an organic solvent such as dichloromethane, N,N-dimethylformamide, dimethyl sulphoxide or acetonitrile in the presence of a suitable base such as for example an alkali metal carbonate (such as for example sodium carbonate or potassium carbonate) or an alkaline earth metal carbonate (such as for example calcium carbonate), a metal hydroxide (such as for example sodium hydroxide or potassium hydroxide) at a temperature, for example, in the range from 0 to 150° C., conveniently at a temperature range of between 80 and 90° C.

Compounds of the Formula XIV may, for example, be prepared by the reaction of a compound of the Formula IX, with a suitable activating reagent such as for example, methanesulphonyl chloride, toluensulphonyl chloride, thionyl chloride or oxalyl chloride. The reaction may conveniently be carried out in an organic solvent such as tetrahydrofuran or dichloromethane using either an inorganic base such as sodium carbonate or potassium carbonate, or an organic base such as triethyl amine or diisopropylethylamine at a temperature in the range from 0 to 150° C., conveniently at ambient temperature.

When a pharmaceutically-acceptable salt of a pyrazine derivative of the Formula I is required, for example an acid-addition salt, it may be obtained by, for example, reaction of said pyrazine derivative with a suitable acid.

When a pharmaceutically-acceptable pro-drug of a pyrazine derivative of the Formula I is required, it may be obtained using a conventional procedure. For example, an in vivo cleavable amide of a pyrazine derivative of the Formula I may be obtained by, for example, reaction of a compound of the Formula I containing an amino group with a pharmaceutically-acceptable carboxylic acid.

It will also be appreciated by the person skilled in the organic synthetic arts that certain of the ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents, acylation of substituents, amidation of substituents and oxidation of substituents. The reagents and reaction conditions for such procedures are well known in the chemical art. Particular examples of aromatic substitution reactions include the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

It will also be appreciated that, in some of the reactions mentioned hereinbefore, it may be necessary or desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group, which may be removed by treatment with an alkylamine, for example dimethylaminopropylamine, or with hydrazine.

The protecting groups may be removed at any convenient stage in the synthesis using conventional techniques well known in the chemical art.

Certain of the intermediates defined herein are novel and these are provided as a further feature of the invention. For example, compounds of the Formula II and V (as defined hereinabove) may be useful as intermediates in the preparation of the compound of the invention.

Furthermore, the following compounds may be useful as intermediates in the preparation of the compound of the invention:
3-amino-6-(4-(3-(tert-butyldimethylsilyloxy)propyl)phenyl)-N-(pyridin-3-yl)-pyrazine-2-carboxamide; and
3-(4-(5-Amino-6-(pyridin-3-ylcarbamoyl)pyrazin-2-yl)phenyl)propyl methanesulfonate.

Biological Assays

The following assays can be used to measure the effects of the compounds of the present invention:

In Vitro GSKβ Kinase Assay

This biochemical assay used a Fluorescence Resonance Energy Transfer (FRET)-based, coupled-enzyme format to determine the ability of test compounds to inhibit substrate phosphorylation by recombinant GSK3β serine/threonine kinase (Kleman-Leyer, K. et al. Drug Disc. Devel. 2003, 6:81-2). The substrate used in this assay was Z'-LYTE™ ser/Thr 9 peptide and the FRET assay kit was obtained from Invitrogen (Paisley, UK, catalogue number PV3324). N-terminal His6-tagged recombinant human GSK313, with an H350L mutation, was expressed in baculovirus in Sf21 insect cells, purified and obtained from Millipore (Billerica, Mass., USA, catalogue number 14-306 Human).

Test compounds were prepared as 10 mM stock solutions in dimethylsulphoxide (DMSO) and diluted in DMSO as required. Aliquots (2.5 µl) of compound dilutions were added to the wells of an Optiplate-F PerkinElmer 384-well plate (Massachusetts, USA, catalogue number 6007270). Control wells that produced a maximum signal corresponding to maximum enzyme activity were created by using 100% phosphorylated peptide obtained from Invitrogen (Paisley, UK, catalogue number PV3326). A 5 µl aliquot of 100% phosphorylated peptide (100 µM in 1.33× kinase buffer) was added to all maximum control wells. 2.5 µl of 4% DMSO solution (v/v) in 1.33× kinase buffer was added to maximum control wells. Control wells that produced a minimum signal corresponding to 100% inhibited enzyme were created by adding 2.5 µl of 40 µM Staurosporine in 1.33× kinase buffer containing 4% DMSO (v/v). A 5 µl mixture of GSK3β (100 ng/µl) enzyme and non-phosphorylated substrate (Z-LYTE™ ser/Thr 9 peptide, 100 µM) in a 1.33× kinase buffer solution was added to each well except maximum control wells and the assay plate centrifuged at 270 g for 1 minute. The kinase buffer used 1.33× was obtained from Invitrogen (Paisley, UK, catalogue number PV3189) and contained 67 mM HEPES (pH 7.5), 13 mM $MgCl_2$, 1.3 mM EGTA, 0.01% BRIJ-35. Then 2.5 µl adenosine triphosphate (28 µM) in kinase buffer was added per well, centrifuged at 270 g for 1 minute and then the assay plate was shaken for 1 hour at room temperature. A proprietary development solution was prepared by adding 58 µl of development reagent A (Invitrogen, Paisley, UK, catalogue number PV3297) to 2142 µl of development reagent B (Invitrogen, Paisley, UK, catalogue number P3127). Then 5 µl of Invitrogen proprietary development solution was added per well, centrifuged at 270 g for 1 minute and then shaken for 1 hour at room temperature. The reaction was stopped by addition of 5 µl of a stop reagent per well (Invitrogen, Paisley, UK catalogue number P3094), centrifuged at 270 g for 1 minute and then shaken for 5 minutes at room temperature.

The resultant signals arising from laser light excitation at 400 nM were read using a Perkin Elmer Envision spectrophotometer (Perkin Elmer, Massachusetts, USA). The Z'-LYTE™ biochemical assay employs a FRET-based, coupled-enzyme format and is based on the differential sensitivity of phosphorylated and non-phosphorylated peptides to proteolytic cleavage. A ratiometric method, which calculates the ratio (the Emission Ratio) of donor emission to acceptor emission after excitation of the donor fluorophore at 400 nm, quantitates reaction progress, as shown in the equation below.

$$\text{Emission Ratio} = \text{Coumarin Emission (445 nm)} \div \text{Fluoresein Emission (520 nm)}$$

The mean data values for each test compound concentration, 100% DMSO control wells and 100% inhibition control wells were used to generate a concentration response curve from which the percentage inhibition of kinase activity with compound treatment was calculated and a potency ($IC_{50}$) value calculated. The $IC_{50}$ value is the concentration of test compound that inhibited 50% of human GSK3β kinase activity. The final ATP concentration in this assay was (b) Cellular Beta-Catenin Stabilisation Assay This assay uses an imaging based approach to measure the ability of test compounds to promote Beta-catenin stabilisation in the nucleus of C3H10T1/2 cells. Beta-catenin stabilisation is an indicator of GSK3β inhibition.

A C3H10T1/2 mouse clone 8 fibroblast cell line (American Type Culture Collection (ATCC, USA; catalogue number CRL 226) was routinely maintained at 37° C. with 5% $CO_2$ in Basal Medium Eagle (BME, Invitrogen; Paisley, UK; catalogue number 41010) containing 10% (v/v) foetal bovine serum (FBS, Invitrogen, Paisley; UK; catalogue number 10270) and 2 mM L-glutamine (Invitrogen, Paisley, UK; catalogue number 25030024). For the assay, the cells were detached from the culture flask with 'Accutase' (Innovative Cell Technologies Inc., San Diego, USA; catalogue number AT104) using standard tissue culture methods and re-suspended in assay media comprising of BME containing 5% (v/v) FBS and 2 mM L-glutamine to give 55,555 cells per ml. Then, 90 µl of this solution was seeded into each well of a clear-bottom 96 well tissue culture plate (Perkin Elmer Viewplate; catalogue number 6005182) using a Multidrop Combi Dispenser (Thermo Fisher Scientific, Loughborough, UK) to give 5,000 cells per well. Plates were incubated overnight at 37° C. with 5% $CO_2$ to allow the cells to adhere to the wells. Test compounds were prepared as 10 mM stock solutions in dimethylsulphoxide (DMSO) (Sigma-Aldrich; Poole, UK, catalogue number 49442-9) and serially diluted in DMSO. A Multidrop Combi was used to dispense 245 µl of pre-warmed assay media into a 96 well plate (Thermo Fisher Scientific, Loughborough, UK; catalogue number 50823925) before 5 µl of serially diluted compound was added to this intermediate plate. After mixing, 10 µl of each compound concentration was added to the cell plates. The total dilution factor from DMSO stock was 500 times. Control cells received either DMSO (0.2% v/v final concentration) or 10 µM positive control compound. The cells were incubated for 24 hours at 37° C. with 5% $CO_2$.

After compound treatment the cells were fixed by the addition of 100 µl of 8% w/v paraformaldehyde (Sigma-Aldrich, Poole, UK; catalogue number P6148), directly into the assay plate wells. The cells were incubated at ambient temperature with fixative for 30 minutes before washing 3 times with 100 µl phosphate-buffered saline (PBS, Sigma-Aldrich; catalogue number D8537). The cells were then washed once and incubated at room temperature in blocking solution (PBS containing 1.1% w/v Bovine Serum Albumin (BSA, Sigma-Aldrich, Poole, UK; catalogue number A7906) and 0.2% v/v Triton X-100 (Sigma-Aldrich, Poole, UK; catalogue number X100)) for 1 hour. After removing the blocking solution, 30 µl of anti beta-catenin antibody (BD Biosciences; catalogue number 610154) at a concentration of 1.25 µg/ml diluted in blocking solution, was added to the cells and incubated at 4° C. for 16 hours. The cells were then washed twice in 1000 blocking solution and incubated at ambient temperature for 1 hour. The cells were then placed in 400 of a secondary antibody solution comprising of AF647 donkey anti-mouse antibody (Invitrogen, Paisley, UK; catalogue number A31571) and Hoechst 33342 (Invitrogen, Paisley, UK; catalogue number H1399) nuclear counterstain at concentrations of 4 µg/ml and 1 µM respectively diluted in blocking solution. Incubation with the secondary staining solution was for 2 hours at room temperature. The cells were then washed 3 times in 100 µl of PBS before the plates were sealed ready for image capture. Fluorescent images were captured and quantified using the Incell Analyser 3000 (GE Healthcare, USA). Hoechst nuclear staining was visualised using an excitation wavelength of 365 nm along with a neutral density filter setting of 1 and a 450-65 emission filter. Beta-catenin localisation was captured using a 633 nm laser wavelength, a neutral density filter of 1 and an emission filter of 695-55 nm. To enable a sufficient cell count, 4 images per well were taken. Image data was analysed using the Nuclear Trafficking Analysis Module, TRF2. Data from each well on an assay plate was normalised to the median values of the negative and positive controls from the same assay plate and percentage effect expressed as a proportion of the positive control. Data from wells where the total cell number fell below 50% of the experimental batch median was excluded from analysis. Concentration response curves were fitted to the following form of the Hill equation (Neubig et al., 2003, *Pharmacol Rev.* 2003; 55:597-606)

$$y = A + ((B-A) \div (1 + ((C \div x)^{\hat{}} D)))$$

Where x=compound concentration (M) and y=% Effect. Also where A=basal of concentration effect curve, B=asymptote curve, C=midpoint of curve, D=slope Data for each test compound was reported as the compound concentration that results in half of the maximal effect ($EC_{50}$) and as the maximum percentage effect.

The pharmacological properties of the compound of the Formula I may be demonstrated at the following concentrations or doses in one or more of the above tests (a) and (b):
Test (a):—$IC_{50}$ versus human GSK3β enzyme in the range, for example, 10 nM-1 µM
Test (b):—$EC_{50}$ versus cellular β-catenin accumulation in murine C3H/10T1/2 cells, in the range, for example, 50 nM-5 µM.

For example, the pyrazine compound disclosed as Example 1 possesses activity in Test (a) with an $IC_{50}$ versus human GSK3β enzyme of approximately 35 nM; and activity in Test (b) with an $EC_{50}$ versus cellular β-catenin accumulation in the nucleus of murine C3H/10T1/2 cells of approximately 242 nM.

The pyrazine compound disclosed as Example 5 possesses activity in Test (a) with an $IC_{50}$ versus human GSK3β enzyme of approximately 21 nM; and activity in Test (b) with an $EC_{50}$ versus cellular β-catenin accumulation in the nucleus of murine C3H/10T1/2 cells of approximately 902 nM.

The pyrazine compound disclosed as Example 6 possesses activity in Test (a) with an $IC_{50}$ versus human GSK3β enzyme of approximately 48 nM; and activity in Test (b) with an $EC_{50}$ versus cellular β-catenin accumulation in the nucleus of murine C3H/10T1/2 cells of approximately 902 nM.

The pyrazine compound disclosed as Example 7 possesses activity in Test (a) with an $IC_{50}$ versus human GSK3β enzyme of approximately 80 nM; and activity in Test (b) with an $EC_{50}$ versus cellular β-catenin accumulation in the nucleus of murine C3H/10T1/2 cells of approximately 3890 nM.

Conveniently, particular compounds of the invention possess activity at the following concentrations or doses in the above tests (a) and (b):—
Test (a):—mean $IC_{50}$ versus human GSK3β enzyme in the range, for example, 5 nM-40 nM
Test (b):—mean $EC_{50}$ versus cellular β-catenin accumulation in murine C3H/10T1/2 cells, in the range, for example, 50 nM-300 nM.

For example, the pyrazine compound disclosed as Example 1 possesses activity in Test (a) with an $IC_{50}$ versus human GSK3β enzyme of approximately 35 nM; and activity in Test (b) with an $EC_{50}$ versus cellular β-catenin accumulation in the nucleus of murine C3H/10T1/2 cells of approximately 242 nM.

c) Osteogenic Differentiation and Assessment of Mineralisation In Vitro

Materials and Methods

For in vitro osteogenesis, human adipose-derived stem cells (hADSC) (Invitrogen, UK; catalogue number R7788-115) were seeded into 12-well plates at a density of 5000 cells/cm² and were cultured in a basal media of phenol red-free Dulbecco's Modified Eagles Medium (DMEM; Sigma-Aldrich, UK; catalogue number D1145) supplemented with 5% fetal bovine serum (FBS, Gibco, UK; catalogue number 10270) and 2 mM GlutaMax® (Gibco; catalogue number 35050). After overnight incubation, basal media was replaced and 3-amino-6-(4-{3-[(3-methoxypropyl)amino]propyl}phenyl)-N-pyridin-3-ylpyrazine-2-carboxamide trihydrochloride (solubilised in 100% DMSO and diluted in cell culture media to a final concentration of 0.2% DMSO) was added. In osteogenic positive control wells, basal media was replaced with a differentiation media; phenol red-free DMEM supplemented with 5% FBS, 2 mM GlutaMax®, 50 µg/ml L-ascorbic acid (Sigma-Aldrich; Catalogue no. A8960), 5 mM β-glycerophosphate (Calbiochem, UK; catalogue number 35675), and 10 nM dexamethasone (Sigma-Aldrich; catalogue number D4902). The cultures were incubated at 37° C. in 5% $CO_2$ with media and compound was replaced every 3-4 days over a time-course of 24 days.

The formation of mineralized bone nodules was assessed during the time-course using Alizarin Red S staining. At numerous times throughout the time-course, cells were fixed with 4% paraformaldehyde (Sigma-Aldrich; catalogue number P6148) for 20 min, followed by three washes with phosphate buffered saline (PBS), without calcium chloride and magnesium chloride, (Sigma-Aldrich; catalogue number D8537), before being stained with 40 mM Alizarin Red S (Sigma-Aldrich; catalogue number A5533) (pH4.2) for 20 min at room temperature. Plates were placed on a rocking platform (50 rpm) during staining After staining, cells were washed three times with PBS, and three times with water. Cells were imaged using a Leica M165FC stereomicroscope and associated Leica Application Suite imaging software (Leica Microsystems, UK).

The amount of mineralisation was quantified through the extraction of the Alizarin Red S stain from bone nodules using a cetylpyridinium chloride extraction method, previously described (Gregory et al., Analytical Biochemistry, 2004, 329: 77-84; Hwang et al., Stem Cells and Development 17: 963-970, 2008). Briefly, Alizarin Red S stain was extracted from bone nodules through the addition of 1 ml, to each well, of a cetylpyridium chloride buffer consisting of 10% cetylpyridium chloride (Sigma-Aldrich; catalogue number C0732) in 10 mM $Na_3PO_4$ (Sigma-Aldrich; catalogue number 342483) (pH7.0) and incubation for 1 h at 37° C. Following incubation, 200 μl aliquots were transferred to 96-well format and the absorbance at 550 nm was determined using a microplate spectrophotometer (SpectraMax Plus, Molecular Devices, USA). Data were expressed as mean absorbance at 550 nm±Standard error of mean (SEM). Differences between groups were examined for statistical significance using one-way analysis of variance (ANOVA) followed by Tukey's multiple comparison post hoc test. $P<0.05$ was considered significant.

FIG. 1A: Images showing Alizarin red S staining of mineralised bone nodules in response to 300 nM 3-amino-6-(4-{3-[(3-methoxypropyl)amino]propyl}phenyl)-N-pyridin-3-ylpyrazine-2-carboxamide tri-hydrochloride compared with vehicle after 24 days of cell culture. Experiments were performed in triplicate.

Figure 1B:
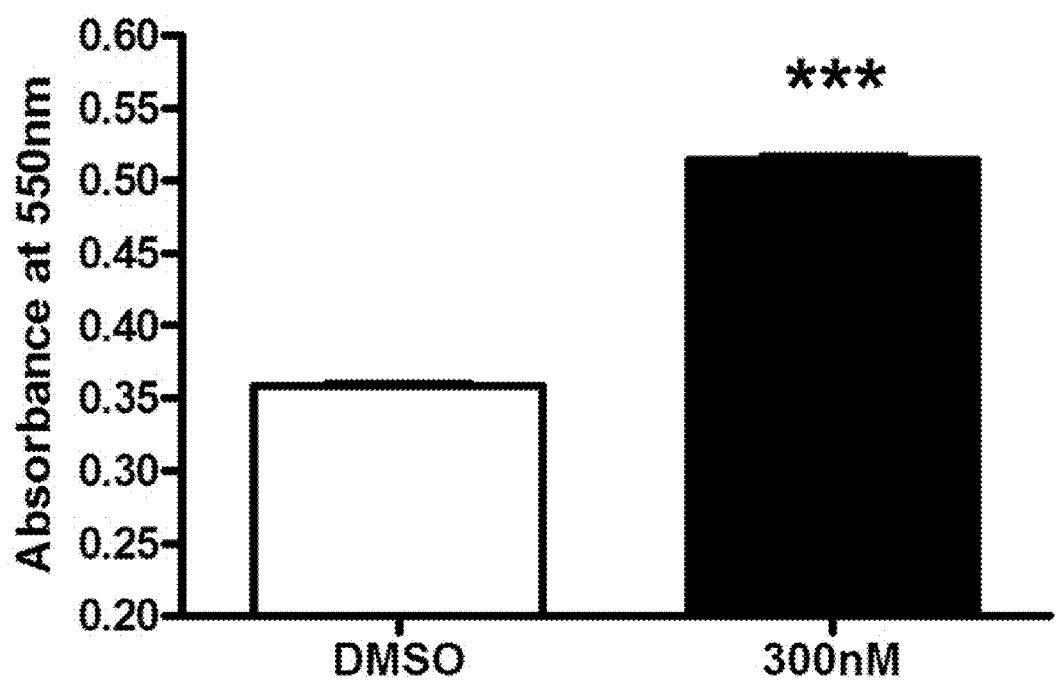
FIG. 1B: Effect of 300 nM 3-amino-6-(4-{3-[(3-methoxypropyl)amino]propyl}phenyl)-N-pyridin-3-ylpyrazine-2-carboxamide tri-hydrochloride on bone mineralization, Alizarin red S staining quantified using cetylpyridinium chloride extraction. Data are shown as mean absorbance at 550 nm and analysed using one-way ANOVA followed by Tukey's multiple comparison post hoc test: n=9; ***, $P<0.001$.

FIG. 1B: Effect of 300 nM 3-amino-6-(4-{3-[(3-methoxypropyl)amino]propyl}phenyl)-N-pyridin-3-ylpyrazine-2-carboxamide tri-hydrochloride on bone mineralization, Alizarin red S staining quantified using cetylpyridinium chloride extraction. Data are shown as mean absorbance at 550 nm and analysed using one-way ANOVA followed by Tukey's multiple comparison post hoc test: n=9; ***, $P<0.001$.

FIGS. 1A and 1B show that after 24 days of cell culture, 3-amino-6-(4-{3-[(3-methoxypropyl)amino]propyl}phenyl)-N-pyridin-3-ylpyrazine-2-carboxamide tri-hydrochloride significantly induced progenitor cell commitment and osteoblast differentiation as indicated through increased Alizarin red S staining relative to vehicle control.

d) Increased Bone Formation in Rats

Compound Dosing, Blood Sampling and Necropsy
3-amino-6-(4-{3-[(3-methoxypropyl)amino]propyl}phenyl)-N-pyridin-3-ylpyrazine-2-carboxamide tri-hydrochloride was formulated in water containing 0.5% HPMC ((Hydroxypropyl)methyl cellulose; Catalogue number H7509, Sigma, Poole, UK) and 0.1% Tween 80 (v/v) (Catalogue number P8074, Sigma, Poole UK). Female Sprague Dawley rats (Charles River CRL:CD rats, Deal, Margate, UK) aged between 12 and 16 weeks (230-340 g) were dosed with either compound or vehicle with a 5 mL/kg volume administered by oral gavage using straight steel (75 mm, 16 gauge) oral gavage feeding needles (Vet-Tech Solutions Ltd, Congleton, UK) between 7 and 10 am each day. Compound or vehicle was dosed at various doses (including 2.5, 5, 15 or 50 mg/kg/day freebase doses equivalent to 3, 6, 18 and 59 mg/kg of tri-hydrochloride salt) once a day for seven to fourteen days. In some studies a serum sample was taken prior to treatment to measure baseline serum bone biomarkers following overnight fasting. Blood was sampled from the tail vein and serum prepared by adding the blood to serum gel blood collection tubes (Microvette 500 Z-gel, catalogue number 20.1344, Sarstedt, Leicester, UK) and centrifuging the tubes for at 13000 rpm for 5 min at 4° C. The serum samples were stored at −80° C. before biomarker analysis. Twenty fours hours after the last treatment dose, necropsies were performed following termination by intraperitoneal injection overdose of pentobarbitone anesthetic (3 mL/kg of 200 mg/mL Euthatal, Merial Animal Health Ltd, Harlow, UK) in animals which had been fasted overnight. Following compound or vehicle treatment blood was taken from the descending aorta during necropsy in order to obtain terminal serum samples for serum bone biomarker analysis. Blood was drawn into a sterile 2.5 mL syringe through a 25 gauge×5/8 TW needle and decanted into 2×0.5 mL serum gel blood collection tubes (Monovette 500 Z-gel, catalogue number 20.1344, Sarstedt, Leicester, UK), centrifuged and stored at −80° C. prior to analysis. The femurs and lumbar vertebrae were removed for histopathological processing and bone formation assessments. The left femur and the $4^{th}$ or $5^{th}$ lumbar vertebrae were processed for histopathology. For rapid decalcification of bones (for preparing haematoxylin and eosin stained sections), femurs were fixed in 10% neutral buffered formalin (Catalogue number PRC/R/4, Pioneer Chemicals, Colchester, UK) for 10 days followed by a 5 day decalcification in 10% formic acid in water (Catalogue number F/1850/PB17, Fisher Scientific, Loughborough, UK), changing the decalcifying solution daily. Where immunohistochemistry was required, bones were fixed in 10% neutral buffered formalin for 10 days followed by decalcification with 12% EDTA (Diaminoethylene Tetra-Acetic Acid) plus 4% neutral buffered formalin (Catalogue number PRC/R/132, Pioneer Chemicals, Colchester, UK) at 50° C. for 7 weeks with the fluid changed every week. Following decalcification, the femurs were washed for 2 hours in running tap water and were processed by a standard overnight automatic processing schedule using a series of alcohol, ethyl alcohol and xylene solutions before final wax embedding. Four μm thick sections were cut with a microtome, stained with haematoxylin and eosin and histopathology assessment performed.

Evaluation of Bone Formation

The following techniques can be used to evaluate the effects of compounds on GSK3 inhibition and bone anabolism.

a) Histopathology

Histopathology changes in the rat femur sections were evaluated by light microscopy and bone formation was assessed by changes in trabeculae and cortical bone.

After 7 or 14 days, oral administration of 3-amino-6-(4-{3-[(3-methoxypropyl)amino]propyl}phenyl)-N-pyridin-3-ylpyrazine-2-carboxamide tri-hydrochloride, when dosed at 5 mg/kg, showed no differences in morphology in the femur when compared to the relevant vehicle control groups.

After 7 days of oral administration of 3-amino-6-(4-{3[(3-methoxypropyl)amino]propyl}phenyl)-N-pyridin-3-ylpyrazine-2-carboxamide tri-hydrochloride, oral doses of 15 and 50 mg/kg were associated with dose related changes of increased osteoid and bone in both the sub-chondral region and in the cortical bone in the shaft. In addition, both doses were associated with evidence of osteoblast hypertrophy (suggestive of osteoblast activation). Additionally, at the 50 mg/kg dose, there was evidence of increased bone within the cancellous bone compartment. This dose was also associated with histological evidence of bone marrow cell mobilization and differentiation, notably by increased numbers of immature (blast) osteoblasts within the cancellous bone compartment and an increase in marrow cellularity.

After 14 days of oral administration of 3-amino-6-(4-{3[(3-methoxypropyl)amino]propyl}phenyl)-N-pyridin-3-ylpyrazine-2-carboxamide tri-hydrochloride, the histological effects of 3-amino-6-(4-{3[(3-methoxypropyl)amino]propyl}phenyl)-N-pyridin-3-ylpyrazine-2-carboxamide tri-hydrochloride were qualitatively similar to those seen following 7 days of dosing but generally more pronounced and with evidence of greater bone marrow response to compound. Specifically, the 15 mg/kg dose of 3-amino-6-(4-{3[(3-methoxypropyl)amino]propyl}phenyl)-N-pyridin-3-ylpyrazine-2-carboxamide tri-hydrochloride showed evidence of bone formation in both the sub-chondral region and cortical region. Both findings were associated with osteoblast hypertrophy. The determination of bone formation was further strengthened by the observation of focal bone masses in the sub-chondral region in 2 out of 10 animals. In the 50 mg/kg group, there was a broader range of bone changes suggestive of bone formation in addition to those noted above: increased osteoid and tide mark zonation in the sub-chondral region; increased osteoid in the cancellous bone compartment and marked changes in bone marrow cellularity, specifically, expansion of a blast population which was morphologically consistent with osteoblast expansion.

Taken together, these data provide morphological support to the concept that 3-amino-6-(4-{3-[(3-methoxypropyl)amino]propyl}phenyl)-N-pyridin-3-ylpyrazine-2-carboxamide tri-hydrochloride elicits bone formation in vivo.

b) Bone Densitometry

Bone mineral density was measured using peripheral quantitative computed tomography, pQCT (Jämsä et al. Bone, 1998, 23, 155-61, Tuukkanen et al. J Bone Mineral. Res. 2000, 15, 1905-11) using Norland Stratec XCT Research SA+ equipment with a Stratec software version 6.0 (Norland Stratec Medizintechnik, Birkenfeld, Germany). The pQCT measurements were performed ex vivo on each right femur with a voxel size of $0.07 \times 0.07 \times 0.5$ mm$^3$. For the metaphyseal measurement, the site of CT scan was at the distal end of femur, at 25% of total bone length from the distal articular surface. The volumetric mineral density of the total bone (metaphysis total bone mineral density-BMD) was determined as mg/cm$^3$.

Oral administration of 3-amino-6-(4-{3-[(3-methoxypropyl)amino]propyl}phenyl)-N-pyridin-3-ylpyrazine-2-carboxamide tri-hydrochloride, dosed orally once a day for 14 consecutive days at 15 mg/kg in female CRL:CD rats, resulted in an 6.6% increase in right femur metaphysis total BMD compared with vehicle treated rats. Total BMD in femur from rats treated with 3-amino-6-(4-{3-[(3-methoxypropyl)amino]propyl}phenyl)-N-pyridin-3-ylpyrazine-2-carboxamide hydrochloride was 814.41±15 mg/cm$^3$ or vehicle was 764.23±16 mg/cm$^3$ (mean±SEM). These results indicate that oral administration of 3-amino-6-(4-{3-[(3-methoxypropyl)amino]propyl}phenyl)-N-pyridin-3-ylpyrazine-2-carboxamide tri-hydrochloride stimulates bone formation.

Bone Biomarker Evaluation

Bone biomarkers were determined by enzyme immunoassays (EIA) assay kits for N-terminal propeptide of type I procollagen (P1NP) and immunofixed enzyme activity assay kits for osteoclast-derived tartrate-resistant acid phosphatase form 5b (TRAcP-5b) specific for rat serum biomarker quantification. Assay kits were purchased from Immunodiagnostic Systems Ltd (IDS Ltd, Boldon, UK) and used as per the manufacturer's instructions, to determine N-terminal propeptide of type I procollagen (P1NP-product code AC-33F1) and osteoclast-derived tartrate-resistant acid phosphatase form 5b (TRAcP-5b-product code SB-TR102) levels in serum.

P1NP Assay

The P1NP assay used was a competitive immunoassay where P1NP in rat serum competes with biotin labeled PINP protein for plate immobilized antibody binding. Ninety six well assay plates supplied pre-coated with polyclonal rabbit anti-P1NP were incubated shaking at 700 rpm on a plate shaker for 1 hour at room temperature, with either 50 µA manufacturers supplied standards, or 5 µA serum plus 45 µA supplied assay sample diluent, plus 50 µL solution P1NP biotin solution supplied which contained biotin labeled P1NP protein. Each well of the assay plate was washed manually with 300 µL of supplied wash buffer three times, the wash buffer fully removed, and 150 µL of supplied enzyme conjugate (containing avidin linked to horseradish peroxidase) incubated for 30 min at room temperature. The assay plates were washed 3 times with wash buffer and 150 µL supplied TMB solution containing an aqueous formulation of tetramethylbenzidine and hydrogen peroxide incubated for 30 min at room temperature before the addition of 50 µL supplied 0.5M HCl to stop the reaction. The absorbance of all wells was determined at 450 nm with a reference absorbance of 650 nm using a Molecular Devices Spectromax-Plus spectrophotometer. The concentration of P1NP in serum samples was determined in ng/mL by using standard regression analysis against the standard curve.

TRAcP-5b Assay

The TRAcP-5b assay was carried out in 96 well assay plates supplied pre-coated with polyclonal anti-mouse IgG. Each well was incubated with 100 µL anti Rat TRAcP-5b antibody for 60 min, shaking at 950 rpm on a plate shaker at room temperature. Each well of the assay plate was washed manually with 300 µL of supplied wash buffer four times with an automatic 1200 µL multichannel pipette. The wash buffer was tapped out and either 100 µL of supplied standards or 25 µL serum samples with 75 µL 0.9% NaCl solution (Fresenius Kabi Ltd, Runcorn, UK, product code—2295121E) were incubated with 50 µL supplied releasing reagent for 1 hour shaking at room temperature. Each well of the assay plate was washed manually with 300 µL of supplied wash buffer five times. The wash buffer was fully removed and 100 µL of supplied and freshly prepared pNPP (p-nitrophenyl phosphate) substrate solution was incubated for 1 hour at 37° C. before the addition of 25 µL 0.32M NaOH was added to stop the reaction. The absorbance of all wells was determined at 405 nm using a Molecular Devices Spectromax-Plus spectrophotometer. The concentration of TRAcP-5b in serum samples was determined in U/L by using standard regression analysis against the standard curve.

Figure 2:
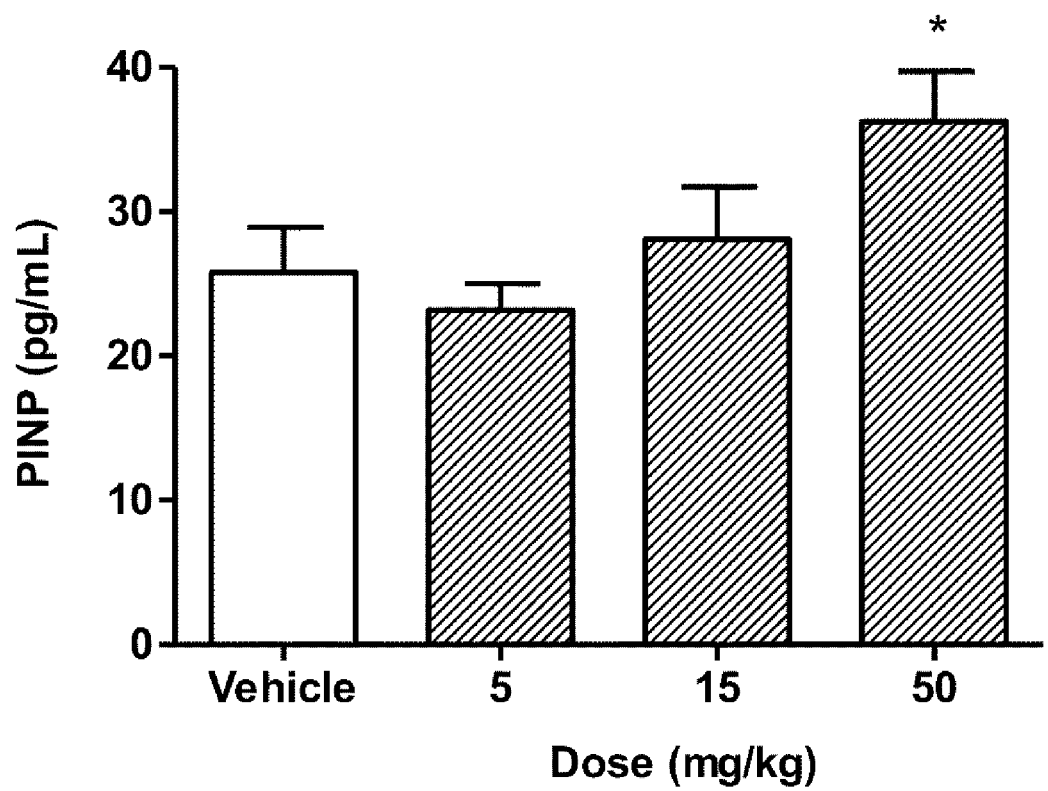
FIG. 2: Serum P1NP levels following 7 days of oral dosing with 3-amino-6-(4-{3-[(3-methoxypropyl)amino]propyl}phenyl)-N-pyridin-3-ylpyrazine-2-carboxamide tri-hydrochloride in rats. (Results expressed as mean±sem and *p<0.05, when a statistically significant difference was observed between compound treatment and vehicle control group.
Figure 3:
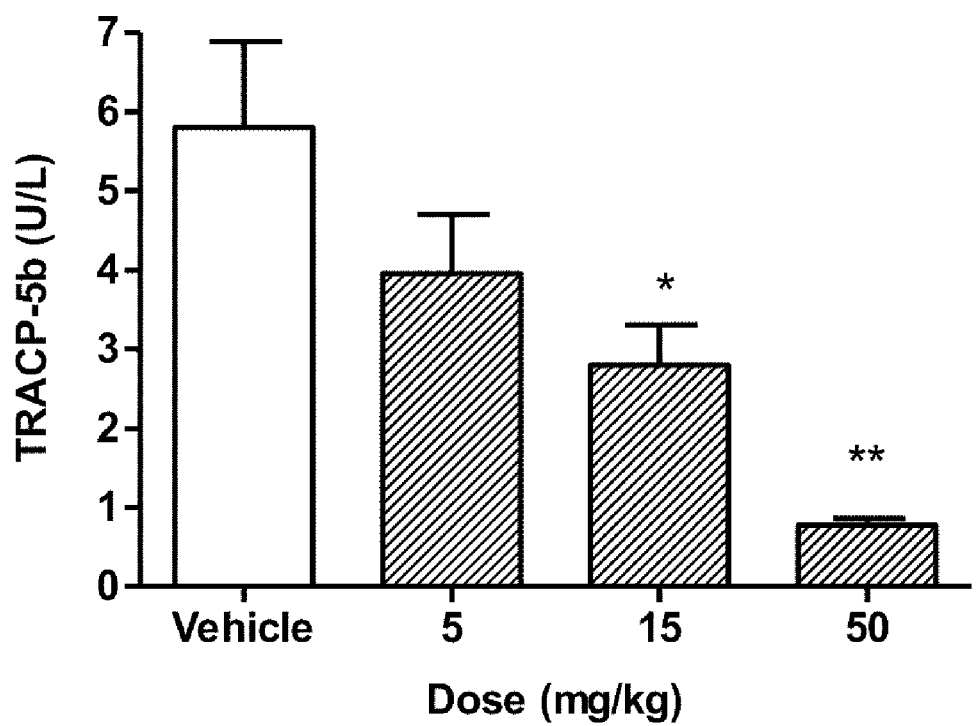
FIG. 3: Serum TRAcP-5b levels following 7 days of oral dosing with 3-amino-6-(4-{3-[(3-methoxypropyl)amino]propyl}phenyl)-N-pyridin-3-ylpyrazine-2-carboxamide tri-hydrochloride in rats. (Results expressed as mean±sem and *p<0.05 or **p<0.01, when a statistically significant difference was observed between compound treatment and vehicle control group).

FIG. 2. shows serum P1NP levels following 7 days of oral dosing with 3-amino-6-(4-{3-[(3-methoxypropyl)amino]propyl}phenyl)-N-pyridin-3-ylpyrazine-2-carboxamide tri-hydrochloride in rats FIG. 3. shows serum TRAcP-5b levels following 7 days of oral dosing with 3-amino-6-(4-{3-[(3-methoxypropyl)amino]propyl}phenyl)-N-pyridin-3-ylpyrazine-2-carboxamide tri-hydrochloride in rats The data shown in FIG. 2 and FIG. 3 demonstrate that 3-amino-6-(4-{3[(3-methoxypropyl)amino]propyl}phenyl)-

N-pyridin-3-ylpyrazine-2-carboxamide tri-hydrochloride, dosed orally once a day for 7 consecutive days in female CRL:CD rats, produced an increase in serum P1NP levels (marker of bone formation) and a reduction in serum TRAcP-5b levels (marker of bone resorption). These results indicate that oral administration of 3-amino-6-(4-{3-[(3-methoxypropyl)amino]propyl}phenyl)-N-pyridin-3-ylpyrazine-2-carboxamide tri-hydrochloride stimulates bone formation.

The following assay was used to measure the ability of 3-amino-6-(4-{3-[(3-methoxypropyl)amino] propyl}phenyl)-N-pyridin-3-ylpyrazine-2-carboxamide tri-hydrochloride to inhibit CYP3A4 in recombinant human enzymes.

Assay

The ability of certain compounds to inhibit CYP3A4 in membranes was determined from the inhibition of midazolam oxidation to 1'-hydroxy midazolam. Using midazolam, CYP3A4 catalyses the formation of 1'-hydroxymidazolam, which was measured by LC MS/MS Inhibition of CYP3A4 resulted in a decrease in the rate of 1'-hydroxymidazolam production relative to control. Employing an automated assay (full $IC_{50}$) using the Automation Platform, up to thirteen compounds were run per plate as well as ketoconazole as a standard inhibitor of CYP3A4.

Incubation

The incubations were carried out in 0.1 M phosphate buffer (pH 7.4 at 37° C.) containing DMSO (1%), midazolam (2.5 µM), phenacetin (25.7 µM), diclofenac (1.8 µM), S-mephenyloin (30.5 µM), bufuralol (8.8 µM), NADPH (1 mM), *E. coli* expressed 3A4 membranes (5 pmol/ml), 1A2 membranes (25 pmol/ml), 2C9 membranes (5 pmol/ml), 2C19 membranes (2.5 pmol/ml), 2D6 membranes (5 pmol/ml), and the test inhibitors ketoconazole, α-napthoflavone, sulphaphenazole, tranylcypromine and quinidine. Phenacetin and diclofenac were purchased from Sigma-Aldrich (Poole, dorset, UK). S-mephenyloin, bufuralol (hydrochloride salt) and midazolam (hydrochloride salt) were purchased from Ultrafine Chemicals (Manchester, UK). Recombinant expressed CYP enzymes were purchased from Cypex (Dundee, UK).

The assay was run on a robotic sample processor. The incubations were carried out in micro titre plates. The assay is started by the addition of NADPH (reduced Nicotinamide Adenine Dinucleotide Phosphate), the reagents mixed and the plate pre-incubated. The plate was then incubated for 10 min in the hotel incubator. The reaction was terminated with the addition of MeOH (1:1 vol/vol). The samples were centrifuged, transferred to a clean plate and analysed by LC MS/MS, which was conducted using an Applied Biosystems-Sciex API4000 mass spectrometer, with Agilent HP1100 binary solvent delivery pumps, and CTC HTS-PAL autosampler. Mobile phase consisted of Methanol and water with formic acid (0.1%) as modifier. The column used was a Phenomenex Max RP 50×2 mm (4 µm particle size). A gradient system was used, starting at 3% organic mobile phase for 0.25 min, raising to 100% organic at 1.75 min. Total run time was 2.5 min, with a flow rate of 0.6 ml/min. 10 µL was injected onto column). The formation of product (1'-hydroxymidazolam) was monitored.

Inhibitor Concentrations

The recommended concentrations for the test compounds were 50, 15, 5, 1.5, 0.5, 0.15 µM. A 5 mM stock of test inhibitor in DMSO was necessary to achieve these concentrations. Ketoconazole was used as a standard inhibitor and was incubated at 0.09-0.0003 µM.

Data Analysis

Rates of reaction were calculated for each reaction by measuring MS/MS area units. Data analysis was performed by linearising the data using a pseudo Hill plot and utilizing an automated spreadsheet.

The degree of inhibition of CYP3A4 was calculated and expressed as an $IC_{50}$ value. The $IC_{50}$ value is the concentration of test compound that inhibited 50% of CYP 3A4 activity. The estimated $IC_{50}$ value in the above assay for 3-amino-6-(4-{3-[(3-methoxypropyl)amino]propyl}phenyl)-N-pyridin-3-ylpyrazine-2-carboxamide tri-hydrochloride was >50 µM, indicating that the compound has negligible activity against CYP3A4.

The following assay was used to measure the activity of 3-amino-6-(4-{3-[(3-methoxypropyl)amino] propyl}phenyl)-N-pyridin-3-ylpyrazine-2-carboxamide tri-hydrochloride against the cardiac $Na^+$ channel, hNav1.5.

Cell Culture and Preparation

The hNav1.5-expressing Chinese hamster ovary K1 (CHO) cells used has been described previously (Persson, F. et al, (2005), Journal of Cardiovascular Electrophysiology, 16, 329-341). These cells were grown to semi-confluence at 37° C. in a humidified environment (5% CO2) in F-12 Ham medium containing Glutamax™, 10% foetal calf serum and 1 mg/ml G418 (all Invitrogen). Prior to use, the monolayer was washed using a pre-warmed (37° C.) 3 ml aliquot of Versene 1:5000 (Invitrogen). After aspiration of this solution the flask was incubated at 37° C. with a further 3 ml of Versene 1:5000 for a period of 6 min. Cells were then detached from the bottom of the flask by gentle tapping and 10 ml of Dulbecco's Phosphate-Buffered Saline containing calcium (0.9 mM) and magnesium (0.5 mM) (PBS; Invitrogen) was then added to the flask and aspirated into a 15 ml centrifuge tube prior to centrifugation (50 g, for 4 min). The resulting supernatant was discarded and the pellet gently re-suspended in 3 ml of PBS. A 0.5 ml aliquot of cell suspension was removed and the number of viable cells (based on trypan blue exclusion) was determined in an automated cell counter (Cedex; Innovatis) so that the cell re-suspension volume could be adjusted with PBS to give the desired final cell concentration. For Ion Works Quattro experiments, the final cell concentration used was 1,000,000 cells/ml.

Electrophysiology for IonWorks

The principles and operation of the IonWorks HT device have been described by Schroeder et al. (Schroeder, et al (2003), Ionworks HT: a new high-throughput electrophysiology measurement platform. Journal of Biomolecular Screening, 8, 50-64.2003). Briefly, the technology is based on a 384-well plate (PatchPlate) in which a recording is attempted in each well by using suction to position and hold a cell on a small hole separating two isolated fluid chambers. Once sealing has taken place, the solution on the underside of the PatchPlate is changed to one containing amphotericin B. This permeabilises the patch of cell membrane covering the hole in each well and, in effect, allows a perforated, whole-cell patch clamp recording to be made from a single cell. The IonWorks Quattro device uses the same technology except that recording are made from up to 64 cells per well. PBS (Invitrogen) was used as the extracellular solution with the following composition (in mM): 138 NaCl, 2.7 KCl, 0.9 CaCl2, 0.5 MgCl2, 1.5 KH2PO4, and 8.1 Na2HPO4. The "internal" solution (used during the seal formation process) composition was (in mM): Kgluconate 100, KCl 40, MgCl2 3.2, EGTA 3 and HEPES 5 (all Sigma-Aldrich; pH 7.25-7.30 using 10 M KOH). The antibiotic containing solution composition was (in mM): KCl 140, EGTA 1, MgCl2 1 and HEPES 20 (pH 7.25-7.30 using 10 M KOH) plus 100 µg/ml of amphotericin B (Sigma-Aldrich). Each compound plate was laid-out in 12 columns to enable ten, 8-point concentration-effect curves to be constructed; the remaining two columns on the plate were taken up with vehicle (final concentration 0.33% DMSO), to define the assay baseline, and a supra-maximal blocking concentration of flecainide (final concentration 316 µM) to define the 100% inhibition level. hNav1.5 currents were measured before and after approximately 3.5 min incubation with each test compound. In this way, non-cumulative concentration—effect curves could be produced where, providing the acceptance criteria were achieved in a sufficient percentage of wells (see below). All recordings were made at room temperature.

The pre- and post-compound hNav1.5 currents were evoked by a single voltage train consisting of a 15 s period holding at −90 mV, a 160 ms step to −100 mV (to obtain an estimate of leak current), a 100 ms step back to −90 mV, followed by a series of 8 pulses to 0 mV for 50 ms from a holding potential of −90 mV applied at 3 Hz. (A stimulation frequency of 3 Hz was chosen as it simulates the normal upper range of heart rate seen in humans—i.e. 180 beats per minute). In between the pre- and post-compound voltage pulses there was no clamping of the membrane potential. Currents were leak-subtracted based on the estimate of current evoked during the step to −100 mV at the start of the voltage pulse protocol. The current signal was sampled at 2.5 kHz.

Pre- and post-scan hNav1.5 current amplitude was measured from the leak-subtracted traces by the IonWorks™ software by taking the average current during the end of the depolarising pulse to 0 mV (baseline current) and subtracting this from the peak inward current. The acceptance criteria for the currents evoked in each well were: pre-scan seal resistance >30 MΩ (Quattro), pre-scan Na+ current amplitude more negative than −150 pA; post-scan seal resistance >30 MΩ (Quattro). The degree of inhibition of the hNav1.5 current was assessed by dividing the post-scan hNav1.5 current by the respective pre-scan hNav1.5 current for each well and for each of the eight test pulses.

The $IC_{50}$ value is the concentration of test compound that inhibited 50% of hNav1.5 activity. The $IC_{50}$ for 3-amino-6-(4-{3-[(3-methoxypropyl)amino]propyl}phenyl)-N-pyridin-3-ylpyrazine-2-carboxamide tri-hydrochloride was 21.2 µM, indicating that it does not display potent inhibitory activity against the cardiac $Na^+$ channel, hNav1.5.

3-amino-6-(4-{3-[(3-methoxypropyl)amino]propyl}phenyl)-N-pyridin-3-ylpyrazine-2-carboxamide mono-besylate was also tested in an in vivo rat genotoxicity micronucleus study. The objective of this study was to investigate whether two oral doses of 3-amino-6-(4-{3-[(3-methoxypropyl)amino]propyl}phenyl)-N-pyridin-3-ylpyrazine-2-carboxamide mono-besylate increased the frequency of micronucleated immature erythrocytes (MIE) in rat bone marrow.

3-amino-6-(4-{3-[(3-methoxypropyl)amino]propyl}phenyl)-N-pyridin-3-ylpyrazine-2-carboxamide mono-besylate was administered to groups of 7 male Wistar Han rats, approximately 10 weeks old at dosing. Groups were given two doses of 0, 25, 125 and 250 mg/kg free-base equivalent (0, 59.5, 297 and 595 umol/kg) 24 hours apart and sampled for bone marrow analysis 24 hours after the second dose. Control rats were dosed with vehicle, 0.5% w/v hydroxypropyl methylcellulose and 0.1% w/v polysorbate 80 in phosphate buffered saline. The highest dose was the maximum tolerated.

Animals were sacrificed 24 hours after the second dose and bone marrow smears prepared, fixed and stained with acridine orange. For each animal, 2000 immature erythrocytes (IE) were scored for the incidence of micronucleated cells (MIE) and the ratio of IE to mature erythrocytes (E) was determined in 1000 cells. In order to act as a quality control procedure, 6 slides from the bone-marrow of rats treated with cyclophosphamide at 20 mg/kg (72 umol/kg) in a previous study were included with the slides from the treated animals prior to staining and coding.

There were no biologically or statistically significant increases in the incidence of MIE above the vehicle control after two oral doses of 3-amino-6-(4-{3-[(3-methoxypropyl)amino]propyl}phenyl)-N-pyridin-3-ylpyrazine-2-carboxamide mono-besylate. The IE:E ratio was similar in the treated and vehicle control group. As expected, the incidence of MIE in the slides from rats previously given cyclophosphamide was significantly increased compared with the vehicle control values.

In conclusion, 3-amino-6-(4-{3-[(3-methoxypropyl)amino]propyl}phenyl)-N-pyridin-3-ylpyrazine-2-carboxamide mono-besylate did not increase the incidence of micronucleated immature erythrocytes in the bone marrow of male Wistar Han rats when administered as two oral doses up to 250 mg/kg free-base equivalent (595 umol/kg).

3-amino-6-(4-{3-[(3-methoxypropyl)amino]propyl}phenyl)-N-pyridin-3-ylpyrazine-2-carboxamide tri-hydrochloride was also found to exhibit other desirable properties, such as, for example, pharmaco-kinetic properties and a high aqueous solubility (mean measured solubility of approximately 1128 mg/ml in sodium phosphate buffer at pH 7.4, n=4).

According to a further aspect of the invention there is provided a pharmaceutical composition, which comprises a pyrazine derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing) or as a suppository for rectal dosing.

The compositions of the invention may also be used in conjunction with a suitable device or implant for treating bone tissue.

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, it has been found that compounds of the Formula I defined in the present invention, are well suited for inhibiting glycogen synthase kinase-3 (GSK3). Accordingly, said compounds of the present invention are expected to be useful in the prevention and/or treatment of conditions associated with glycogen synthase kinase-3 activity, i.e. the compounds may be used to produce an inhibitory effect of GSK3 in mammals, including human, in need of such prevention and/or treatment.

As stated hereinbefore, inhibitors of GSK3 enzymes should be of therapeutic value for prevention and/or treatment of various forms of bone-related disorders or conditions, such as, for example osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

According to an aspect of the invention there is provided a pyrazine derivative of the Formula I, or a pharmaceutically acceptable salt thereof, as defined hereinbefore for use as a medicament in a warm-blooded animal such as man.

According to a further aspect of the invention, there is provided a pyrazine derivative of the Formula I, or a pharmaceutically acceptable salt thereof, as defined hereinbefore for use in prevention and/or treatment of conditions associated with GSK3 in a warm-blooded animal such as man.

According to a further aspect of the invention, there is provided the use of a pyrazine derivative of the Formula I, or a pharmaceutically acceptable salt thereof, as defined hereinbefore for prevention and/or treatment of conditions associated with GSK3 in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the prevention and/or treatment of conditions associated with GSK3 in a warm-blooded animal such as man.

According to a further feature of this aspect of the invention there is provided a method for prevention and/or treatment of conditions associated with GSK3 in a warm blooded animal, such as man, in need of such treatment which comprises administering to said animal an effective amount of a pyrazine derivative of the Formula I, or a pharmaceutically acceptable salt thereof, as defined hereinbefore.

According to a further aspect of the invention, there is provided a pyrazine derivative of the Formula I, or a pharmaceutically acceptable salt thereof, as defined hereinbefore for use in the prevention of bone loss in a warm-blooded animal such as man.

According to a further aspect of the invention, there is provided the use of a pyrazine derivative of the Formula I, or a pharmaceutically acceptable salt thereof, as defined hereinbefore in the prevention of bone loss in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the in the prevention of bone loss effect in a warm-blooded animal such as man.

According to a further feature of this aspect of the invention there is provided a method for preventing bone loss in a warm blooded animal, such as man, in need of such treatment which comprises administering to said animal an effective amount of a pyrazine derivative of the Formula I, or a pharmaceutically acceptable salt thereof, as defined hereinbefore.

According to a further aspect of the invention there is provided a pyrazine derivative of the Formula I, or a pharmaceutically acceptable salt thereof, as defined hereinbefore for use in the prevention and/or treatment of those bone-related disorders or conditions which are sensitive to inhibition of GSK-3 enzymes in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the prevention and/or treatment of those bone-related disorders or conditions which are sensitive to inhibition of GSK-3 enzymes in a warm-blooded animal such as man.

According to a further feature of this aspect of the invention there is provided a method for the prevention and/or treatment of those bone-related disorders or conditions which are sensitive to inhibition of GSK-3 enzymes, which comprises administering to a warm-blooded animal such as man. an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in the prevention and/or treatment of osteoporosis (genetic, iatrogenic or generated through aging/hormone imbalance), fracture repair as a result of injury or surgery, chronic-inflammatory diseases that result in bone loss such as for example rheumatoid arthritis, bone lesions in cancers that lead to such bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the prevention and/or treatment of osteoporosis (genetic, iatrogenic or generated through aging/hormone imbalance), fracture repair as a result of injury or surgery, chronic-inflammatory diseases that result in bone loss such as for example rheumatoid arthritis, bone lesions in cancers that lead to such bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the prevention and/or treatment of osteoporosis (genetic, iatrogenic or generated through aging/hormone imbalance), fracture repair as a result of injury or surgery, chronic-inflammatory diseases that result in bone loss such as for example rheumatoid arthritis, bone lesions in cancers that lead to such bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided a method for preventing and/or treating osteoporosis (genetic, iatrogenic or generated through aging/hormone imbalance), fracture repair as a result of injury or surgery, chronic-inflammatory diseases that result in bone loss such as for example rheumatoid arthritis, bone lesions in cancers that lead to such bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm blooded animal such as man that is in need of such treatment which comprises administering an effective amount of a pyrazine derivative of the Formula I, or a pharmaceutically acceptable salt thereof, as defined hereinbefore.

A pyrazine compound of Formula I as hereinbefore defined could be useful in primary and secondary osteoporosis, where primary osteoporosis includes postmenopausal osteoporosis and senile osteoporosis in both men and women, and secondary osteoporosis includes cortison induced osteoporosis, as well as any other type of induced secondary osteoporosis, are included in the term osteoporosis. A pyrazine compound of Formula I may be administered locally or systemically, in different formulation regimes, to treat these conditions.

Accordingly, in a further feature of the invention there is provided a pyrazine derivative of the Formula I, or a pharmaceutically acceptable salt thereof, as defined hereinbefore for use in the treatment of osteoporosis (genetic, iatrogenic or generated through aging/hormone imbalance) in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the treatment of osteoporosis (genetic, iatrogenic or generated through aging/hormone imbalance) in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in the treatment of osteoporosis (genetic, iatrogenic or generated through aging/hormone imbalance) in a warm-blooded animal such as man.

According to a further feature of this aspect of the invention there is provided a method for treating osteoporosis (genetic, iatrogenic or generated through aging/hormone imbalance) in a warm blooded animal such as man that is in need of such treatment which comprises administering an effective amount of a chromenone derivative of the Formula I, or a pharmaceutically acceptable salt thereof, as defined hereinbefore.

The promotion and increasing of bone formation and/or bone mineral density makes a compound of the Formula I as hereinbefore defined, suitable for reducing the incidence of fracture, to reduce the rate of fracture and/or increase the rate of fracture healing, to increase cancellous bone formation and/or new bone formation in mammals. The use to promote and increase new bone formation may be in connection with surgery. This invention can be used during surgery, where the treating surgeon will place the invention locally in an appropriate formulation, near the deficient bone and/or in the body cavity. The bone may for instance have been broken, and utilizing the invention as described and claimed herein will then be placed in or near the fracture during open fracture repair. In some instances bone pieces may be missing (e.g. after tumour removal or severe casualties), and utilizing the invention as described and claimed herein will then be placed near the site of constructive bone surgery.

Accordingly, in a further feature of the invention there is provided a pyrazine derivative of the Formula I, or a pharmaceutically acceptable salt thereof, as defined hereinbefore for use in promoting bone formation in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in promoting bone formation in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in promoting bone formation in a warm-blooded animal such as man.

According to a further feature of this aspect of the invention there is provided a method for promoting bone formation in a warm blooded animal such as man that is in need of such treatment which comprises administering an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in increasing bone mineral density in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in increasing bone mineral density in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in increasing bone mineral density in a warm-blooded animal such as man.

According to a further feature of this aspect of the invention there is provided a method for increasing bone mineral density in a warm blooded animal such as man that is in need of such treatment which comprises administering an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in reducing the incidence of fracture and/or increasing the rate of fracture healing and/or increasing the strength of a healed fracture in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in reducing the incidence of fracture and/or increasing the rate of fracture healing and/or increasing the strength of a healed fracture in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in reducing the incidence of fracture and/or increasing the rate of fracture healing and/or increasing the strength of a healed fracture in a warm-blooded animal such as man.

According to a further feature of this aspect of the invention there is provided a method for reducing the incidence of fracture and/or increasing the rate of fracture healing and/or increasing the strength of a healed fracture in a warm blooded animal such as man that is in need of such treatment which comprises administering an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in prevention and/or treatment of bone lesions in cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in prevention and/or treatment of bone lesions in cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in prevention and/or treatment of bone lesions in cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm-blooded animal such as man.

According to a further feature of this aspect of the invention there is provided a method for prevention and/or treatment of bone lesions in cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease in a warm blooded animal such as man that is in need of such treatment which comprises administering an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in prevention and/or treatment of bone lesions in multiple myeloma in a warm-blooded animal such as man.

According to a further feature of this aspect of the invention there is provided the use of a pyrazine derivative of the Formula I, or a pharmaceutically acceptable salt thereof, as defined hereinbefore in the manufacture of a medicament for use in prevention and/or treatment of bone lesions in bone lesions in multiple myeloma in a warm-blooded animal such as man.

According to a further feature of this aspect of the invention there is provided a method for prevention and/or treatment of bone lesions in bone lesions in multiple myeloma in a warm blooded animal such as man that is in need of such treatment which comprises administering an effective amount of a pyrazine derivative of the Formula I, or a pharmaceutically acceptable salt thereof, as defined hereinbefore.

According to a further feature of the invention there is provided a pyrazine derivative of the Formula I, or a pharmaceutically acceptable salt thereof, as defined hereinbefore for use in the prevention of skeletal-related events in a warm-blooded animal such as man with bone lesions as a result of cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

According to a further feature of this aspect of the invention there is provided the use of a pyrazine derivative of the Formula I, or a pharmaceutically acceptable salt thereof, as defined hereinbefore in the manufacture of a medicament for use in the prevention of skeletal-related events in a warm-blooded animal such as man with bone lesions as a result of cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

According to a further feature of this aspect of the invention there is provided a method for preventing skeletal-related events in a warm-blooded animal such as man with bone lesions as a result of cancers such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease that is in need of such treatment which comprises administering an effective amount of a pyrazine derivative of the Formula I, or a pharmaceutically acceptable salt thereof, as defined hereinbefore.

In addition to bone-related disorders or conditions, there is evidence that GSK3 enzymes play a role in other diseases. Thus inhibitors of GSK3 enzymes, are expected to be of value in the prevention and treatment of a wide variety of diseases in addition to bone-related disorders or conditions. For example, inhibitors of GSK3 enzymes, are expected to be of value in the treatment of cancer. Indeed a particular pyrazine derivative of the Formula I, namely 3-amino-6-(4-{3-[(3-methoxypropyl)amino]propyl}phenyl)-N-pyridin-3-ylpyrazine-2-carboxamide tri-hydrochloride, has also been found to exhibit inhibitory activity against other kinases such as PIM3, CHK2 (checkpoint kinase 2) and DYRK1a (Dual Specificity Tyrosine Phosphorylated and Regulated Kinase 1a), which are also believed to play a role in cancer.

Accordingly, a pyrazine derivative of the Formula I, or a pharmaceutically acceptable salt thereof, should be of therapeutic value for treatment of the various forms of the disease of cancer comprising solid tumours such as carcinomas and sarcomas and the leukaemias and lymphoid malignancies. In particular, a pyrazine derivative of the Formula I, or a pharmaceutically acceptable salt thereof, should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further aspect of the invention, there is provided a pyrazine derivative of the Formula I, or a pharmaceutically acceptable salt thereof, as defined hereinbefore for use in the treatment of cancer in a warm blooded animal such as man.

According to a further aspect of the invention there is provided the use of a pyrazine derivative of the Formula I, or a pharmaceutically acceptable salt thereof, as defined hereinbefore in the manufacture of a medicament for use in the treatment of cancer in a warm blooded animal such as man.

According to a further feature of this aspect of the invention there is provided a method for the treatment of cancer in a warm blooded animal, such as man, in need of such treatment which comprises administering to said animal an effective amount of a pyrazine derivative of the Formula I, or a pharmaceutically acceptable salt thereof, as defined hereinbefore.

According to a further aspect of the invention, there is provided a pyrazine derivative of the Formula I, or a pharmaceutically acceptable salt thereof, as defined hereinbefore for use in the treatment of cancer selected from cancer of the breast, colorectum, lung (including small cell lung cancer, non-small cell lung cancer and bronchioalveolar cancer) and prostate.

According to a further aspect of the invention there is provided the use of a pyrazine derivative of the Formula I, or a pharmaceutically acceptable salt thereof, as defined hereinbefore in the manufacture of a medicament for use in treatment of cancer selected from cancer of the breast, colorectum, lung (including small cell lung cancer, non-small cell lung cancer and bronchioalveolar cancer) and prostate in a warm blooded animal such as man.

According to a further feature of this aspect of the invention there is provided a method for the treatment of cancer selected from cancer of the breast, colorectum, lung (including small cell lung cancer, non-small cell lung cancer and bronchioalveolar cancer) and prostate in a warm blooded animal, such as man, in need of such treatment which comprises administering to said animal an effective amount of a pyrazine derivative of the Formula I, or a pharmaceutically acceptable salt thereof, as defined hereinbefore.

In the context of the present specification, the term "therapy" or "treatment" also includes "prevention" unless there are specific indications to the contrary. The terms "therapeutic" and "therapeutically" should be construed accordingly.

In the context of the present specification, the term "disorder" also includes "condition" unless there are specific indications to the contrary.

As stated hereinbefore, the in vivo effects of a compound of the Formula I may be exerted in part by one or more metabolites that are formed within the human or animal body after administration of a compound of the Formula I.

The anti-bone loss treatment defined hereinbefore may be applied as a sole therapy or may involve, in addition to a compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107);

inhibitors of serine/threonine kinases (for example Ras/Raf signalling inhibitors such as farnesyl transferase inhibitors, for example sorafenib (BAY 43-9006), tipifarnib (R115777) and lonafarnib (SCH6336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin $\alpha v \beta 3$ function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) a proteosome inhibitor such as for example, Velcade (bortezomib)

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (xi) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

According to this aspect of the invention there is provided a combination suitable for use in the treatment of bone-related disorders or conditions comprising a compound of formula I as defined hereinbefore or a pharmaceutically acceptable salt thereof and any one of the anti tumour agents listed under (i)-(xi) above.

Therefore in a further aspect of the invention there is provided a compound of Formula I or a pharmaceutically acceptable salt thereof in combination with an anti-tumour agent selected from one listed under (i)-(xi) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of Formula I or a pharmaceutically acceptable salt thereof in combination with an anti-tumour agent selected from one listed under (i)-(xi) herein above, in association with a pharmaceutically acceptable diluent or carrier.

According to a further aspect of the invention there is provided a pharmaceutical composition which comprises a compound of Formula I or a pharmaceutically acceptable salt thereof in combination with an anti-tumour agent selected from one listed under (i)-(xi) herein above, in association with a pharmaceutically acceptable diluent or carrier for use in treating bone-related disorders or conditions.

According to another feature of the invention there is provided the use of a compound of the Formula I or a pharmaceutically acceptable salt thereof in combination with an anti-tumour agent selected from one listed under (i)-(xi) herein above, in the manufacture of a medicament for use in bone-related disorders or conditions in a warm-blooded animal, such as man.

Therefore in an additional feature of the invention, there is provided a method of treating bone-related disorders or conditions in a warm-blooded animal, such as man, in need of such treatment which comprises administering to said animal an effective amount of a compound of Formula I or a pharmaceutically acceptable salt thereof in combination with an anti-tumour agent selected from one listed under (i)-(xi) herein above.

According to a further aspect of the present invention there is provided a kit comprising a compound of Formula I or a pharmaceutically acceptable salt thereof in combination with an anti-tumour agent selected from one listed under (i)-(xi) herein above.

According to a further aspect of the present invention there is provided a kit comprising:
a) a compound of Formula I or a pharmaceutically acceptable salt thereof in a first unit dosage form;
b) an anti-tumour agent selected from one listed under (i)-(xi) herein above; in a second unit dosage form; and
c) container means for containing said first and second dosage forms.

The anti-bone loss treatment defined hereinbefore may be applied as a sole therapy or may involve, in addition to a compound of the invention, combination with other pharmacologically active agent(s), such as for example bisphosphonates, estrogen, SERMS (selective estrogen receptor modulators), RANKL (receptor activator of nuclear factor kB ligand) antagonists, calcitonins and oestogenic promoting agents such as parathyroid hormone or recombinant or synthetic parathyroid hormone. Examples of bisphosphonates include alendronate, clodronate, ibandronate, pamidronate, etidronate, risedronate, tiludronate and zoledronic acid. Examples of SERMS include raloxifene and dihydroraloxifene. An example of a RANKL antagonist is denosumab. Calcitonins include human and salmon calcitonins.

According to this aspect of the invention there is provided a combination suitable for use in the treatment of bone-related disorders or conditions comprising a compound of formula I as defined hereinbefore or a pharmaceutically acceptable salt thereof and a pharmacologically active agent, selected from a bisphosphonate, estrogen, a SERM, a RANKL antagonist, calcitonin and an oestogenic promoting agent.

According to a further aspect of the invention there is provided a pharmaceutical composition which comprises a compound of Formula I or a pharmaceutically acceptable salt thereof in combination with a pharmacologically active agent, selected from a bisphosphonate, estrogen, a SERM, a RANKL antagonist, calcitonin and an oestogenic promoting agent, in association with a pharmaceutically acceptable diluent or carrier.

According to a further aspect of the invention there is provided a pharmaceutical composition which comprises a compound of Formula I or a pharmaceutically acceptable salt thereof in combination with a pharmacologically active agent, selected from a bisphosphonate, estrogen, a SERM, a RANKL antagonist, calcitonin and an oestogenic promoting agent, in association with a pharmaceutically acceptable diluent or carrier for use in treating bone-related disorders or conditions.

According to another feature of the invention there is provided the use of a compound of the Formula I or a pharmaceutically acceptable salt thereof in combination with a pharmacologically active agent, selected from a bisphosphonate, estrogen, a SERM, a RANKL antagonist, calcitonin and an oestogenic promoting agent, in the treatment of bone-related disorders or conditions in a warm-blooded animal, such as man.

Therefore in an additional feature of the invention, there is provided a method of treating bone-related disorders or conditions in a warm-blooded animal, such as man, in need of such treatment which comprises administering to said animal an effective amount of a compound of Formula I or a pharmaceutically acceptable salt thereof in combination with a pharmacologically active agent, selected from a bisphosphonate, estrogen, a SERM, a RANKL antagonist, calcitonin and an oestogenic promoting agent.

Although the compounds of the Formula I are primarily of value as therapeutic agents for use in warm-blooded animals (including man), they are also useful whenever it required to inhibit the effects of GSK-3. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as nitrogen unless otherwise stated;

(ii) evaporations were carried out by rotary evaporation and work-up procedures were carried out after removal of residual solids by filtration;

(iii) flash chromatography purifications were performed on an automated combiflash companion (TELEDYNE, ISCO, USA), using prepacked Agela normal phase Si60 silica cartridges obtained from Agela technologies;

(iv) preparative chromatography was performed on a SHIMADZU instrument (LC-8A) fitted with a ZMD or ZQ ESCi mass spectrometers and a Luna reverse-phase column (C-18, 5 microns silica, 50 mm diameter, 250 mm length, flow rate of 80 ml/minute) using decreasingly polar mixtures of water (containing 0.1% TFA) and acetonitrile as eluent, or RPHPLC (Reversed Phase Preparative High Performance Liquid Chromatography) using Waters Symmetry C8, Xterra or Phenomenex Gemini columns using acetonitrile and either aqueous ammonium acetate, ammonia, formic acid or trifluoroacetic acid as buffer where appropriate;

(v) yields, where present, are not necessarily the maximum attainable;

(vi) in general, the structures of end-products of the Formula I were confirmed by nuclear magnetic resonance (NMR) spectroscopy; NMR chemical shift values were measured on the delta scale [proton magnetic resonance spectra were determined using a Varian or Bruker Avance 400 (400 MHz) instrument; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(vii) in general, end-products of the Formula I were also characterised by mass spectroscopy following liquid chromatography (LCMS); LCMS was carried out using an SHIMADZU 20AB fitted with SHIMADZU 2010EV mass spectrometer with a Xtimate 3 um C-18 column (2.1×30 mm) or a Shim-pack XR-ODS C-18 column (3.0×30 mm) at either: (a) a flow rate of 1.2 ml/min, using a solvent system of 10% A+90% B to 80% A+20% B over 3 minutes, where A=0.01875% TFA in acetonitrile, B=0.0375% TFA in H2O) or (b) a flow rate of 1.0 ml/min, using a solvent system of 90% A+10% B to 10% A+80% B over 2 minutes, where A=0.05% formic acid in water, B=0.05% formic acid in ACN;

(viii) X-ray powder diffraction spectra were determined (using a P'Analytical Cubix Analytical Instrument) by mounting a sample of the crystalline material on a single silicon crystal (SSC) wafer sample holder and spreading out the sample into a thin layer. The sample was spun at 30 revolutions per minute (to improve counting statistics) and irradiated with X-rays generated by a copper long-fine focus tube operated at 45 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 100 seconds per 0.02° 2-theta increment (continuous scan mode) over the range 2 degrees to 40 degrees 2-theta in theta-theta mode. The instrument was equipped with a Position sensitive detector (Lynxeye). Control and data capture was by means of a Dell Optiplex 686 Windows XP Workstation operating with X'Pert industry software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

(ix) Differential Scanning calorimetry was performed using a TA Instruments Q2000 DSC instrument. Typically less than 5 mg of material contained in a TZero aluminium pan fitted with a lid was heated over the temperature range 0° C. to 300° C. at a constant heating rate of 10° C. per minute. A purge gas, nitrogen, was used—flow rate 50 ml per minute. Generally a measurement error of approximately plus or minus 1° C. in the transition temperature values can be seen due to particle and sample size introducing thermal lag; and (x) the following abbreviations have been used:—

| | |
|---|---|
| Boc₂O | Di-tert-butyl dicarbonate |
| Br₂ | bromine |
| CDCl₃ | deuterated chloroform |
| DCM | dichloromethane |
| DMAP | 4-dimethylaminopyridine |
| DMF | N,N-dimethylformamide |
| DMSO | dimethyl sulphoxide |

| | |
|---|---|
| EtOAc | ethyl acetate |
| HATU | O-(7-Azabenzotriazol-1-yl)-N,N,N',N'-tetramethyluronium hexafluorophosphate |
| HCl | hydrogen chloride |
| HF | hydrogen fluoride |
| IPA | isopropyl alcohol |
| KOAc | potassium acetate |
| $K_2CO_3$ | potassium carbonate |
| $LiAlH_4$ | lithium aluminium hydride |
| MeCN | acetonitrile |
| MeOD | deutero-methanol |
| $MgSO_4$ | magnesium sulphate |
| MsCl | methanesulphonyl chloride |
| MTBE | methyl tert-butyl ether |
| $Na_2CO_3$ | sodium carbonate |
| NaOH | sodium hydroxide |
| $Na_2SO_4$ | sodium sulphate |
| NMP | 1-methyl-2-pyrrolidone |
| $N_2$ | nitrogen gas |
| $PCy_3$ | tricyclohexylphosphine |
| $Pd(dppf)Cl_2$ | dichloro[1,1'-bis(diphenylphosphino)ferrocene]palladium(II) |
| $Pd-Cl_2$ | dichloropalladium(II) |
| PE | petroleum ether |
| TBSCl | tert-butyldimethylsilyl chloride |
| THF | tetrahydrofuran |
| TEA | triethyl amine |
| TLC | thin layer chromatography |

EXAMPLE 1

3-Amino-6-(4-{3-[(3-methoxypropyl)amino]propyl}phenyl)-N-pyridin-3-ylpyrazine-2-carboxamide tri-hydrochloride

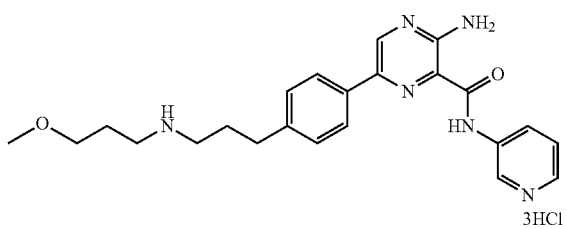

The title compound was prepared in accordance with the following scheme:

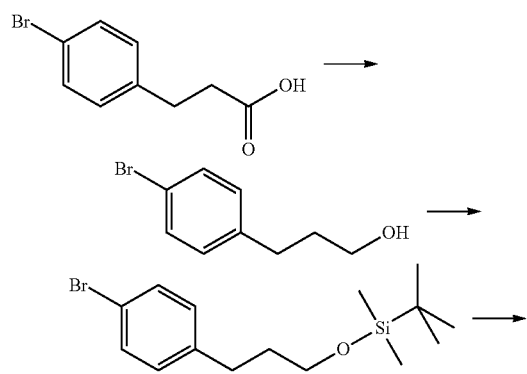

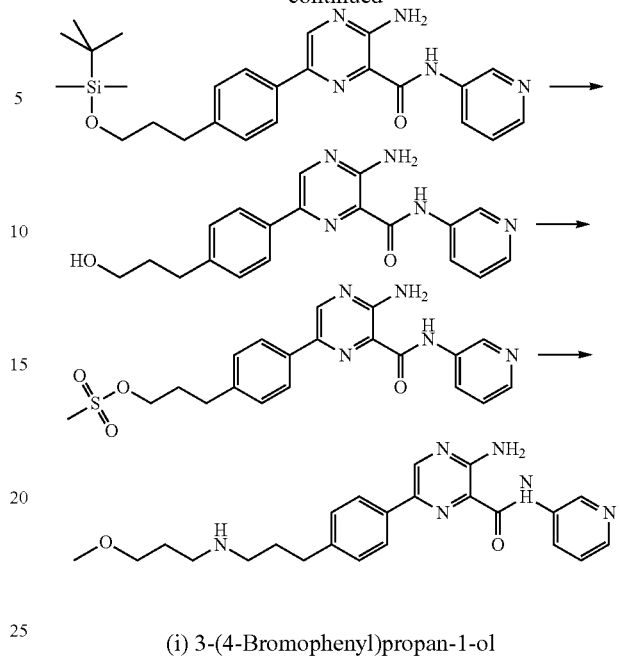

(i) 3-(4-Bromophenyl)propan-1-ol

To a solution of 3-(4-bromophenyl)-propionic acid (9.16 g, 40 mmol) in THF (150 mL) at 0° C. was added $LiAlH_4$ (1.4 g, 36 mmol) in portionwise. When the addition was completed, the reaction mixture was heated and stirred under reflux for additional 5 hours. The reaction mixture was cooled to 0° C. and 2 N—HCl (50 mL) added dropwise. The reaction mixture was extracted with EtOAc and washed with water (×3). The combined organic extract was dried over anhydrous $MgSO_4$, filtered and concentrated in vacuo, which afforded the subtitle compound (i) as an oil (8 g).

$^1$H-NMR (400 MHz, $CDCl_3$) δ 7.40 (d, 2H), 7.08 (d, 2H), 3.66 (t, 2H), 2.66 (t, 2H), 1.89-1.82 (m, 2H).

(ii) (3-(4-Bromophenyl)propoxy)(tert-butyl)dimethylsilane

To a solution of the product of step (i) (32.25 g, 0.15 mol) in anhydrous dichloromethane (400 mL) was added triethylamine (45 g, 0.45 mol), DMAP (915 mg, 7.5 mmol) and TBSCl (33 g, 0.215 mol) sequentially. The resulting solution was stirred overnight. The reaction mixture was extracted with dichloromethane and washed with water (×3). The combined organic layer was dried over anhydrous $MgSO_4$, filtered and concentrated in vacuo. The crude product was purified by column chromatography with PE to afford the subtitle compound (ii) as a pale brown oil (40 g).

$^1$H-NMR (400 MHz, $CDCl_3$) δ 7.34 (d, 2H), 7.02 (d, 2H), 3.56 (t, 2H), 2.58 (t, 2H), 1.77-1.73 (m, 2H), 0.86 (s, 9H), 0.00 (s, 6H);

HPLC Retention Time=1.017 min.

(iii) Methyl 3-amino-6-bromopyrazine-2-carboxylate

3-Aminopyrazine-2-carboxylic acid methyl ester (200 g, 1.3 mol, 3B Scientific Corporation) was dissolved in AcOH (1 L). The solution was warmed to 50° C. and $Br_2$ (312 g, 1.9 mol) added dropwise. When the addition was completed, the mixture was stirred at 50° C. for additional 3 hours. The reaction mixture was poured slowly to ice-water (4 L). The precipitate was filtered, washed with water and dried under a reduced pressure to afford the subtitle compound (iii) as a red brown solid (300 g).

¹H-NMR (400 MHz, CDCl₃) δ 8.28 (s, 1H), 3.97 (s, 3H); HPLC Retention Time=1.016 min.

(iv) 3-Amino-6-bromopyrazine-2-carboxylic acid

To a solution of the product of step (iii) (200 g, 0.86 mol) in MeOH (500 mL) was added 5 N—NaOH (500 mL) slowly. The resulting mixture was stirred at 50° C. for 3 hours. MeOH was removed under a reduced pressure and water (300 mL) added to the reaction mixture. The solution was acidified to pH 3 with 6N—HCl. The solution was extracted with EtOAc and washed with water. The combined organic extract was dried over Na₂SO₄, filtered and evaporated to dryness to afford the subtitle compound (iv) as a brown yellow solid (180 g).
¹H-NMR (400 MHz, CDCl₃) δ 8.30 (s, 1H); HPLC Retention Time=0.850 min.

(v) 3-Amino-6-bromo-N-(pyridin-3-yl)pyrazine-2-carboxamide

To a solution of the product of step (iv) (100 g, 0.45 mol) in DMF (350 mL) was added TEA (129 mL, 0.91 mol) and 3-aminopyridine (42.3 g, 0.45 mol). HATU (174 g, 0.45 mol) was added to the solution portionwise. The suspension was filtered, washed with water and dried under a reduced pressure to afford the subtitle compound (v) as a yellow solid (105 g).
¹H-NMR (400 MHz, CDCl₃) δ 9.50 (s, 1H), 8.81 (d, 1H), 8.40 (dd, 1H), 8.32 (s, 1H), 8.23-8.20 (m, 1H), 7.33 (dd, 1H). LCMS (ESI) m/z [M+H]+=294&296 (calc=294&296) (MultiMode+), HPLC Retention Time=0.478 min.

(vi) 3-Amino-6-(4-(3-(tert-butyldimethylsilyloxy)propyl)phenyl)-N-(pyridin-3-yl)-pyrazine-2-carboxamide A mixture of the product of step (ii) (9.84 g, 30 mmol), bis(pinacolato)diboron (11.4 g, 45 mmol), KOAc (9 g, 90 mmol) and Pd(dppf)Cl₂ (1 g, 1.5 mmol) in dioxane (200 mL) was stirred and degassed with N₂ (×3). The mixture was stirred at 80° C. under a N₂ atmosphere for 3 hours. The reaction mixture was cooled to room temperature. Water (25 mL) and Na₂CO₃ (10 g, 90 mmol) were added to the mixture. The mixture was stirred for 10 minutes before the product of step (v) (7.9 g, 27 mmol) and Pd(dppf)Cl₂ (0.5 g, 0.7 mmol) were added. The resulting solution was degassed again with N₂ (×3). The reaction mixture was stirred at 90° C. under a N₂ atmosphere for additional 10 hours. Na₂SO₄ was added, filtered and the filtrate concentrated in vacuo. The crude product was purified by column chromatography with PE:EtOAc=5:1 to 3:1 as eluent to afford the subtitle compound (vi) as a yellow solid (7.8 g).
¹H-NMR (400 MHz, CDCl₃) δ 9.90 (s, 1H), 8.73 (d, 1H), 8.62 (s, 1H), 8.34 (d, 1H), 8.21 (d, 1H), 7.74 (d, 2H), 7.28 (d, 2H), 7.28 (m, 1H), 3.6 (t, 2H), 2.68 (t, 2H), 1.83-1.79 (m, 2H), 0.86 (s, 9H), 0.00 (s, 6H); LCMS (ESI) m/z [M+H]+=464 (calc=464) (MultiMode+), HPLC Retention Time=1.233 min.

(vii) 3-Amino-6-(4-(3-hydroxypropyl)phenyl)-N-(pyridin-3-yl)pyrazine-2-carboxamide The product of step (vi) (14.5 g, 31.3 mmol) was added to a plastic vessel and THF (150 mL) added. HF (30 mL) was added carefully to the solution and the solution stirred at room temperature for 3 hours. The mixture was poured to 600 mL of water and 5 N—NaOH added to basify the solution to pH=10-11. The solution was extracted with EtOAc and washed with water (×3). The combined EtOAc extract was dried over MgSO₄, filtered and concentrated in vacuo, which afforded the subtitle compound (vii) as a yellow solid (10 g).
¹H-NMR (400 MHz, DMSO-d₆) δ 8.94 (d, 1H), 8.87 (s, 1H), 8.31 (dd, 1H), 8.18-8.16 (m, 1H), 8.10 (d, 2H), 7.60 (brs, 2H), 7.38 (dd, 1H), 7.28 (d, 2H), 3.39 (q, 2H), 2.61 (t, 2H), 1.75-1.65 (m, 2H); LCMS (ESI) m/z [M+H]+=350 (calc=350) (MultiMode+), HPLC Retention Time=0.858 min.

(viii) 3-(4-(5-Amino-6-(pyridin-3-ylcarbamoyl)pyrazin-2-yl)phenyl)propyl methanesulfonate Dichloromethane (200 mL) and diisopropylethylamine (2 g, 17.16 mmol) were added to the product of step (vii) (4 g, 11.46 mmol). The resulting solution was cooled to 0° C. and MsCl (2 g, 17.16 mmol) added dropwise. When the addition was completed, the resulting solution was stirred at 0° C. for 10 minutes and at room temperature for 2 hours. The reaction mixture was extracted with dichloromethane and washed with water (×3). The combined organic extract was dried over MgSO₄, filtered and concentrated in vacuo, which afforded the subtitle compound (viii) as a yellow brown solid (4.5 g).
¹H-NMR (400 MHz, CDCl₃) δ 9.94 (s, 1H), 8.81 (d, 1H), 8.70 (s, 1H), 8.41 (d, 1H), 8.30 (d, 1H), 7.84 (d, 2H), 7.34 (d, 2H), 7.34 (m, 1H), 4.27 (t, 2H), 3.03 (s, 3H), 2.84 (t, 2H), 2.17-2.10 (m, 2H);
LCMS (ESI) m/z [M+H]+=428 (calc=428) (MultiMode+), HPLC Retention Time=0.933 min.

(ix) 3-Amino-6-(4-(3-(3-methoxypropylamino)propyl)phenyl)-N-(pyridin-3-yl)-pyrazine-2-carboxamide tri-hydrochloride A mixture of the product of step (viii) (4.25 g, 10 mmol), K₂CO₃ (2.76 g, 20 mmol) and 3-methoxypropylamine (1.78 g, 20 mmol) in MeCN (100 mL) was stirred at 90° C. under a N₂ atmosphere overnight. The reaction mixture was cooled to room temperature and filtered. The filtrate was concentrated in vacuo and purified by a preparative HPLC. The fractions containing the desired compound were evaporated to reduce the volume of the solvent (acetonitrile and water) from 1 L to 50 ml and 0.5 M-aqueous HCl (20 mL) added. The resulting yellow solution was then lyophilized, which afforded the title compound as a tri-hydrochloride salt (yellow solid, 2.7 g).
¹H-NMR (400 MHz, MeOD) δ 9.63 (d, 1H), 8.95 (d, 1H), 8.81 (s, 1H), 8.64 (d, 1H), 8.12-8.09 (m, 1H), 8.10 (d, 2H), 7.42 (d, 2H), 3.51 (t, 2H), 3.34 (s, 3H), 3.13 (t, 2H), 3.05 (t, 2H), 2.78 (t, 2H), 2.10-2.00 (m, 2H), 1.98-1.90 (m, 2H);
LCMS (ESI) m/z [M+H]+=421 (calc=421) (MultiMode+), HPLC Retention Time=0.815 min.

EXAMPLE 2

3-Amino-6-(4-{3-[(3-methoxypropyl)amino]propyl}phenyl)-N-pyridin-3-ylpyrazine-carboxamide

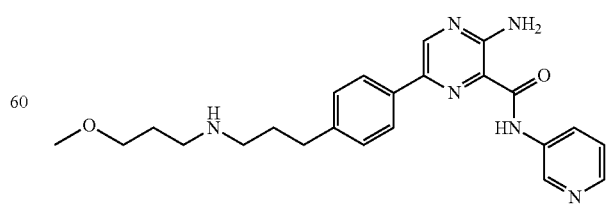

The title compound was prepared in accordance with the following scheme:

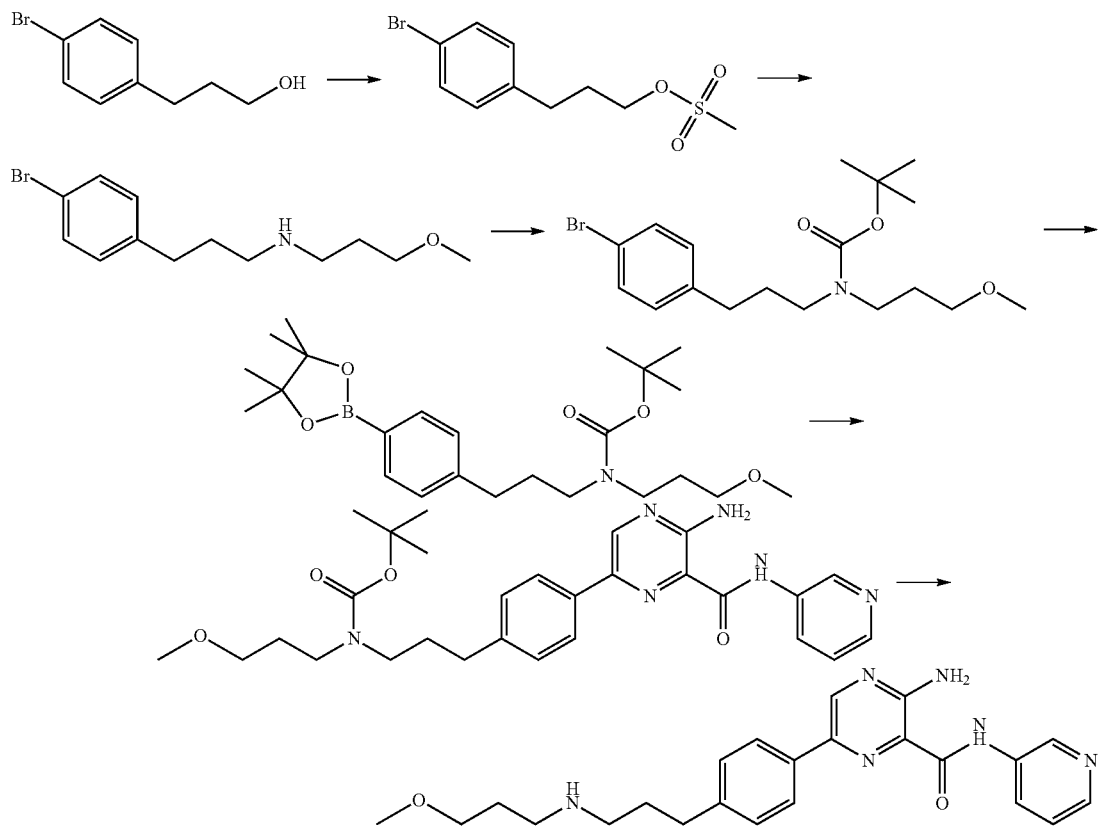

(i) 3-(4-Bromophenyl)propyl methanesulphonate

To a stirred solution of 3-(4-Bromophenyl)propan-1-ol (500 g, 2.30 mol) and diisopropylethylamine (312 g, 2.40 mol) in anhydrous dichloromethane (4 L) at 0~5° C. was added dropwise methanesulphonyl chloride (280 g, 2.40 mol) slowly. After addition, the reaction mixture was stirred for 1 hour at 0~5° C. The reaction mixture was washed with brine (1 L) twice. The organic phase was concentrated in vacuo to afford the subtitle compound (i) (667 g). HPLC Retention Time=1.353 min.

(ii) 3-(4-Bromophenyl)-N-(3-methoxypropyl)propan-1-amine

A mixture of the product of step (i) (272 g, 0.93 mol), $K_2CO_3$ (256 g, 1.86 mol), methoxypropylamine (199 g, 2.22 mol) in MeCN (1.5 L) was stirred at 80-90° C. under $N_2$ atmosphere for 16 hour. The reaction mixture was cooled to room temperature and filtered. The filtrate was concentrated to remove MeCN. MTBE (1 L) and $H_2O$ (1 L) were charged to the resulting mixture and washed with aqueous 1N—HCl (1 L). The aqueous phase was collected and basified by aqueous 2.5N—NaOH to pH=9-10, to afford the subtitle compound (ii) in solution, which was used for next step directly.

LCMS (ESI) m/z [M+H]+=286&288 (calc=286&288) (MultiMode+), HPLC Retention Time=0.935 min.

(iii) tert-Butyl N-[3-(4-bromophenyl)propyl]-N-(3-methoxypropyl)carbamate

To a stirred reaction mixture of the product of step (ii) (0.93 mol) in aqueous NaOH solution from last step, was charged with THF (1 L) and $Boc_2O$ (222 g, 1.01 mol) added to the mixture dropwise at 10° C. After addition, the mixture was stirred for 1 hour at 10° C. and extracted with MTBE (1 L×2). The organic phase was concentrated and purified by column chromatography (PE:EtOAc=10:1~5:1) to afford 300 g of the subtitle compound (iii). $^1$H NMR (400 MHz, $CDCl_3$) δ 7.38 (d, J=8.4 Hz, 2H), 7.05 (d, J=8.4 Hz, 2H) 3.35 (t, J=6.0 Hz, 2H), 3.30 (s, 3H), 3.22 (s, 4H), 2.54 (t, J=7.6 Hz, 2H), 1.76-1.84 (m, 4H), 1.43 (s, 9H). LCMS (ESI) m/z [M+H]+= 386&388 (calc=386&388) (MultiMode+).

(iv) tert-Butyl N-(3-methoxypropyl)-N-{3-[4-(4,4,5,5-tetramethyl-1,3,2-dioxaborolan-2-yl)phenyl]propyl}carbamate A mixture of the product of step (iii) (230 g, 0.60 mol), bis(pinacolato)diboron (227 g, 0.89 mol), KOAc (175 g, 1.79 mol), Pd—$Cl_2$ (3.20 g, 18 mmol), $PCy_3$ (10 g, 38 mmol) in MeCN (4 L) was stirred and degassed with $N_2$ three times. The reaction mixture was stirred at 80° C. under $N_2$ for 16 hours. The mixture was filtered and the filtrate concentrated in vacuo to remove MeCN. MTBE (3 L) was charged and the organic phase washed with $H_2O$ (800 mL×3) and concentrated to obtain the subtitle compound (iv) as an oil (250 g), which was used for next step directly. $^1$H-NMR (400 MHz, $CDCl_3$) δ 7.71 (d, J=8.0 Hz, 2H), 7.18 (d, J=8.0 Hz, 2H), 3.35 (t, J=6.0 Hz, 2H), 3.29 (s, 3H), 3.22 (s, 4H), 2.60 (t, J=7.6 Hz, 2H), 1.75-1.88 (m, 4H), 1.43 (s, 9H), 1.32

HPLC Retention Time=1.793 min.

(v) tert-Butyl N-[3-{4-[5-amino-6-(3-pyridylcarbamoyl)pyrazin-2-yl]phenyl}propyl]-N-(3-methoxypropyl)carbamate A mixture of the product of step (iv) (250 g, 0.58 mol), 3-amino-6-bromo-N-(pyridin-3-yl)pyrazine-2-carboxamide (220 g, 0.75 mol), $Na_2CO_3$ (183 g, 1.73 mol) and $Pd(dppf)Cl_2$ (25.30 g, 35 mmol) in DMF (3 L) was stirred and degassed with $N_2$ three times. The mixture was stirred at 70~80° C. under $N_2$ for 24 hours. The mixture was filtered and the filtrate concentrated to in vacuo to remove DMF. EtOAc (1.5 L) and $H_2O$ (800 mL) were charged and stirred for 1 hour at 10-25° C. The suspension was filtered, the organic phase was concentrated in vacuo and purified by column chromatography (PE: EtOAc=3:1-1:3). The crude product was re-crystallized from EtOAc-MeOH and filtered, the yellow solid was washed by EtOA and dried under reduced pressure. The subtitle compound (v) was obtained (pale yellow solid, 160 g).

LCMS (ESI) m/z [M+H]+=521 (calc=521) (MultiMode+), HPLC Retention Time=1.366 min.

(vi) 3-Amino-6-(4-(3-(3-methoxypropylamino)propyl)phenyl)-N-(pyridin-3-yl)-pyrazine-2-carboxamide A mixture of the product of step (v) (300 g, 0.58 mol) in 4N—HCl in EtOAc (3 L) was stirred for 3 hours. The suspension was filtered and the yellow solid obtained. The solid was dissolved in $H_2O$ (1.2 L). 2N—NaOH was added dropwise into the solution to basified to pH=11. The mixture was extracted with a mixture of THF and EtOAc (5 L×2, 1:1) and the organic phase washed with aqueous 10%—NaCl and concentrated in vacuo. The subtitle compound (vi) was obtained (pale yellow solid, 210 g).

$^1$H NMR (400 MHz, DMSO-$d_6$) δ 10.57 (s, 1H), 8.99 (d, J=2.4 Hz, 1H), 8.89 (s, 1H), 8.35 (dd, J=1.2 Hz, J=4.8 Hz, 1H), 8.23-8.20 (m, 1H), 8.12 (d, J=8.4 Hz, 2H), 7.67 (s, 2H), 7.40 (dd, J=4.8 Hz, J=4.8 Hz, 1H), 7.28 (d, J=8.4 Hz, 2H), 3.33 (t, J=6.8 Hz, 2H), 3.18 (s, 3H), 2.62 (t, J=7.2 Hz, 2H), 2.47 (dd, J=7.2 Hz, J=14 Hz, 4H), 1.73-1.65 (m, 2H), 1.62-1.56 (m, 2H).

The 3-amino-6-(4-{3-[(3-methoxypropyl)amino]propyl}phenyl)-N-pyridin-3-ylpyrazine-2-carboxamide Form B prepared as described above was determined to be crystalline by XRPD (see FIG. 4) and had the following X-Ray Powder Diffraction peaks:

| Angle 2-Theta (2θ) | Intensity % |
|---|---|
| 3.5 | 100 |
| 7.0 | 4 |
| 9.5 | 2 |
| 10.4 | 15 |
| 12.4 | 3 |
| 13.8 | 2 |
| 14.1 | 8 |
| 15.9 | 7 |
| 17.6 | 9 |
| 21.0 | 5 |

Figure 5:
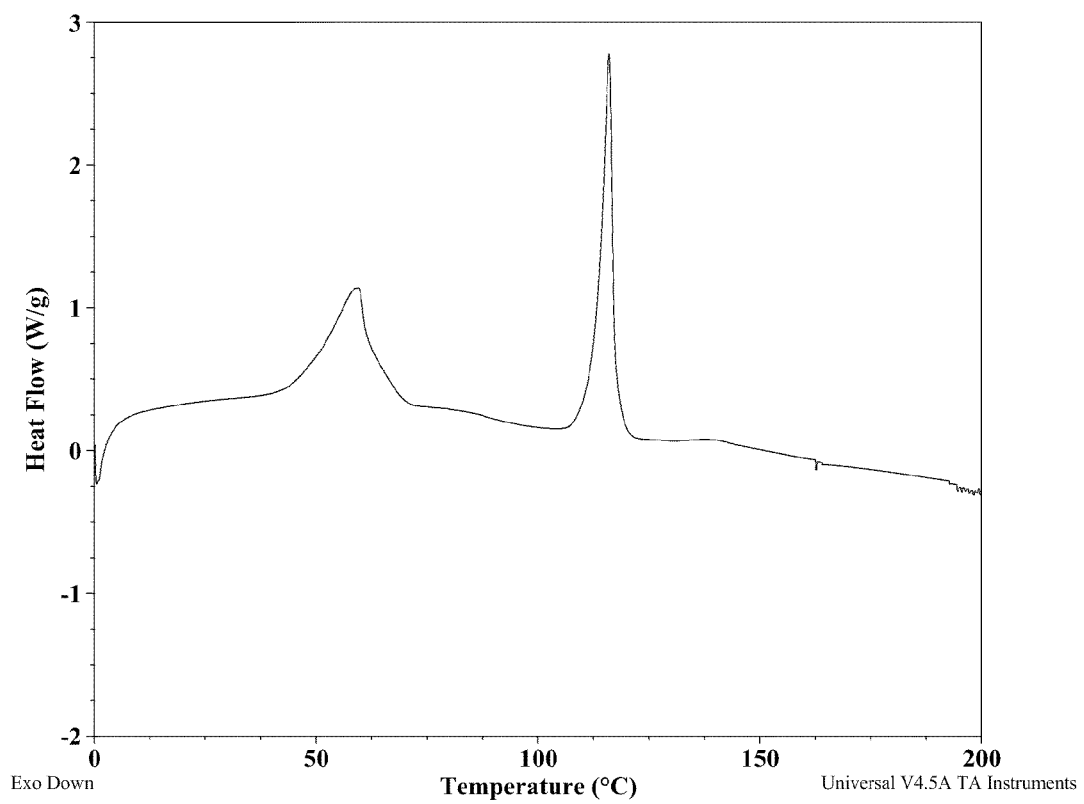
FIG. 5: DSC Thermogram of Form B of 3-amino-6-(4-{3-[(3-methoxypropyl)amino]propyl}phenyl)-N-pyridin-3-ylpyrazine-2-carboxamide.

DSC analysis of 3-amino-6-(4-{3-[(3-methoxypropyl)amino]propyl}phenyl)-N-pyridin-3-ylpyrazine-2-carboxamide Form B was also carried out (FIG. 5), using a heating rate of 10° C./min, and showed an initial endothermic event with an onset at 47° C. and a peak at 60° C. followed by a subsequent phase transition with an onset of 113° C. and a peak at 116° C. Thus, DSC analysis shows that 3-amino-6-(4-{3[(3-methoxypropyl)amino]propyl}phenyl)-N-pyridin-3-ylpyrazine-2-carboxamide Form B is a high melting solid with an onset of melting at about 113° C. and a peak at about 116° C.

EXAMPLE 3a

Form A of 3-amino-6-(4-{3-[(3-methoxypropyl)amino]propyl}phenyl)-N-pyridin-3-ylpyrazine-2-carboxamide mono-besylate 500.6 mg of 3-amino-6-(4-{3-[(3-methoxypropyl)amino]propyl}phenyl)-N-pyridin-3-ylpyrazine-2-carboxamide (as prepared in Example 2) and 189.09 mg of Benzenesulfonic acid were accurately weighed into a glass vial and the 15 mL IPA was added to form a suspension. The suspension was kept shaking for 2 days at room temperature, and then filtered and dried at room temperature to yield a yellow powder.

The Form A 3-amino-6-(4-{3-[(3-methoxypropyl)amino]propyl}phenyl)-N-pyridin-3-ylpyrazine-2-carboxamide mono-besylate prepared as described above was determined to be crystalline by XRPD (see FIG. 6a) and had the following X-Ray Powder Diffraction peaks:

| Angle 2-Theta (2θ) | Intensity % |
|---|---|
| 7.5 | 16 |
| 8.4 | 100 |
| 11.0 | 13 |
| 14.5 | 9 |
| 15.7 | 12 |
| 18.5 | 8 |
| 20.2 | 6 |
| 22.0 | 11 |
| 22.2 | 10 |
| 23.0 | 3 |

Figure 7A:
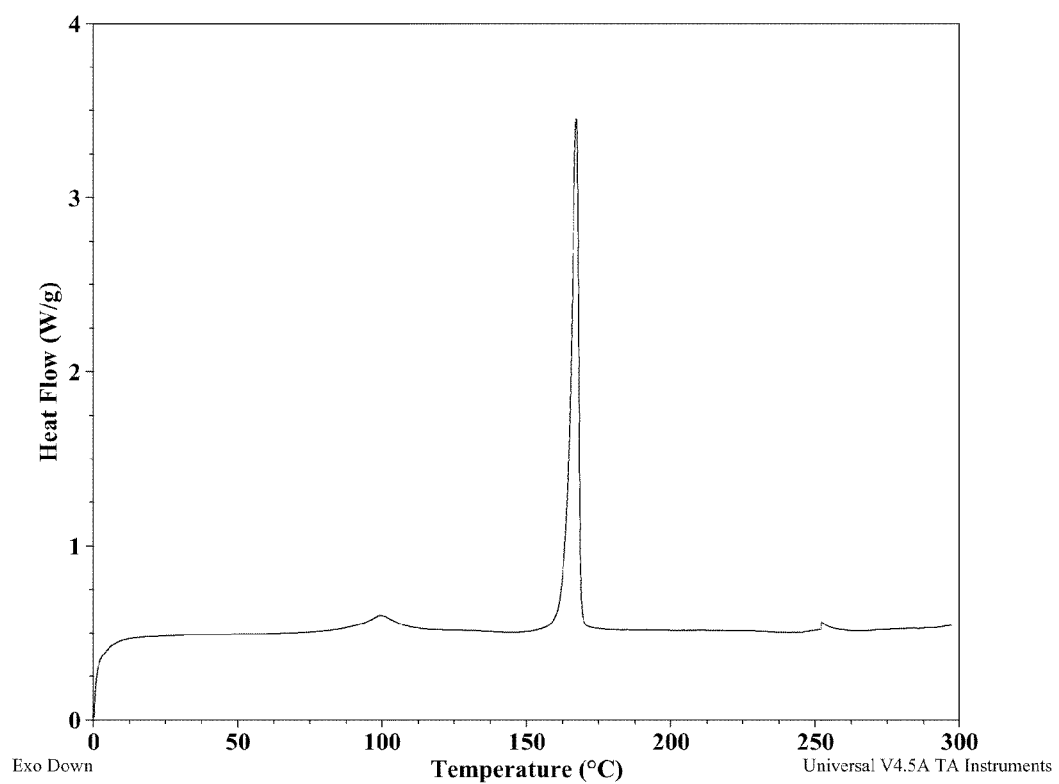
FIG. 7a: DSC-Thermogram for Form A of 3-amino-6-(4-{3-[(3-methoxypropyl)amino]propyl}phenyl)-N-pyridin-3-ylpyrazine-2-carboxamide mono-besylate.

DSC analysis of 3-amino-6-(4-{3-[(3-methoxypropyl)amino]propyl}phenyl)-N-pyridin-3-ylpyrazine-2-carboxamide mono-besylate Form A was also carried out, using a heating rate of 10° C./min, and showed an initial endothermic event with an onset at 89° C. and a peak at 99° C. followed by a melt with an onset of 164° C. and a peak at 167.0° C. (FIG. 7a). Thus, DSC analysis showed that 3-amino-6-(4-{3-[(3-methoxypropyl)amino]propyl}phenyl)-N-pyridin-3-ylpyrazine-2-carboxamide mono-besylate Form A is a high melting solid with an onset of melting at about 164° C. and a peak at about 167° C.

EXAMPLE 3b
Form C of 3-amino-6-(4-{3-[(3-methoxypropyl)amino]propyl}phenyl)-N-pyridin-3-ylpyrazine-2-carboxamide mono-besylate
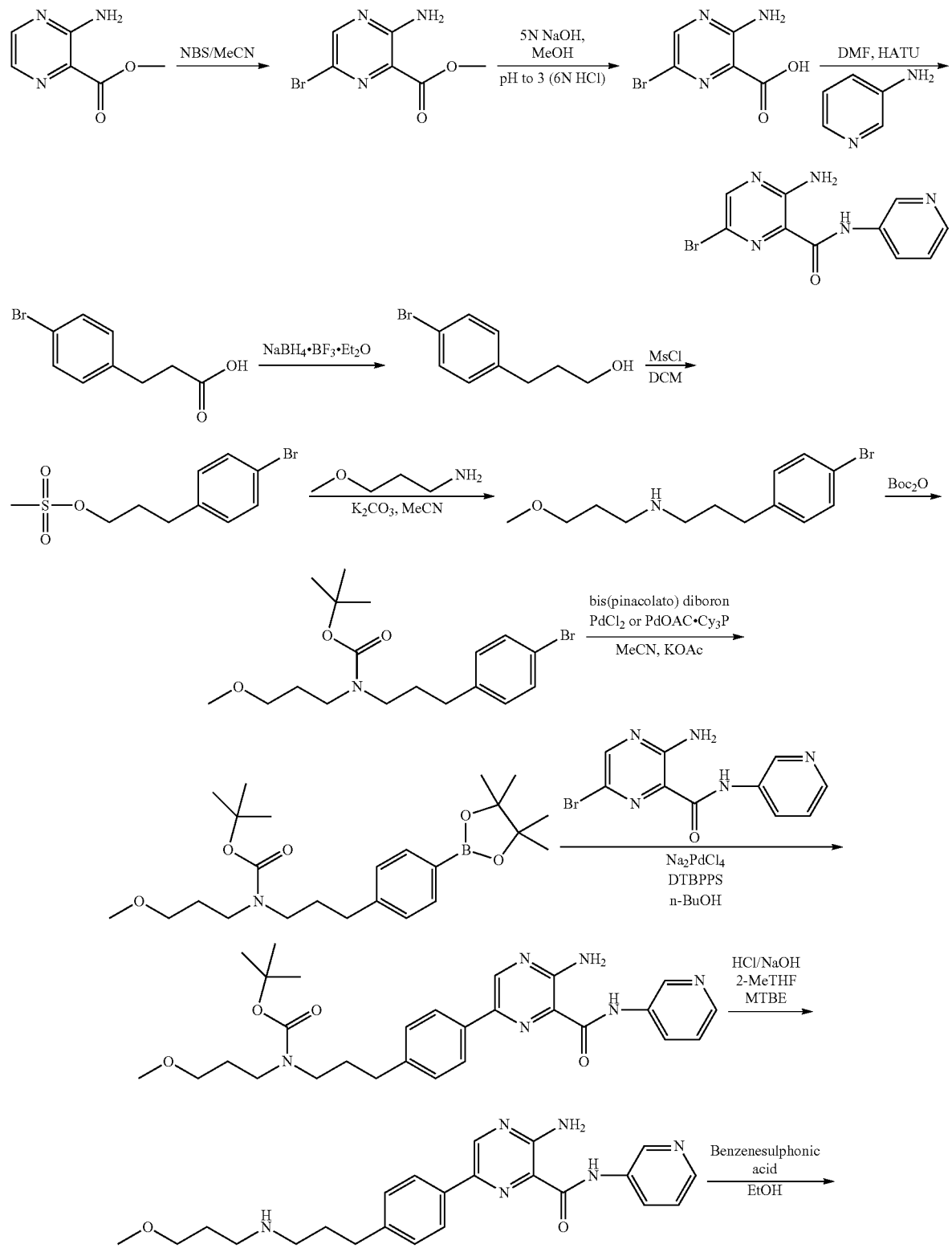

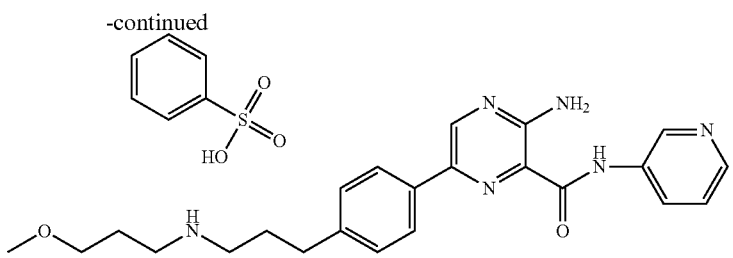

Synthesis of 3-Amino-6-bromo-N-(pyridin-3-yl)pyrazine-2-carboxamide

Stage 1: Methyl 3-amino-6-bromopyrazine-2-carboxylate

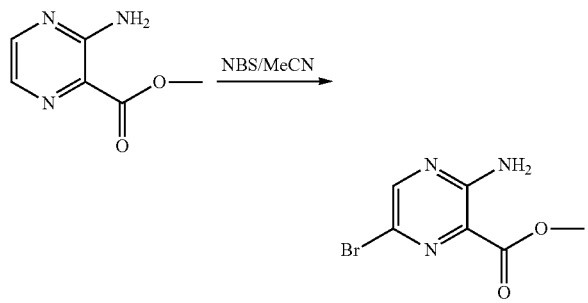

3-Aminopyrazine-2-carboxylic acid methyl ester (1 kg), N-bromosuccinimide (1.162 kg and acetonitrile (8 L) were charged into reactor. The mixture was stirred at room temperature for 10 min, heated to 75-80° C. and held for 2-3 hours under slightly refluxing conditions. The mixture was cooled to 25° C. and evaporated to dryness on a rotary evaporator. The resulting dark solids were redissolved in dichloromethane (20 L) and activated carbon (100 g) was charged. The resulting suspension was stirred at 25° C. for 30-60 minutes before filtering to remove insolubles. The filtrate was subsequently washed with saturated $Na_2SO_3$ (3×5 L) aqueous solution and water (5 L). The Organic layers were collected after phase separation. Dichloromethane was removed on rotary evaporator and Methyl 3-amino-6-bromopyrazine-2-carboxylate was obtained as a brown solid which was used in the next step without further purification (wet product 1090 g).

Stage 2: 3-amino-6-bromopyrazine-2-carboxylic acid

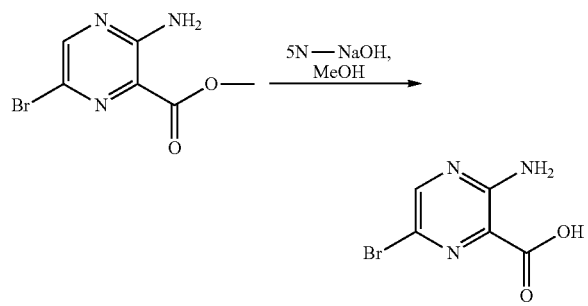

Methy 3-amino-6-bromopyrazine-2-carboxylate (1.4 Kg), 5N NaOH solution (5.6 L) and methanol (8.4 L) were charged into reactor. The resulting suspension was warmed at 50° C. for 3 hours with vigorous stirring. The mixture was analysed for reaction completion. The mixture was cooled to 25° C. and the solids were collected by filtration. Filter cake was washed with water (1 L). The resultant solids were suspended in water (5 L) and pH value of this suspension was adjusted to 3 by adding 6 N HCl solution. The acidic solution was vigorously stirred at 25° C. for 48 h. During this period, pH value was checked, additional acid was charged if pH value >3. The suspension was filtered to collect a yellow-brown solid, which was dried in oven at 40° C. under a flow of $N_2$. The crude subtitle material was used in the next step.

Stage 3: 3-Amino-6-bromo-N-(pyridin-3-yl)pyrazine-2-carboxamide

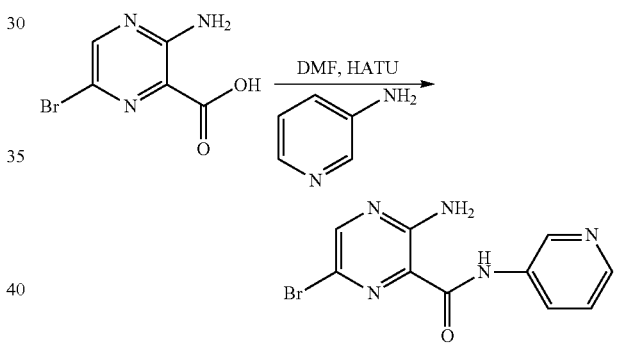

3-Amino-6-bromopyrazine-2-carboxylic acid (1.07 kg), 3-aminopyridine (460 g), triethylamine (680 ml) and DMF (6.4 L) were charged into a reactor. The mixture was cooled to −5 to 0° C. and stirred for 15 min. Under a nitrogen flow, HATU (1.8 kg) was slowly added in many portions while maintaining the temperature below 10° C. Upon addition, thick yellow precipitate formed. After addition, the mixture was stirred at 20-25° C. for 1 h. The reaction was analysed for completion (3-Amino-6-bromopyrazine-2-carboxylic acid=0%). Water (13 L) was added under vigorous stirring. The yellow suspension was stirred at 25° C. for 30 min. The suspension was filtered and the filter cake was recharged into reactor. Water (13 L) was charged. The yellow suspension was warmed to 50° C. and stirred at this temperature for 2 h. The suspension was filtered and the filter cake was washed with water. The wet product (3-Amino-6-bromo-N-(pyridin-3-yl)pyrazine-2-carboxamide) was dried in oven at 55° C. under a flow of nitrogen. (1.14 Kg).

$^1$H-NMR (400 MHz, DMSO-$d_6$) 7.39 (dd, 1H); 7.74 (br.s., 2H); 8.18 (ddd, 1H); 8.33 (dd, 1H); 8.43 (s, 1H); 8.96 (d, 1H); 10.51 (s, 1H).

Synthesis of tert-butyl (3-methoxypropyl){3-[4-(4,4,5,5-tetramethyl-1,3,2-dioxaborolan-2-yl)phenyl]propyl}carbamate

Stage 1: 3-(4-bromophenyl)propan-1-ol

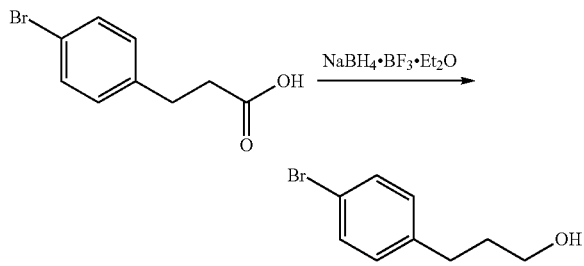

Sodium borohydride (119.12 g) and THF (5 L) were charged into reactor 1 and temperature adjusted to −20° C. 3-(bromophenyl)propionic acid (1 kg) was charged into reactor 2 with THF (3 L) and stirred at 25° C. until all the solids dissolved. This solution in reactor 2 was transferred to reactor 1 maintaining reactor 1 contents at <0° C. $BF_3 \cdot Et_2O$ (991.4 g) was slowly added into reactor 1 maintaining reactor 1 contents at −20 to −10° C. After addition, the mixture was stirred at −20 to −10° C. for 1 h. The reaction is analysed for completion (3-(bromophenyl)propionic acid <2.5%). Water (2 L) was slowly added into reactor 1 to quench the reaction. (gas evolution). MTBE (5 L) was charged into reactor 1 and phases separation was carried out. The upper layer was collected and lower layer was washed with MTBE (5 L). The upper layer was collected and combined with the layer from the previous step. Adjusted pH value of the organic layer to 8-9 by adding 1N NaOH solution. The organic layer was washed with saturated NaCl solution (2 L) and the upper layer was collected. The organic layer was evaporated down to a colourless oil.

Stage 2: 3-(4-bromophenyl)propyl methanesulfonate

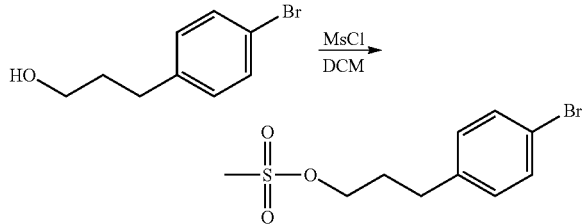

3-(4-Bromophenyl)propan-1-ol (335 g) and dichloromethane (2.5 L) was charged into Reactor 1. Reactor 1 was adjusted to −10 to 0° C. Triethylamine (205 g) was charged into Reactor 1. Methanesulphonyl chloride (272.7 g) was added dropwise into Reactor 1 maintaining contents at <0° C. Reactor 1 was stirred at −5 to 5° C. for 1 h then analysed for reaction completion. The organic layer was washed with water (1 L) and saturated NaCl solution (1 L). The organic layer was evaporated down to dryness to give 3-(4-bromophenyl)propyl methanesulfonate (418 g).

Stage 3: 3-(4-bromophenyl)-N-(3-methoxypropyl)propan-1-amine

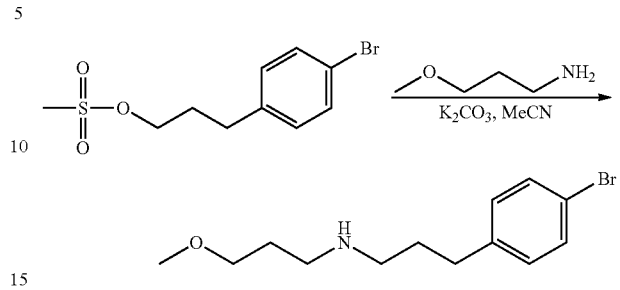

3-(4-bromophenyl)propyl methanesulfonate (418 g) and acetonitrile (2 L) were charged into reactor 1. 3-methoxypropylamine (305 g) and potassium carbonate (394 g) were added to reactor 1 and the mixture was warmed to 80-90° C. for 4-16 h. The mixture was analysed for completion (3-(4-bromophenyl)propyl methanesulfonate <0.5%). The reaction was cooled to 25° C. and the suspension was filtered to remove the white solids. The filtrate was concentrated to dryness on a rotary evaporator. The crude product from the rotary evaporator, MTBE (2 L) and water (1.5 L) were charged into reactor 2. After phase separation, the organic layer was collected and washed with 1N HCl (2 L) until pH=4-5. After phase separation, the aqueous phase was basified by 2.5N NaOH solution to pH=9-10 and the resulting aqueous solution was used in the next step without further treatment.

Stage 4: tert-butyl [3-(4-bromophenyl)propyl](3-methoxypropyl)carbamate

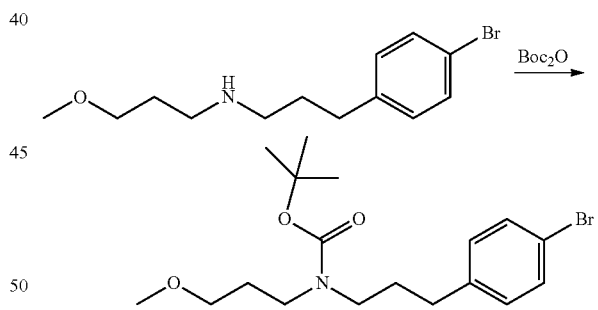

3-(4-bromophenyl)-N-(3-methoxypropyl)propan-1-amine (500 g) in water (1.5 L) and THF (500 ml) was charged into reactor Triethylamine (176.8 g) was charged into reactor at 10° C. $Boc_2O$ (475.5 g) was added dropwise to the mixture in reactor 1 at 10° C. and the mixture was stirred for 1 h at 10° C. The mixture was analysed for reaction completion. The mixture was extracted with MTBE (3×1 L). The combined organic layers were evaporated to down to give crude product as oil. The crude product was further purified by silica gel column chromatography. (Petroleum ether:Ethyl acetate=1:0-20:1-10:1). tert-butyl [3-(4-bromophenyl)propyl](3-methoxypropyl)carbamate was obtained as slightly yellow oil. (327.0 g)

Stage 5: tert-butyl (3-methoxypropyl) {3-[4-(4,4,5,5-tetramethyl-1,3,2-dioxaborolan-2-yl)phenyl]propyl}carbamate

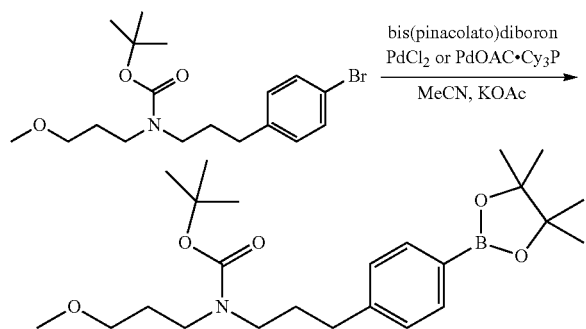

tert-butyl [3-(4-bromophenyl)propyl](3-methoxypropyl)carbamate (500 g) and acetonitrile (4.3 L) were charged into reactor 1 along with bis(pinacolato)diboron (394.4 g), potassium acetate (190.5 g), PCy₃ (23.2 g) and Pd(OAc)₂ (8.7 g). The vessel was swing purged with nitrogen three times. The mixture was warmed to 85-90° C. for 16 h then analysed for complete reaction (tert-butyl [3-(4-bromophenyl)propyl](3-methoxypropyl)carbamate <0.5%). The mixture was cooled to 25° C., filtered and the filtrate was concentrated to remove MeCN. MTBE (3 L) was charged and MTBE layer washed with water (3×1.5 L). The MTBE layer was concentrated to give crude product. The crude product was further purified by silica gel column chromatography. (Petroleum ether:Ethyl acetate=1:0-40:1-10:1). tert-butyl (3-methoxypropyl){3-[4-(4,4,5,5-tetramethyl-1,3,2-dioxaborolan-2-yl)phenyl]propyl}carbamate was obtained as slightly yellow oil. (490.0 g)

$^1$H-NMR (400 MHz, DMSO-d$_6$) δ ppm 1.27 (s, 12H); 1.35 (m, 9H); 1.65 (m, 2H); 1.74 (m, 2H); 2.54 (t, 2H); 3.10 (m, 1H); 3.15 (m, 1H); 3.18 (s, 3H); 3.26 (t, 2H); 7.19 (d, 2H); 7.58 (d, 2H).

Synthesis of 3-amino-6-(4-{3-[(3-methoxypropyl)amino]propyl}phenyl)-N-pyridin-3-ylpyrazine-2-carboxamide mono-besylate Stage 1: (tert-butyl (3-{4-[5-amino-6-(pyridin-3-ylcarbamoyl)pyrazin-2-yl]phenyl}propyl)(3-methoxypropyl)carbamate To a reactor was charged, 3-Amino-6-bromo-N-(pyridin-3-yl)pyrazine-2-carboxamide (1580 g), tert-butyl (3-methoxypropyl){3-[4-(4,4,5,5-tetramethyl-1,3,2-dioxaborolan-2-yl)phenyl]propyl}carbamate (2778 g) 1-butanol (23.7 L), potassium phosphate, tribasic, N-hydrate (2740 g) and water (1.58 L). The contents were stirred under nitrogen at ambient (21° C.). In a second reactor was made up a solution of 3-(di-tert-butylphosphonium)propane sulphonate (DTBPPS) (83.04 g); sodium tetrachloropalladate (45.52 g) and water (1.58 L). The catalyst/ligand solution was poured into the reaction; the reaction was inerted and heated up to 80° C. The reaction was stirred for 2 hours at 80° C. The batch was cooled to 60° C. and water (22.1 L) was added. The contents washed with water at 60° C. The organic layer and interface were filtered through perlite (500 g) made up with 1-Butanol (3.95 L). The organic liquors were recharged to the vessel and washed with water (11.1 L) at 60° C. The organic liquor was washed with 10% w/v aqueous sodium chloride (11.2 L) at 60° C. The organic liquors were heated up to 60° C. and distilled under vacuum to ~10 relative volumes. The batch was cooled to 20° C. and left to stir for 16 hours under nitrogen. The contents were filtered and washed with 1-Butanol (4 L×2). The yellow free flowing solid was discharged and dried in vacuum oven at 40° C. overnight (tert-butyl (3-{4-[5-amino-6-(pyridin-3-ylcarbamoyl)pyrazin-2-yl]phenyl}propyl)(3-methoxypropyl)carbamate (2428 g)).

$^1$H NMR (400 MHz, DMSO-d$_6$) δ ppm 1.37 (s, 9H) 1.62-1.72 (m, 2H) 1.73-1.87 (m, 2H) 2.59 (t, J=7.65 Hz, 2H) 3.12-3.21 (m, 4H) 3.19 (s, 3H) 3.28 (t, J=6.25 Hz, 2H) 7.31 (d, J=8.10 Hz, 2H) 7.42 (dd, J=8.41, 4.74 Hz, 1H) 7.62 (br. s., 2H) 8.13 (d, J=8.10 Hz, 2 H) 8.21 (ddd, J=8.40, 2.60, 1.40 Hz, 1H) 8.35 (dd, J=4.70, 1.40 Hz, 1H) 8.90 (s, 1H) 8.98 (d, J=2.59 Hz, 1H) 10.54 (s, 1H)

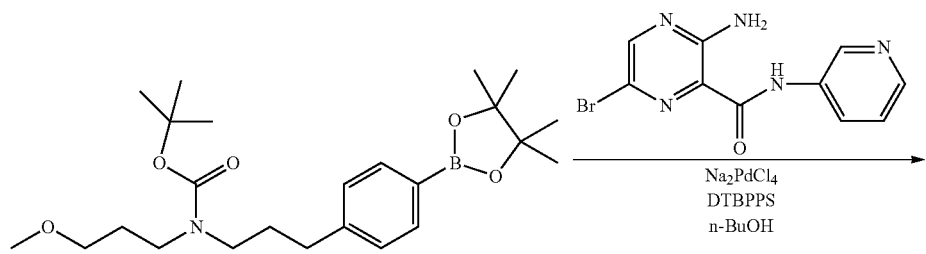

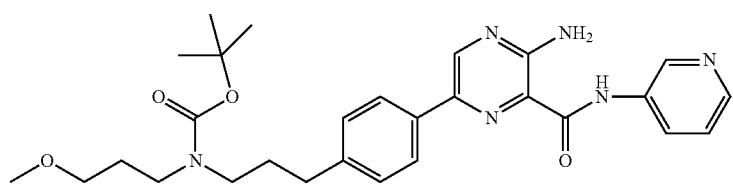

Stage 2: 3-amino-6-(4-{3-[(3-methoxypropyl)amino]propyl}phenyl)-N-pyridin-3-ylpyrazine-2-carboxamide

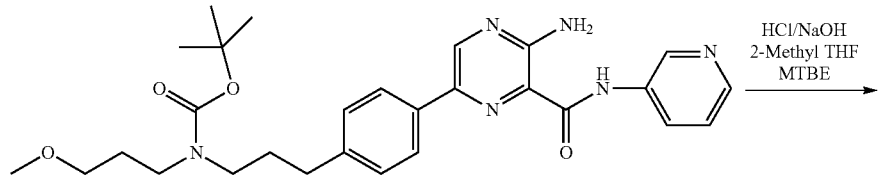

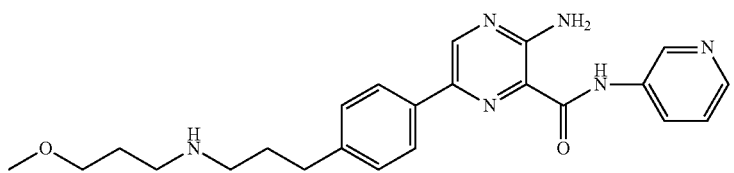

Tert-butyl (3-{4-[5-amino-6-(pyridin-3-ylcarbamoyl)pyrazin-2-yl]phenyl}propyl)(3-methoxypropyl)carbamate (1 kg) and water (8 L) were added to the reactor, stirred and heated up to 70° C. 36% Hydrochloric acid (606 ml) was added slowly controlling rate of gas evolution. The contents were stirred for 45 minutes at 70° C. The pH was adjusted to 3-4 by addition of sodium hydroxide (325 ml). The contents were cooled to 50° C. and 2-methyltetrahydrofuran (5 L) was added. The pH was then adjusted to pH 11-12 by the addition of 48% sodium hydroxide liquor (170 ml). The contents were then cooled to 40° C. The batch allowed to settle and the two layers separated. The aqueous layer was washed with 2-methyltetrahydrofuran (2.5 L). The combined organic layers were washed with a solution of 10% w/v aqueous sodium chloride solution. The organic layer was distilled to remove 3.75 L of distillate. The remaining liquors were heated to 50° C. and methyl-t-butyl ether (4 L) added. The liquors were cooled to 10° C. over 4 hours then isolated by filtration. The solid was washed with methyl-t-butyl ether (2 L×2) and dried in a vacuum oven at 50° C. 3-amino-6-(4-{3-[(3-methoxypropyl)amino]propyl}phenyl)-N-pyridin-3-ylpyrazine-2-carboxamide (721 g).

$^1$H NMR (400 MHz, DMSO-d$_6$) δ ppm 1.77-1.87 (m, 2H) 1.88-2.01 (m, 2H) 2.72 (t, J=7.65 Hz, 2H) 2.89-3.03 (m, 4H) 3.23 (s, 3H) 3.39 (t, J=5.98 Hz, 2H) 7.35 (d, J=8.30 Hz, 2H) 7.68 (br. s., 2H) 7.68 (dd, J=8.62, 5.17 Hz, 1H) 8.18 (d, J=8.30 Hz, 2H) 8.41-8.52 (m, 2H) 8.57 (br. s., 2H) 8.94 (s, 1H) 9.16 (d, J=2.15 Hz, 1H) 10.77 (s, 1H)

Stage 3: 3-amino-6-(4-{3-[(3-methoxypropyl)amino]propyl}phenyl)-N-pyridin-3-ylpyrazine-2-carboxamide mono-besylate

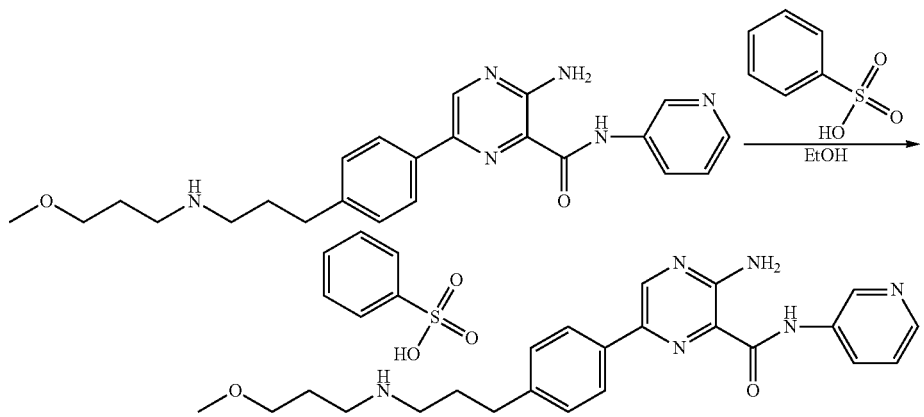

To reactor was charged 3-amino-6-(4-{3-[(3-methoxypropyl)amino]propyl}phenyl)-N-pyridin-3-ylpyrazine-2-carboxamide (700 g) and ethanol (4.9 L). The contents were heated up to 60° C. to give a solution. Benzene sulphonic acid (258 g) was charged to the reactor followed by ethanol (2.1 L) and water (70 ml). The contents heated up to 60° C. The complete solution was then cooled to 51° C. and seeded with Form A of 3-amino-6-(4-{3-[(3-methoxypropyl)amino]propyl}phenyl)-N-pyridin-3-ylpyrazine-2-carboxamide mono-besylate (0.35 g, as prepared in accordance with Example 3a). Once crystallisation was established the contents were held at 51° C. for 2 hours then ramp cooled to 40°

C. over 4 hours, held at 40° C. for 4 hours then further cooled to 10° C. over 4 hours. The contents were held at 10° C. for 12 hours then filtered and washed with ethanol (700 ml×2). The solid 3-amino-6-(4-{3-[(3-methoxypropyl)amino]propyl}phenyl)-N-pyridin-3-ylpyrazine-2-carboxamide mono-besylate Form C was dried in a vacuum oven at 40° C. (810 g).

$^1$H-NMR (700 MHz, DMSO-$d_6$) δ ppm 1.78-1.86 (m, 2H) 1.92 (quin, J=7.70 Hz, 2H) 2.70 (t, J=7.70 Hz, 2H) 2.89-2.99 (m, 4H) 3.22 (s, 3H) 3.37 (t, J=6.05 Hz, 2H) 7.28-7.35 (m, 5H) 7.47 (dd, J=8.25, 4.73 Hz, 1H) 7.62 (br. s., 2H) 7.62 (dd, J=7.92, 1.54 Hz, 2H) 8.16 (d, J=8.36 Hz, 2H) 8.27 (ddd, J=8.30, 2.40, 1.30 Hz, 1H) 8.34 (br. s., 2H) 8.38 (dd, J=4.70, 1.32 Hz, 1H) 8.91 (s, 1H) 9.01 (d, J=2.42 Hz, 1H) 10.57 (s, 1H)

The Form C 3-amino-6-(4-{3-[(3-methoxypropyl)amino]propyl}phenyl)-N-pyridin-3-ylpyrazine-2-carboxamide mono-besylate prepared as described directly above was determined to be crystalline by XRPD (see FIG. 6b) and had the following X-Ray Powder Diffraction peaks:

| Angle 2-Theta (2θ) | Intensity % |
| --- | --- |
| 11.2 | 0.9 |
| 12.6 | 0.3 |
| 14.7 | 0.6 |
| 15.5 | 0.7 |
| 15.8 | 0.7 |
| 16.8 | 0.8 |
| 20.4 | 0.7 |
| 21.1 | 4.3 |
| 22.5 | 1.8 |
| 26.5 | 0.3 |

Figure 7B:
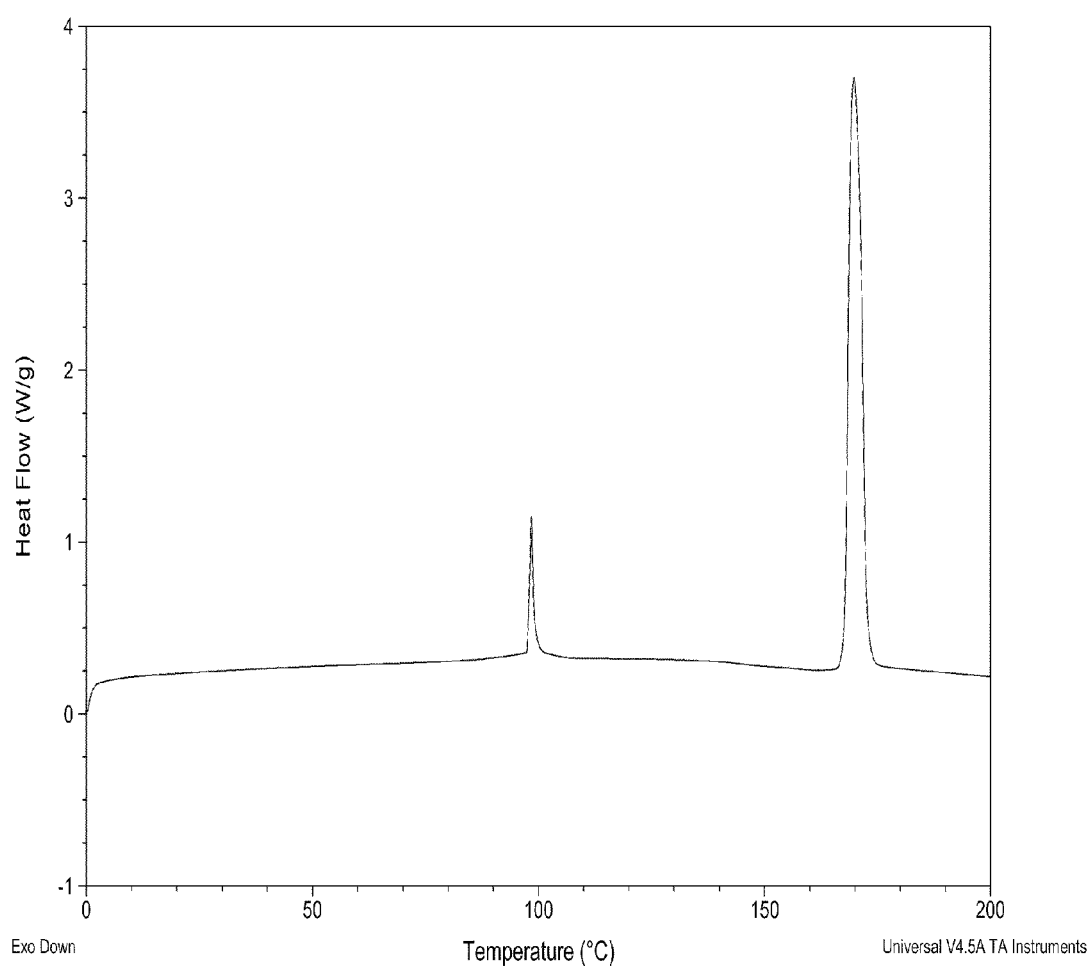
FIG. 7b: DSC-Thermogram for Form C of 3-amino-6-(4-{3-[(3-methoxypropyl)amino]propyl}phenyl)-N-pyridin-3-ylpyrazine-2-carboxamide mono-besylate.

DSC analysis of 3-amino-6-(4-{3-[(3-methoxypropyl)amino]propyl}phenyl)-N-pyridin-3-ylpyrazine-2-carboxamide mono-besylate Form C was also carried out, using a heating rate of 10° C./min and showed a solid to solid transition with an onset of 98° C. and a peak at 99° C. followed by a subsequent phase transition with an onset of 165° C. and a peak at 170° C. (FIG. 7b). Thus, DSC analysis showed that 3-amino-6-(4-{3-[(3-methoxypropyl)amino]propyl}phenyl)-N-pyridin-3-ylpyrazine-2-carboxamide mono-besylate Form C is a high melting solid with an onset of melting at about 165° C. and a peak at about 170° C.

EXAMPLE 4.1-4.4

Particular salts of 3-amino-6-(4-{3-[(3-methoxypropyl)amino]propyl}phenyl)-N-pyridin-3-ylpyrazine-2-carboxamide

EXAMPLE 4.1

3-amino-6-(4-{3-[(3-methoxypropyl)amino]propyl}phenyl)-N-pyridin-3-ylpyrazine-2-carboxamide mono-tosylate

EXAMPLE 4.2

3-amino-6-(4-{3-[(3-methoxypropyl)amino]propyl}phenyl)-N-pyridin-3-ylpyrazine-2-carboxamide di-esylate

EXAMPLE 4.3

3-amino-6-(4-{3-[(3-methoxypropyl)amino]propyl}phenyl)-N-pyridin-3-ylpyrazine-2-carboxamide mono-DL-mandelate

EXAMPLE 4.4

3-amino-6-(4-{3-[(3-methoxypropyl)amino]propyl}phenyl)-N-pyridin-3-ylpyrazine-2-carboxamide mono-benzoate The mono-benzoate Form A, mono-DL-mandelate Form A and mono-tosylate Form A salts were prepared by reacting approximately 500 mg 3-amino-6-(4-{3-[(3-methoxypropyl)amino]propyl}phenyl)-N-pyridin-3-ylpyrazine-2-carboxamide Form B with 1 molar equivalent of the appropriate counterion in 10 mL of IPA. The reaction was carried out at room temperature and the mixture stirred for 5 days prior to isolation by filtration.

The di-esylate Form A was prepared by reacting approximately 500 mg 3-amino-6-(4-{3-[(3-methoxypropyl)amino]propyl}phenyl)-N-pyridin-3-ylpyrazine-2-carboxamide Form B with 2 molar equivalents of counter-ion in 10 mL of IPA. The reaction was carried out at room temperature and the mixture was stirred for 5 days prior to isolation by filtration.

The 3-amino-6-(4-{3-[(3-methoxypropyl)amino]propyl}phenyl)-N-pyridin-3-ylpyrazine-2-carboxamide mono-tosylate Form A was determined to be crystalline by XRPD (see FIG. 8) and had the following X-Ray Powder Diffraction peaks:

| Angle 2-Theta (2θ) | Intensity % |
| --- | --- |
| 8.0 | 100 |
| 11.7 | 19 |
| 14.8 | 24 |
| 20.0 | 10 |
| 20.9 | 10 |
| 21.5 | 12 |
| 22.2 | 27 |
| 23.0 | 53 |
| 27.5 | 13 |
| 28.0 | 11 |

Figure 9:
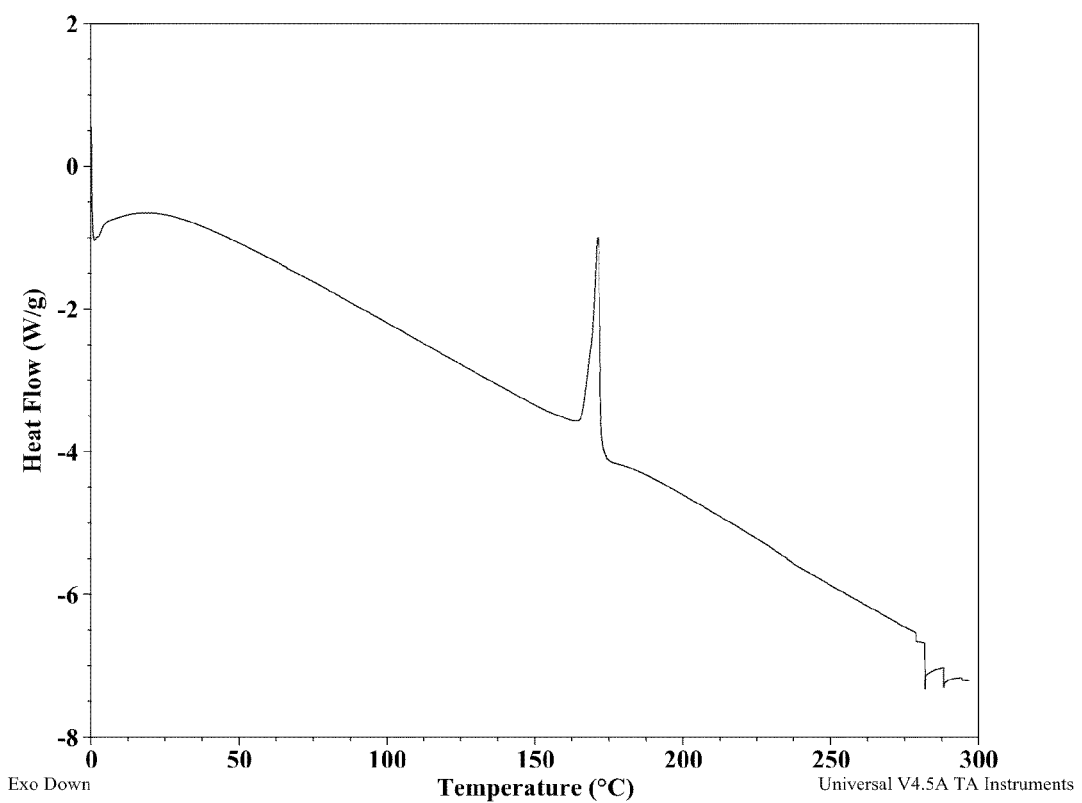
FIG. 9: DSC-Thermogram for Form A of 3-amino-6-(4-{3-[(3-methoxypropyl)amino]propyl}phenyl)-N-pyridin-3-ylpyrazine-2-carboxamide mono-tosylate.

DSC analysis of 3-amino-6-(4-{3-[(3-methoxypropyl)amino]propyl}phenyl)-N-pyridin-3-ylpyrazine-2-carboxamide mono-tosylate Form A was also carried out (FIG. 9), using a heating rate of 10° C./min, and showed a melt with an onset of 168° C. and a peak at 171° C. Thus, DSC analysis shows 3-amino-6-(4-{3-[(3-methoxypropyl)amino]propyl}phenyl)-N-pyridin-3-ylpyrazine-2-carboxamide mono-tosylate Form A is a high melting solid with an to onset of melting at about 168° C. and a peak at about 171° C.

The 3-amino-6-(4-{3-[(3-methoxypropyl)amino]propyl}phenyl)-N-pyridin-3-ylpyrazine-2-carboxamide di-esylate Form A was determined to be crystalline by XRPD (see FIG. 10) and had the following X-Ray Powder Diffraction peaks:

| Angle 2-Theta (2θ) | Intensity % |
|---|---|
| 5.2 | 100 |
| 10.4 | 9 |
| 12.7 | 32 |
| 15.0 | 7 |
| 16.9 | 15 |
| 17.3 | 13 |
| 19.1 | 21 |
| 19.6 | 11 |
| 20.0 | 5 |
| 23.5 | 15 |

Figure 11:
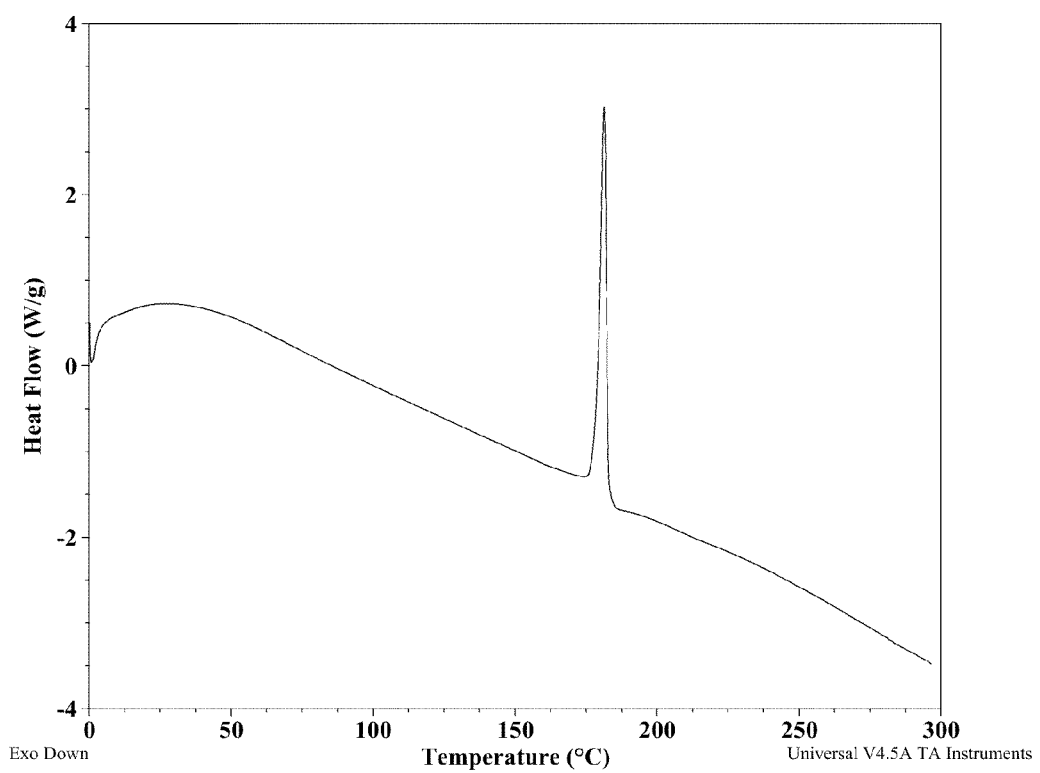
FIG. 11: DSC-Thermogram for Form A of 3-amino-6-(4-{3-[(3-methoxypropyl)amino]propyl}phenyl)-N-pyridin-3-ylpyrazine-2-carboxamide di-esylate.

DSC analysis of 3-amino-6-(4-{3-[(3-methoxypropyl)amino]propyl}phenyl)-N-pyridin-3-ylpyrazine-2-carboxamide di-esylate Form A was also carried out (FIG. 11), using a heating rate of 10° C./min, and showed a melt with an onset of 179° C. and a peak at 181° C. Thus, DSC analysis shows that 3-amino-6-(4-{3-[(3-methoxypropyl)amino]propyl}phenyl)-N-pyridin-3-ylpyrazine-2-carboxamide di-esylate Form A is a high melting solid with an onset of melting at about 179° C. and a peak at about 181° C.

The 3-amino-6-(4-{3-[(3-methoxypropyl)amino]propyl}phenyl)-N-pyridin-3-ylpyrazine-2-carboxamide mono-DL-mandelate Form A was determined to be crystalline by XRPD (see FIG. 12) and had the following X-Ray Powder Diffraction peaks:

| Angle 2-Theta (2θ) | Intensity % |
|---|---|
| 2.7 | 84 |
| 5.2 | 39 |
| 7.8 | 74 |
| 9.6 | 50 |
| 10.5 | 100 |
| 12.3 | 13 |
| 13.1 | 41 |
| 15.7 | 20 |
| 18.4 | 51 |
| 2.7 | 84 |

Figure 13:
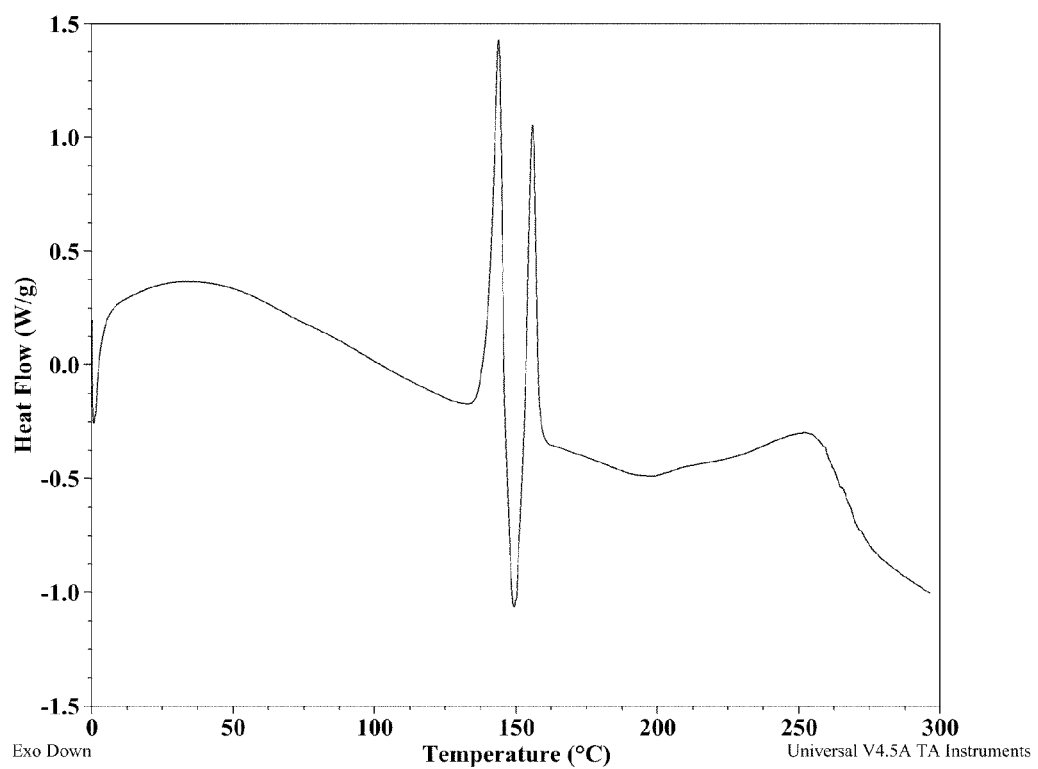
FIG. 13: DSC-Thermogram for Form A of 3-amino-6-(4-{3-[(3-methoxypropyl)amino]propyl}phenyl)-N-pyridin-3-ylpyrazine-2-carboxamide mono-DL-mandelate.

DSC analysis of 3-amino-6-(4-{3-[(3-methoxypropyl)amino]propyl}phenyl)-N-pyridin-3-ylpyrazine-2-carboxamide mono-DL-mandelate Form A was also carried out (FIG. 13), using a heating rate of 10° C./min, and showed an initial endothermic event thought to correspond to a melt, with an onset of about 140° C. and a peak at about 144° C. This was followed by an exothermic (recrystallisation) event with an onset of about 146° C. and peak of about 149° C., followed by a final meting event with an onset of about 153° C. and a peak of about 156° C. Thus, DSC analysis shows that 3-amino-6-(4-{3-[(3-methoxypropyl)amino]propyl}phenyl)-N-pyridin-3-ylpyrazine-2-carboxamide mono-DL-mandelate Form A undergoes a melt-recrystallisation-melt sequence of transitions with an initial an onset of melting at about 140° C. and a peak at about 144° C.

The 3-amino-6-(4-{3-[(3-methoxypropyl)amino]propyl}phenyl)-N-pyridin-3-ylpyrazine-2-carboxamide mono-benzoate Form A was determined to be crystalline by XRPD (see FIG. 14) and had the following X-Ray Powder Diffraction peaks:

| Angle 2-Theta (2θ) | Intensity % |
|---|---|
| 5.3 | 100 |
| 6.2 | 18 |
| 9.2 | 57 |
| 9.8 | 19 |
| 11.9 | 14 |
| 16.6 | 25 |
| 17.8 | 38 |
| 18.1 | 56 |
| 19.5 | 20 |
| 24.6 | 39 |

Figure 15:
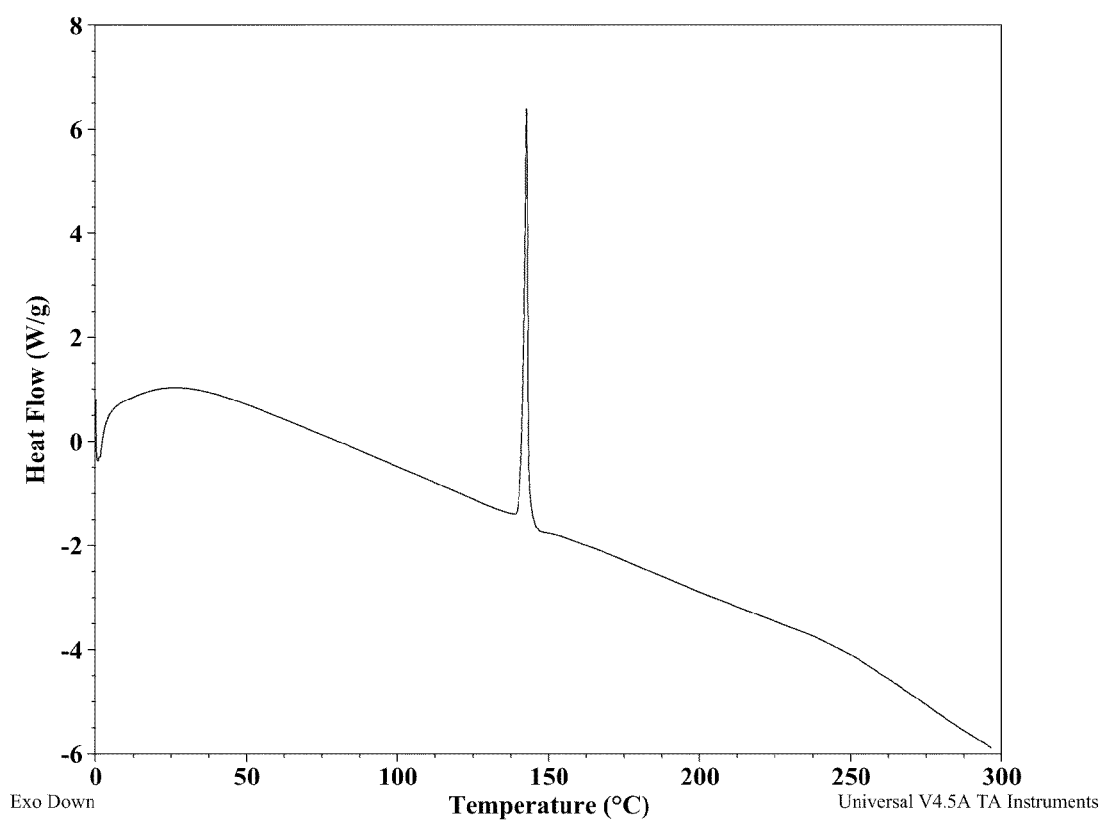
FIG. 15: DSC-Thermogram for Form A of 3-amino-6-(4-{3-[(3-methoxypropyl)amino]propyl}phenyl)-N-pyridin-3-ylpyrazine-2-carboxamide mono-benzoate.

DSC analysis of 3-amino-6-(4-{3-[(3-methoxypropyl)amino]propyl}phenyl)-N-pyridin-3-ylpyrazine-2-carboxamide mono-benzoate Form A was also carried out (FIG. 15), using a heating rate of 10° C./min, and showed a melt with an onset of 141° C. and a peak at 143° C. Thus, DSC analysis shows that 3-amino-6-(4-{3-[(3-methoxypropyl)amino]propyl}phenyl)-N-pyridin-3-ylpyrazine-2-carboxamide mono-benzoate Form A is a high melting solid with an onset of melting at about 141° C. and a peak at 143° C.

EXAMPLE 5

3-Amino-6-(4-{3-[(2-methoxyethyl)amino]propyl}phenyl)-N-pyridin-3-ylpyrazine-2-carboxamide tri-hydrochloride

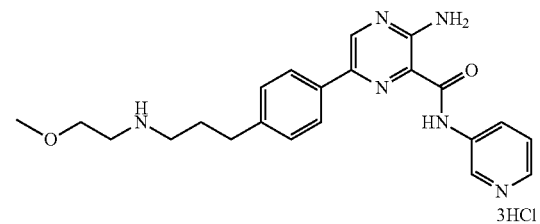

The title compound was prepared using analogous methods to those described in Example 1, except that 2-methoxyethylamine was used instead of 3-methoxypropylamine in step (ix).

$^1$H NMR (400 MHz, CD$_3$OD) δ 9.65 (s, 1H), 8.96 (d, J=8.0 Hz, 1H), 8.83 (s, 1H), 8.64 (d, J=5.6 Hz, 1H), 8.12 (m, 3H), 7.42 (d, J=7.6 Hz, 2H), 3.66 (m, 2H), 3.48 (s, 3H), 3.23 (m, 2H), 3.10 (m, 2H), 2.82 (m, 2H), 2.11 (m, 2H).

LCMS: Retention Time=0.761 min.

EXAMPLE 6

3-Amino-6-(4-{2-[(3-methoxypropyl)amino]ethyl}phenyl)-N-pyridin-3-ylpyrazine-2-carboxamide

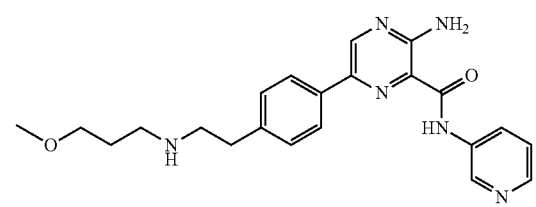

The title compound was prepared in accordance with the following procedure:

(i) (4-Bromophenylethoxy)(tert-butyl)dimethylsilane

To a solution of 2-(4-bromophenyl)ethanol (5 g, 25 mmol) in anhydrous dichloromethane (150 mL) was added triethylamine (7.5 g, 75 mmol), DMAP (300 mg, 2.5 mmol) and tert-butyldimethylsilyl chloride (7.5 g, 50 mmol) sequentially. The resulting pale brown solution was stirred at room temperature for overnight. The reaction mixture was extracted with dichloromethane and water three times. The combined organic layers were dried over anhydrous sodiumsulphate, filtered and concentrated in vacuo. The crude product was subjected to column chromatography with PE as eluant to afford the subtitle compound as a brown oil (7.1 g).

$^1$H NMR (400 MHz, CDCl$_3$) δ 7.41 (dd, J=6.4, 2.0 Hz, 2H), 7.10 (dd, J=6.4, 2.0 Hz, 2H), 3.80 (t, J=6.8 Hz, 2H), 2.79 (t, J=6.8 Hz, 2H), 0.88 (s, 9H), 0.00 (s, 6H).

(ii) 3-Amino-6-(4-(2-(tert-butyldimethylsilyloxy)ethyl)phenyl)-N-(pyridin-3-yl)pyrazine-2-carboxamide A mixture of the product of step (i) (6.9 g, 27.1 mmol), KOAc (6.6 g, 67.8 mmol), Pd(dppf)Cl$_2$ (0.82 g, 1.13 mmol) in dioxane (150 mL) was degassed and backfilled with N$_2$ three times. The mixture was stirred at 90° C. under N$_2$ overnight. The reaction mixture was cooled to room temperature and the product of step (v) in Example 1 (6.6 g, 22.6 mmol), Pd(dppf)Cl$_2$ (0.5 g, 0.7 mmol), water (50 mL) and Na$_2$CO$_3$ (7.2 g, 67.8 mmol) were added into the mixture. The resulting solution was degassed with N$_2$ three times and stirred at 90° C. under N$_2$ for an additional 7 hours. The reaction mixture was extracted with dichloromethane three times and the combined organic layers were dried over anhydrous sodiumsulphate, filtered and concentrated in vacuo. The residue was purified by column with PE:EtOAc=5:1→3:1 as eluants to afford the subtitle compound as a yellow solid (4.1 g)

$^1$H NMR (400 MHz, CDCl$_3$) δ 9.95 (s, 1H), 8.79 (d, J=2.4 Hz, 1H), 8.68 (s, 1H), 8.41 (d, J=2.4 Hz, 1H), 8.25 (d, J=8.2 Hz, 1H), 7.80 (d, J=8.0 Hz, 2H), 7.39-7.30 (m, 3H), 3.84 (t, J=6.8 Hz, 2H), 2.88 (t, J=6.8 Hz, 2H), 0.87 (s, 9H), 0.00 (s, 6H).

(iii) 3-Amino-6-(4-(2-hydroxyethyl)phenyl)-N-(pyridin-3-yl)pyrazine-2-carboxamide A solution of the product of step (ii) (4.1 g, 9.13 mmol) and tetrabutyl ammonium fluoride (4.8 g, 18.3 mmol) in THF (150 mL) was stirred at room temperature overnight. The mixture was concentrated in vacuo and the residue extracted with dichloromethane and washed with water. The combined organic layers were dried overanhydrous sodium sulphate, filtered and concentrated in vacuo to obtain the subtitle compounds (2.5 g).

LCMS Retention time=0.801 min

(iv) 4-(5-Amino-6-(pyridin-3-ylcarbamoyl)pyrazin-2-yl)phenethyl methanesulfonate To a solution of the product of step (iii) (2.5 g, 7.5 mmol, 1.0 eq) and TEA (2.3 g, 22.5 mmol) in dry dichlormethane was added MsCl (1.7 g, 15 mmol). The reaction mixture was stirred at room temperature for 4 hours. The solvent was removed under reduced pressure and the residue purified by column to afford the subtitled compounds (1.9 g).

$^1$H NMR (400 MHz, CDCl$_3$) δ 9.87 (s, 1H), 8.76 (s, 1H), 8.64 (s, 1H), 8.36 (d, J=4.0 Hz, 1H), 8.24 (d, J=8.4 Hz, 1H), 7.80 (d, J=8.0 Hz, 2H), 7.38-7.24 (m, 3H), 4.42 (t, J=6.8 Hz, 2H), 3.08 (t, J=6.8 Hz, 2H), 2.87 (s, 3H).

(v) 3-Amino-6-(4-{2-[(3-methoxypropyl)amino]ethyl}phenyl)-N-pyridin-3-ylpyrazine-2-carboxamide A mixture of the product of step (iv) (250 mg, 0.61 mmol), K$_2$CO$_3$ (250 mg, 1.8 mmol), 3-methoxypropylamine (82 mg, 0.92 mmol) in MeCN (20 mL, Aldrich, HPLC grade) was stirred at 90° C. under N$_2$ atmosphere overnight. The reaction mixture was cooled to room temperature and filtered. The filtrate was concentrated in vacuo and the residue subjected to prep-HPLC for purification, the eluents were concentrated and 1N NaOH solution added into the residue to control the pH=8~9. The mixture was extracted with DCM three times. The combined extracts was dried over anhydrous sodium sulphate, filtered, concentrated in vacuo, which afforded the title compound (yellow solid, 158 mg)

$^1$H NMR (400 MHz, CDCl$_3$) δ 9.89 (s, 1H), 8.74 (d, J=2.4 Hz, 1H), 8.63 (s, 1H), 8.35 (d, J=4.4 Hz, 1H), 8.23 (d, J=8.4 Hz, 1H), 7.76 (d, J=8.4 Hz, 2H), 7.40-7.27 (m, 3H), 3.37 (t, J=6.2 Hz, 2H), 3.23 (s, 3H), 2.90-2.77 (m, 4H), 2.69 (t, J=7.0 Hz, 2H), 1.76-1.62 (m, 2H).

LCMS: Retention Time=0.741 min.

EXAMPLE 7

3-Amino-6-(4-{2-[(2-methoxyethyl)amino]ethyl}phenyl)-N-pyridin-3-ylpyrazine-2-carboxamide tri-hydrochloride

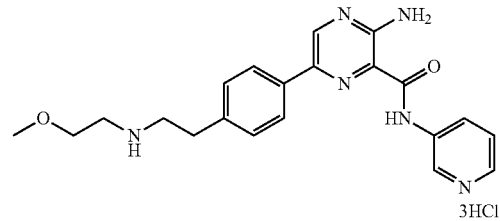

3-Amino-6-(4-{2-[(2-methoxyethyl)amino]ethyl}phenyl)-N-pyridin-3-ylpyrazine-2-carboxamide was prepared using analogous procedures to those described in Example 6, except that 2-methoxyethylamine was used instead of 3-methoxypropylamine in step (v). MeCN was added to 3-Amino-6-(4-{2-[(2-methoxyethyl)amino]ethyl}phenyl)-N-pyridin-3-ylpyrazine-2-carboxamide and 0.5 M-aqueous HCl (20 mL) was also added. The resulting yellow solution was then lyophilized, which afforded the title compound as a tri-hydrochloride salt.

$^1$H NMR (400 MHz, CD$_3$OD) δ 9.66 (s, 1H), 8.98 (d, J=8.8 Hz, 1H), 8.85 (s, 1H), 8.65 (d, J=5.6 Hz, 1H), 8.17-8.12 (m, 3H), 7.48 (d, J=8.4 Hz, 2H), 3.70 (t, J=4.8 Hz, 2H), 3.44 (s, 3H), 3.35-3.28 (m, 4H), 3.13-3.08 (m, 2H).

LCMS: Retention Time=0.720 min.

The invention claimed is:

1. A compound of Formula I:

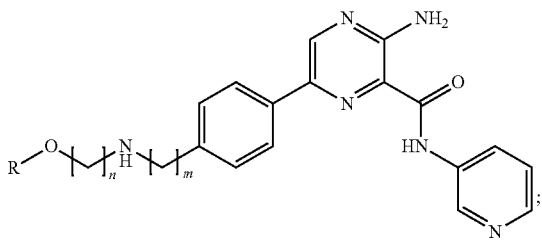

in which:
n is 2 or 3;
m is 2 or 3;
R is methyl or ethyl; or a pharmaceutically-acceptable salt thereof.

2. A compound according to claim 1, which is 3-amino-6-(4-{3-[(3-methoxypropyl)amino]propyl}phenyl)-N-pyridin-3-ylpyrazine-2-carboxamide; or a pharmaceutically-acceptable salt thereof.

3. A compound of the Formula I according to claim 1, which is 3-amino-6-(4-{3-[(3-methoxypropyl)amino]propyl}phenyl)-N-pyridin-3-ylpyrazine-2-carboxamide trihydrochloride.

4. A compound of the Formula I according to claim 1, which is 3-amino-6-(4-{3-[(3-methoxypropyl)amino]propyl}phenyl)-N-pyridin-3-ylpyrazine-2-carboxamide mono-besylate.

5. A compound of the Formula I according to claim 1, which is 3-amino-6-(4-{3-[(3-methoxypropyl)amino]propyl}phenyl)-N-pyridin-3-ylpyrazine-2-carboxamide mono-tosylate.

6. A pharmaceutical composition, which comprises a compound of the Formula I, or a pharmaceutically-acceptable salt thereof, according to any one of claims 1 to 5 in association with a pharmaceutically-acceptable diluent or carrier.

* * * * *